United States Patent [19]

Whittaker et al.

[11] Patent Number: 5,314,880

[45] Date of Patent: May 24, 1994

[54] BENZIMIDAZOLE DERIVATIVES

[75] Inventors: Mark Whittaker, Oxford; Christopher D. Floyd; Jonathan P. Dickens, both of Buckinghamshire; Alan H. Davidson, Oxfordshire, all of England

[73] Assignee: British Bio-technology Limited, Oxford, England

[21] Appl. No.: 752,443

[22] Filed: Sep. 30, 1991

[30] Foreign Application Priority Data

Feb. 23, 1989 [GB] United Kingdom ............... 8904174

[51] Int. Cl.$^5$ .................. A61K 31/415; A61K 31/44; C07D 235/04; C07D 417/12

[52] U.S. Cl. ..................................... 514/80; 514/338; 514/381; 514/382; 514/394; 514/395; 514/365; 548/113; 548/181; 548/252; 548/253; 548/254; 548/302.1; 548/304.4; 548/307.7; 548/306.4; 548/307.1; 548/309.7; 548/310.1; 548/310.4; 546/22; 546/271

[58] Field of Search ............... 514/80, 338, 381, 382, 514/394, 395, 365; 548/302.1, 304.4, 304.7, 306.4, 307.1, 309.7, 310.1, 310.4, 113, 252, 253, 254, 181; 546/22, 271

[56] References Cited

U.S. PATENT DOCUMENTS 3,317,554  5/1967  Goldsmith et al. .................. 514/80

FOREIGN PATENT DOCUMENTS

| 0144804 | 6/1985 | European Pat. Off. . |
| 0186190 | 7/1986 | European Pat. Off. . |
| 0190817 | 8/1986 | European Pat. Off. . |
| 0238202 | 9/1987 | European Pat. Off. . |
| 0260613 | 3/1988 | European Pat. Off. . |
| 0264114 | 4/1988 | European Pat. Off. . |
| WO8908653 | 3/1989 | PCT Int'l Appl. . |
| 8908653 | 9/1989 | World Int. Prop. O. . |
| 9009997 | 9/1990 | World Int. Prop. O. . |

OTHER PUBLICATIONS

Kishida et al., Chem. Abstr., vol. 106, No. 3; 18545y (1987).

Hirosi et al., Chem. Abstr., vol. 102, No. 19; 166754y (1985).

Kisida et al., Chem. Abstr., vol. 104, No. 21; 186419n (1986).

Kisida et al., Chem. Abstr., vol. 105, No. 15; 133889e (1986).

Primary Examiner—Johann Richter
Attorney, Agent, or Firm—Allegretti & Witcoff, Ltd.

[57] ABSTRACT

Compounds of general formula I:

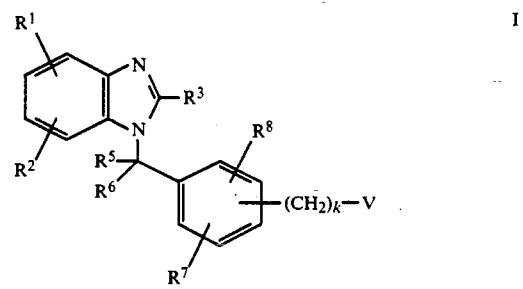

wherein: each of $R^1$-$R^8$, k, and V represent disclosed functional groups that have been chosen such that all disclosed variations of compound I and their pharmaceutically and veterinarily acceptable acid addition salts and hydrates are antagonists of platelet activating factor (PAF) and as such are useful in the treatment or amelioration of various diseases or disorders mediated by PAF.

27 Claims, No Drawings

BENZIMIDAZOLE DERIVATIVES

This invention relates to benzimidazol, derivatives which are active as platelet activating factor antagonists.

Platelet Activating Factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells, resulting in a variety of physiological responses which include hypotension, thrombocytopenia, bronchoconstriction, circulatory shock and increased vascular permeability (oedema/erythema). It is known that these physiological effects occur in many inflammatory and allergic diseases and PAF has been found to be involved in a number of such conditions including asthma, endotoxin shock, glomerulonephritis, immune regulation and psoriasis. Examples of compounds which have been disclosed as possessing activity as PAF antagonists include glycerol derivatives (in EP-A-0238202), α-[(phenylmethoxy)methyl]pyridinealkanol derivatives (EP-A-0264114), 2,5-diaryltetrahydrofurans (EP-A-0144804) and imidazopyridine derivatives (EP-A-0260613 and WO-A-8908653).

According to a first aspect of the invention there is provided a compound of general formula I:

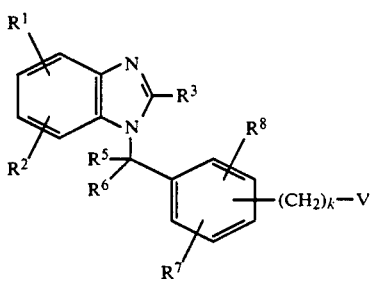

I wherein:

each of $R^1$ and $R^2$ represents independently hydrogen, $C_1-C_6$ alkyl, $C_2-C_6$ alkenyl, halogen, CN, $CO_2H$, $CO_2(C_1-C_6$ alkyl), $CO_2(C_3-C_8)$cycloalkyl, $CONH_2$, CHO, $CH_2OH$, $CF_3$, $C_1-C_6$ alkoxy, $C_1-C_6$ alkylthio, $SO(C_1-C_6)$-alkyl, $SO_2(C_1-C_6$ alkyl), $SO_3H$, $NH_2$, NHCOMe, or $NO_2$ or $R^1$ and $R^2$ together with the carbon atoms to which they are attached form a fused phenyl ring;

$R_3$ represents a hydrogen, $C_1-C_6$ alkyl, $C_2-C_6$ alkenyl, $C_1-C_6$ alkoxy, $C_1-C_6$ alkylthio, $C_1-C_6$ alkoxy ($C_1-C_6$ alkyl), $C_1-C_6$ alkylthio ($C_1-C_6$ alkyl), $SO(C_1-C_6$ alkyl), $SO_2(C_1-C_6$ alkyl), $CF_3$, phenyl ($C_1-C_6$ alkyl), thiophenyl, thiazole, pyridyl or a

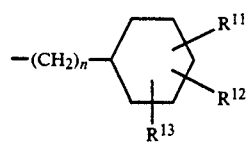

group wherein $R^4$ represents hydrogen, $C_1-C_6$ alkyl, $C_2-C_6$ alkenyl, halogen, OH, SH, CN, $CO_2H$, $CO_2(C_1-C_6$ alkyl), $CONH_2$, CHO, $CH_2OH$, $CF_3$, $C_1-C_6$ alkoxy, $C_1-C_6$ alkylthio, $SO(C_1-C_6$ alkyl), $SO_2(C_1-C_6$ alkyl), $NH_2$, NHCOMe, or $NO_2$;

each of $R^5$ and $R^6$ represents independently hydrogen, $C_1-C_6$ alkyl, $C_2-C_6$ alkenyl, $CO_2$ ($C_1-C_6$ alkyl), $C_1-C_6$ alkylthio, $SO(C_1-C_6$ alkyl), $SO_2(C_1-C_6$ alkyl), $C_1-C_6$ alkylthio ($C_1-C_6$ alkyl), $C_1-C_6$ alkoxy ($C_1-C_6$ alkyl), phenyl ($C_1-C_6$ alkyl) and thiophenyl;

k is an integer from 0 to 2;

each of $R^7$ and $R^8$ independently represents hydrogen, $C_1-C_6$ alkyl, $C_2-C_6$ alkenyl, $C_1-C_6$ alkoxy, $C_1-C_6$ alkylthio, $C_1-C_6$ alkoxy ($C_1-C_6$ alkyl), $C_1-C_6$ alkylthio ($C_1-C_6$ alkyl), halogen, $CF_3$, CN, OH, SH, $CH_2OH$, $CH_2SH$ or $CONH_2$;

V represents a) a $YNR^9R^{10}$ group wherein Y is $SO_2$, $PO_2$, CO or CS and each of $R^9$ and $R^{10}$ is independently hydrogen, $C_1-C_{18}$ alkyl $C_2-C_{18}$ alkenyl, $C_3-C_8$ cycloalkyl, $C_4-C_8$ cycloalkenyl, phenyl ($C_1-C_6$ alkyl), adamantyl, decalynyl, naphthyl, $C_3-C_8$ cycloalkyl ($C_1-C_6$ alkyl), $C_4-C_8$ cycloalkenyl ($C_1-C_6$ alkyl) or a group G wherein G represents a group:

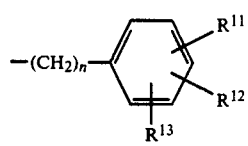

or a group:

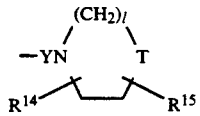

wherein n is an integer of from 1 to 6 and each of $R^{11}$, $R^{12}$ and $R^{13}$ is independently hydrogen, halogen, $C_1-C_{18}$ alkenyl, $C_2-C_{18}$ alkenyl, $C_3-C_8$ cycloalkyl, $C_4-C_8$ cycloalkenyl, phenyl ($C_1-C_6$ alkyl), $C_3-C_8$ cycloalkyl ($C_1-C_6$ alkyl), $C_4-C_8$ cycloalkenyl ($C_1-C_6$ alkyl) or a $C_1-C_6$ alkoxy, benzoxy, $C_1-C_6$ alkylthio, benzthio or benzoyl; or b) a group

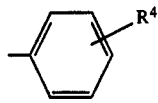

group wherein l is an integer from 1 to 3, Y represents $SO_2$, $PO_2$, CO or CS, each of $R^{14}$ and $R^{15}$ independently represents hydrogen, $C_1-C_{18}$ alkyl, $C_2-C_8$ alkenyl, $C_3-C_8$ cycloalkyl, $C_4-C_8$ cycloalkenyl, phenyl ($C_1-C_6$ alkyl) $C_3-C_8$ cycloalkyl ($C_1-C_6$ alkyl), $C_4-C_8$ cycloalkenyl ($C_1-C_6$ alkyl) or a group G as defined above, T represents O, S, $NR^{16}$, or $CH_2R^{16}$ wherein $R^{16}$ represents hydrogen, $C_1-C_{18}$ alkyl, $C_2-C_{18}$ alkenyl, $C_3-C_8$ cycloalkyl, $C_4-C_8$ cycloalkenyl, phenyl ($C_1-C_6$ alkyl), $C_3-C_8$ cycloalkyl ($C_1-C_6$ alkyl), $C_4-C_8$ cycloalkenyl ($C_1-C_6$ alkyl) or a group G as defined above;

c) a group or a group

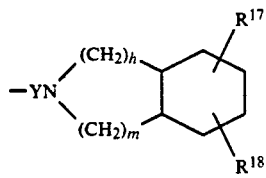

or a group

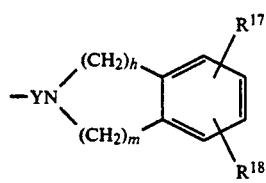

wherein h is an integer from 1 to 2, m is an integer from 0 to 2, Y represents $SO_2$, $PO_2$, CO or CS, each of $R^{17}$ and $R^{18}$ independently represents hydrogen, halogen, $C_1$–$C_8$ alkyl, $C_2$–$C_{18}$ alkenyl, $C_3$–$C_8$ cycloalkyl, $C_4$–$C_8$ cycloalkenyl, phenyl ($C_1$–$C_6$ alkyl), $C_3$–$C_8$ cycloalkyl ($C_1$–$C_6$ alkyl), $C_4$–$C_8$ cycloalkenyl ($C_1$–$C_6$ alkyl), $C_1$–$C_6$ alkoxy, benzoxy, $C_1$–$C_6$ alkylthio, benzthio or benzoyl;

d) a $ZR^{19}$ group wherein Z represents tetrazole, CO, $CO_2$, $NR^{20}CO$, $NR^{20}CO_2$, $SO_2$, $NR^{20}SO_2$, $O_2C$, or $OCONR^{20}$ and each of $R^{19}$ and $R^{20}$ independently represents hydrogen, $C_1$–$C_8$ alkyl, $C_2$–$C_{18}$ alkenyl, $C_3$–$C_8$ cycloalkyl, $C_4$–$C_8$ cycloalkenyl, adamantyl, decalynyl, phenyl ($C_1$–$C_6$ alkyl), $C_3$–$C_8$ cycloalkyl ($C_1$–$C_6$ alkyl), $C_4$–$C_8$ cycloalkenyl ($C_1$–$C_6$ alkyl), naphthyl, or a group G as defined above;

e) an $NR^{21}POR^{22}R^{23}$ group wherein each of $R^{21}$, $R^{22}$ and $R^{23}$ independently represents hydrogen, $C_1$–$C_{18}$ alkyl, $C_2$–$C_{18}$ alkenyl, $C_3$–$C_8$ cycloalkyl, $C_4$–$C_8$ cycloalkenyl, adamantyl, decalynyl, phenyl ($C_1$–$C_6$ alkyl) $C_3$–$C_8$ cycloalkyl ($C_1$–$C_6$ alkyl), $C_4$–$C_8$ cycloalkenyl ($C_1$–$C_6$ alkyl) naphthyl or a group G as defined above;

or a pharmaceutically or veterinarily acceptable acid addition salt or hydrate thereof.

Hereafter in this specification the term "compound" includes "salt" or "hydrate" unless the context requires otherwise.

Certain compounds within the above and other general formulae in this specification exist in two or more enantiomeric forms, depending on the number of asymmetric carbon atoms present. Unless the context requires otherwise, it is to be understood that all isomers, including optical isomers, and mixtures of isomers, including racemates, are included.

As used herein the term "$C_1$–$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_1$–$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl tetradecyl, pentadecyl, hexadecyl, heptadecyl and octadecyl.

As used herein the term "$C_2$–$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_2$–$C_{18}$ alkenyl" refers to straight chain or branched chain hydrocarbon groups is having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl and farnesyl.

As used herein the term "$C_1$–$C_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$C_1$–$C_6$ alkylthio" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$–$C_8$ cycloalkenyl" refers to an alicyclic group having from 4 to 8 carbon atoms and having in addition one, or more double bonds. Illustrative of such cycloalkenyl groups are cyclopentenyl, cyclohexenyl, cycloheptenyl and cyclooctenyl.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

$R^1$ represents a hydrogen atom, a halogen (for example chlorine) atom, a $C_1$–$C_6$ alkyl (for example methyl) group, a $C_1$–$C_6$ alkoxy (for example methoxy) group, a nitro group or, together with $R^2$ and the carbon atoms to which they are attached, forms a fused phenyl ring;

$R^2$ represents a hydrogen atom, a $C_1$–$C_6$ alkyl (for example methyl) group, or together with $R^1$ and the carbon atoms to which they are attached, forms a fused phenyl ring;

$R^3$ represents a hydrogen atom, a $C_1$–$C_6$ alkyl (for example methyl, ethyl, isopropyl or tert-butyl) group, a $C_1$–$C_6$ alkylthio (for example thiomethyl) group, a $SO(C_1$–$C_6)$alkyl (for example methylsulphinyl) group, a $SO_2(C_1$–$C_6)$ alkyl (for example methylsulphonyl) group, a $C_1$–$C_6$ alkylthio($C_1$–$C_6$alkyl) (for example 2-ethyl thiomethyl) group, a $CF_3$ group, a thiazole (for example 4-thiazolyl) group, a pyridyl (for example 2-pyridyl) group, or a

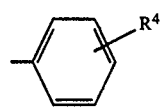

group;

$R^4$ represents a hydrogen or a halogen (for example chlorine) atom;

$R^5$ represents a hydrogen atom, a $C_1$–$C_6$ alkyl (for example methyl or ethyl) group, a $C_2$–$C_6$ alkenyl (for example allyl) group, a $C_1$–$C_6$ alkylthio (for example thiomethyl or thioethyl) group, a $SO_2C_1$–$C_6$ (for example methylsulphonyl) group or a thiophenyl group;

$R^6$ represents a hydrogen atom, or a $C_1$–$C_6$ alkylthio (for example thiomethyl) group;

k represents an integer of zero;

$R^7$ represents a hydrogen atom, a $C_1$–$C_6$ alkoxy (for example methoxy) group or a halogen (for example fluorine or bromine) atom;

$R^8$ represents a hydrogen atom;

V represents a $YNR^9R^{10}$ group, a

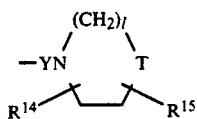

group, a

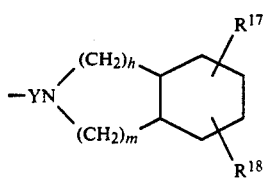

group, a

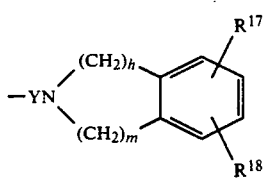

group, a $ZR^{19}$ group or a $NR^{21}POR^{22}R^{23}$ group;

Y represents CO or $SO_2$;

$R^9$ represents a hydrogen atom, a $C_1$–$C_{18}$ alkyl (for example methyl or ethyl) group, a $C_3$–$C_8$ cycloalkyl (for example cyclohexyl) group, or a group G;

$R^{10}$ represents a $C_1$–$C_{18}$ (for example decyl or tetradecyl) group, a $C_3$–$C_8$ cycloalkyl (for example cyclohexyl) group, an adamantyl (for example 1-adamantyl) group, a naphthyl (for example 1,2,3,4-tetrahydro-1-naphthyl) group or a group G;

G represents either a

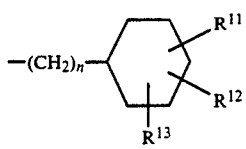

group or a

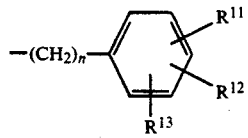

group;

n represents an integer of 0, 1 or 2;

$R^{11}$ represents a hydrogen atom, a halogen (for example chlorine or bromine) atom, a $C_1$–$C_{18}$ alkyl (for example tert-butyl) group, a $C_1$–$C_6$ alkoxy (for example methoxy) group, a benzoxy group or a benzoyl group;

$R^{12}$ represents a hydrogen atom or a $C_1$–$C_6$ alkoxy (for example methoxy) group;

$R^{13}$ represents a hydrogen atom or a $C_1$–$C_6$ alkoxy (for example methoxy) group;

l represents an integer of 2;

$R^{14}$ represents a hydrogen atom or a $C_1$–$C_{18}$ alkyl (for example methyl) group;

$R^{15}$ represents a hydrogen atom or a $C_1$–$C_{18}$ alkyl (for example methyl) group;

T represents an oxygen atom, an $NR^{16}$ group or a $CHR^{16}$ group;

$R^{16}$ represents a hydrogen atom, a $C_1$–$C_{18}$ alkyl (for example decyl) group or a phenyl ($C_1$–$C_6$ alkyl) (for example 3-phenylpropyl) group, or a group G;

h represents an integer of 3;

m represents an integer of 0;

$R^{17}$ represents a hydrogen atom;

$R^{18}$ represents a hydrogen atom;

Z represents a CO group, $CO_2$ group, $NR^{20}CO$ group or $NR^{20}SO_2$ group;

$R^{19}$ represents a $C_1$–$C_{18}$ alkyl (for example ethyl) group, a $C_3$–$C_8$ cycloalkyl (for example cyclohexyl group) group, a naphthyl (for example 2-naphthyl) group, or a group G;

$R^{20}$ represents a hydrogen atom or a $C_1$–$C_{18}$ alkyl (for example methyl) group;

$R^{21}$ represents a $C_1$–$C_{18}$ alkyl (for example methyl) group;

$R^{22}$ represents a group G; and/or $R^{23}$ represents a group G.

Particularly preferred compounds include:
1. Ethyl 4-(1H-benzimidazylmethyl)benzoate,
2. Ethyl 3-bromo-4-(1H-benzimidazylmethyl)benzoate,
3. Ethyl 3-fluoro-4-(1H-benzimidazylmethyl)benzoate,
4. Ethyl 3-methoxy-4-(1H-benzimidazylmethyl)benzoate,
5. (A) Ethyl 4-(1H-6-methoxybenzimidazylmethyl)benzoate, (B) Ethyl 4-(1H-5-methoxybenzimidazylmethyl)benzoate,
6. Ethyl 4-(1H-5-nitrobenzimidazylmethyl)benzoate,
7. N-Cyclohexyl 4-(1H-benzimidazylmethyl)benzamide,
8. N-Benzyl 4-(1H-benzimidazylmethyl)benzamide,
9. N-Phenyl 4-(1H-benzimidazylmethyl)benzamide,
10. N-3-Chlorophenyl 4-(1H-benzimidazylmethyl)benzamide,
11. N-3-Methoxyphenyl 4-(1H-benzimidazylmethyl)benzamide,
12. N-3-Benzoxyphenyl 4-(1H-benzimidazylmethyl)benzamide,
13. N-Tetradecyl 4-(1H-benzimidazylmethyl)benzamide,
14. N-Cyclohexyl 3-(1H-benzimidazylmethyl)benzamide, 15. N-Cyclohexyl-N-methyl 3-(1H-benzimidazylmethyl)benzamide,
16. Benzoyl 4-(1H-2-methylbenzimidazylmethyl)benzene,
17. N-Cyclohexyl-N-methyl 4-(1H-benzimidazylmethyl)benzamide,
18. N-Methyl-N-phenyl-4-(1H-benzimidazylmethyl)benzamide,
19. N-Cyclohexyl-N-ethyl 4-(1H-benzimidazylmethyl)benzamide,
20. N-Cyclohexyl-N-methyl 4-(1H-2-methylbenzimidazylmethyl)benzamide,
21. N-Cyclohexyl-N-ethyl 4-(1H-2-methylbenzimidazylmethyl)benzamide,
22. N,N-Dicyclohexyl 4-(1H-2-methylbenzimidazylmethyl)benzamide,
23. N-Cyclohexyl-N-methyl 4-(1H-2-ethylbenzimidazylmethyl)benzamide,
24. N-Cyclohexyl-N-methyl 4-(1H-2-isopropylbenzimidazylmethyl) benzamide,
25. N-Cyclohexyl-N-methyl 4-(1H-2-tert-butylbenzimidazylmethyl) benzamide,
26. N-Cyclohexyl-N-methyl 4-(1H-2-thiomethylbenzimidazylmethyl) benzamide,
27. N-Cyclohexyl-N-methyl 4-(1H-2-methylsulphinyl-benzimidazylmethyl) benzamide,
28. N-Cyclohexyl-N-methyl 4-(1H-2-methylsulphonyl-benzimidazylmethyl) benzamide,
29. N-Cyclohexyl-N-methyl 4-(1H-2-(2-thiomethylethyl)benzimidazylmethyl)benzamide,
30. N-Cyclohexyl-N-methyl 4-(1H-2-trifluoromethyl-benzimidazylmethyl) benzamide,
31. N-Cyclohexyl-N-methyl 4-(1H-2-(4-thiazolyl)benzimidazylmethyl) benzamide,
32. N-Cyclohexyl-N-methyl 4-(1H-2-phenylbenzimidazylmethyl)benzamide,
33. N-Cyclohexyl-N-methyl 4-(1H-2-(2-chlorophenyl)-benzimidazylmethyl) benzamide,
34. N-Cyclohexyl-N-methyl 4-(1H-5,6-dimethylbenzimidazylmethyl) benzamide,
35. N-Cyclohexyl-N-methyl 3-bromo-4-(1H-2-benzimidazylmethyl) benzamide,
36. N-Cyclohexyl-N-methyl 3-fluoro-4-(1H-2-benzimidazylmethyl) benzamide,
37. N-Cyclohexyl-N-methyl 3-methoxy-4-(1H-2-benzimidazylmethyl) benzamide,
38. N-Cyclohexyl 4-(1H-benzimidazylmethyl)benzenesulphonamide,
39. N-Cyclohexyl 4-(1H-2-methylbenzimidazylmethyl)benzenesulphonamide,
40. N-Cyclohexyl-N-methyl 4-(1H-benzimidazylmethyl)benzenesulphonamide,
41. N-Cyclohexyl-N-methyl 4-(1H-2-methylbenzimidazylmethyl)benzenesulphonamide,
42. N-Cyclohexyl-N-methyl 4-(1H-2-ethylbenzimidazyl methyl)benzenesulphonamide,
43. A) N-Cyclohexyl-N-methyl 4-(1H-2-methyl-5-chlorobenzimidazylmethyl)benzenesulphonamide, B) N-Cyclohexyl-N-methyl 4-(1H-2-methyl-6-chlorobenzimidazylmethyl)benzenesulphonamide,
44. N-Cyclohexyl-N-methyl 4-(1H-2-methyl-5-nitrobenzimidazylmethyl)benzenesulphonamide,
45. N-Cyclohexyl-N-methyl 4-(1H-2-(2-pyridyl)benzimidazylmethyl)benzenesulphonamide,
46. N-cyclohexyl-N-methyl 4-(1H-2,5,6-trimethylbenzimidazylmethyl)benzenesulphonamide,
47. N-Cyclohexyl-N-methyl 4-(1H-naphth[2,3-d]imidazylmethyl)benzenesulphonamide,
48. N-Cyclohexyl-N-methyl 4-(1H-2-methylnaphth[2,3-d]imidazylmethyl)benzenesulphonamide,
49. N-Cyclohexyl-N-ethyl 4-(1H-2-(2-methyl)benzimidazylmethyl) benzenesulphonamide,
50. Piperidinyl 4-(1H-2-methylbenzimidazylmethyl)-benzenesulphonamide,
51. Morpholinyl 4-(1H-2-methylbenzimidazylmethyl)-benzenesulphonamide,
52. Morpholinyl 4-(1H-benzimidazylmethyl)benzenepulphonamide,
53. 2-Methylpiperidinyl 4-(1H-2-methylbenzimidazyl methyl)benzenesulphonamide,
54. N-Methyl-N-4-(1H-2-methylbenzimidazylmethyl)-benzylphenylsulphonamide,
55. N-Methyl-N-4-(1H-2-methylbenzimidazylmethyl)-benzyl 2-naphthylsulphonamide,
56. N-Methyl-N-4-(1H-2-methylbenzimidazylmethyl)-benzyl 4-bromophenylsulphonamide,
57. N-4-(1H-2-Methylbenzimidazylmethyl)benzyl phenylamide,
58. N-4-(1H-2-Methylbenzimidazylmethyl)benzylcyclohexylamide,
59. N-Methyl-N-4-(1H-2-methylbenzimidazylmethyl)-benzyl diphenylphosphoramide,
60. N-Cyclohexyl-N-methyl 4-(1-(1H-benzimidazyl)ethyl)benzamide,
61. N-Cyclohexyl-N-methyl 4-(1-(1H-benzimidazyl)-propyl)benzamide,
62. N-Cyclohexyl-N-methyl 4-(1-(1H-benzimidazyl)-but3-enyl)benzamide,
63. N-Cyclohexyl-N-methyl 4-(1H-benzimidazylthiomethylmethyl)benzamide,
64. N-Cyclohexyl-N-methyl 4-(1H-benzimidazyldithiomethylmethyl)benzamide,
65. N-Cyclohexyl-N-methyl 4-(1H-benzimidazylthioethylmethyl)benzamide,
66. N-Cyclohexyl-N-methyl 4-(1H-benzimidazylthiophenylmethyl)benzamide,
67. N-Cyclohexyl-N-methyl 4-(1H-benzimidazylmethylsulphonylmethyl) benzamide,
68. N-Cyclohexyl-N-methyl 4-(1H-2-methylbenzimidazylthiomethylmethyl)benzamide,
69. N-Cyclohexyl-N-methyl4-(1H-2-thiomethylbenzimidazylthiomethylmethyl)benzamide,
70. N-Cyclohexyl-N-ethyl 4-(1H-benzimidazylthiomethylmethyl)benzamide,
71. N-Cyclohexyl-N-methyl 4-(1H-benzimidazylthiomethylmethyl)benzenesulphonamide,
72. N-3-Chlorophenyl 4-(1H-2-methylbenzimidazylmethyl)benzenesulphonamide,
73. N-Phenyl 4-(1H-2-methylbenzimidazylmethyl)benzenesulphonamide,
74. N-4-Bromophenyl 4-(1H-2-methylbenzimidazylmethyl)benzenesulphonamide,
75. N-3,4-Dimethoxyphenyl 4-(1H-2-methylbenzimidazylmethyl)benzenesulphonamide,
76. N-3,4,5-Trimethoxyphenyl 4-(1H-2-methylbenzimidazylmethyl) benzenesulphonamide,
77. N-3-Benzoylphenyl 4-(1H-2-methylbenzimidazylmethyl)benzenesulphonamide,
78. N-3-Benzoxyphenyl 4-(1H-2-methylbenzimidazylmethyl)benzenesulphonamide,
79. N-Benzyl 4-(1H-2-methylbenzimidazylmethyl)benzenesulphonamide,
80. N-2-Chlorobenzyl 4-(1H-2-methylbenzimidazylmethyl)benzenesulphonamide,
81. N-3-Chlorobenzyl 4-(1H-2-methylbenzimidazylmethyl)benzenesulphonamide, 82. N-4-Chlorobenzyl 4-(1H-2-methylbenzimidazylmethyl)benzenesulphonamide,
83. N-3,4-Dimethoxybenzyl 4-(1H-2-methylbenzimidazylmethyl)benzenesulphonamide,
84. N-4-tert-Butylcyclohexyl 4-(1H-2-methylbenzimidazylmethyl)benzenesulphonamide,
85. N-1,2,3,4-Tetrahydro-1-naphthyl 4-(1H-2-methylbenzimidazylmethyl)benzenesulphonamide,
86. N,N-Dicyclohexyl 4-(1H-2-methylbenzimidazylmethyl)benzenesulphonamide,
87. 4-Phenylpiperidinyl 4-(1H-2-methylbenzimidazylmethyl)benzenesulphonamide,
88. 3,3-Dimethylpiperidinyl 4-(1H-2-methylbenzimidazylmethyl)benzenesulphonamide,
89. 4-(3-Propylphenyl)piperazinyl 4-(1H-2-methylbenzimidazylmethyl)benzenesulphonamide,
90. 4-Decylpiperazinyl 4-(1H-2-methylbenzimidazylmethyl)benzenesulphonamide,
91. N-Decyl 4-(1H-2-methylbenzimidazylmethyl)benzenesulphonamide,
92. trans-Decahydroquinolinyl 4-(1H-2-methylbenzimidazylmethyl)benzenesulphonamide,
93. N-1-Adamantyl 4-(1H-2-methylbenzimidazylmethyl)benzenesulphonamide,
94. N-Methyl-N-phenyl 4-(1H-2-methylbenzimidazylmethyl)benzenesulphonamide,
95. N-Benzyl-N-methyl 4-(1H-2-methylbenzimidazylmethyl)benzenesulphonamide,
96. N-Benzyl-N-phenyl 4-(1H-2-methylbenzimidazylmethyl)benzenesulphonamide,
97. N-Benzyl-N-2-phenylethyl 4-(1H-2-methylbenzimidazylmethyl)benzenesulphonamide,
98. N-3-Chlorobenzyl-N-methyl 4-(1H-2-methylbenzimidazylmethyl)benzenesulphonamide,
99. N-4-Chlorobenzyl-N-methyl 4-(1H-2-methylbenzimidazylmethyl)benzenesulphonamide and
100. N-1-Adamantyl-N-methyl 4-(1H-2-methylbenzimidazylmethyl)benzenesulphonamide.

Preparation of compounds within scope of the invention

The compounds of the general formula I may be prepared by any suitable method known in the art and/or by the following process, which itself forms part of the invention.

According to a second aspect of the invention, there is provided a process for preparing a compound of general formula I as defined above, the process comprising:

(a) treating a benzimidazole represented by general formula II

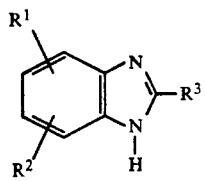

wherein $R^1$, $R^2$ and $R^3$ are as defined in general formula I, with a suitable base (e.g. sodium hydride or potassium hydride), followed by a compound of general formula III

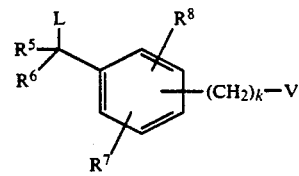

wherein $R^5$, $R^6$, $R^7$, $R^8$, k and V are as defined above, and L is chloro, bromo, iodo, methanesulphonyloxy, p-toluenesulphonyloxy or trifluoromethanesulphonyloxy; or (b) treating a substituted diaminobenzene of general formula IV

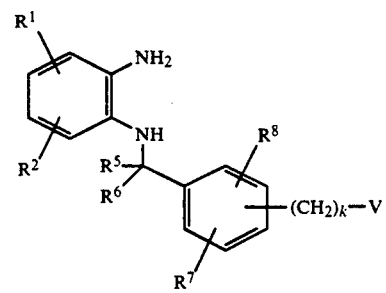

wherein $R^1$, $R^2$, $R^5$, $R^6$, $R^7$, $R^8$, k and V are as defined in general formula I, with a compound of general formula V $$R^3CO_2H \quad\quad V$$

wherein $R^3$ is as defined in general formula I, or a suitable derivative thereof; and (c) optionally after step (a) or step (b) converting, in one or a plurality of steps, a compound of general formula I into another compound of general formula I.

The reaction of step (a) can for preference be conducted in an aprotic solvent, preferably tetrahydrofuran, to yield compounds of general formula I. In the case where an unsymmetrically substituted benzimidazole is used the reaction can yield an isomeric mixture, which is separated by chromatography to yield compounds of general formula I.

In step (b), derivatives of compounds of general formula V, such as acid halides or trialkylorthoformates are suitable substrates for this reaction. Carboxylic acids of general formula V and derivatives are available in the art or can be prepared by procedures known to those skilled in the art.

By means of step (c) compounds of general formula I wherein V is a $YNR^9R^{10}$ group or a YN(heterocyclic) group wherein Y is CO, $R^9$ and $R^{10}$ are as defined for general formula I and N(heterocyclic) is such that V conforms to its definition (b) or (c) in general formula I, may be prepared by the following methods:

i) by treatment of a compound of general formula I wherein Z is $CO_2$ and $R^{19}$ is lower alkyl with hot ethanolic potassium hydroxide to give a carboxylic acid potassium salt which is then treated with an amine of general formula $HNR^9R^{10}$ or HN(heterocycle) in the presence of diphenylphosphorylazide;

ii) by treatment of a compound of general formula I wherein Z is $CO_2$ and $R^{19}$ is hydrogen with an amine of general formula $HNR^9R^{10}$ or HN(heterocycle) in the presence of 1,3-dicyclohexylcarbodiimide;

iii) by treatment of a compound of general formula I wherein Z is CO and $R^{19}$ is halide with an amine of general formula $HNR^9R^{10}$ or HN(heterocycle);

iv) by treatment of a compound of general formula I wherein Z is $CO_2$ and $R^{19}$ is lower alkyl with a dimethylaluminium amide of general formula VII $(Me)_2AlNR^9R^{10}$          VII wherein $R^9$ and $R^{10}$ are as defined in general formula I, which is prepared in situ from trimethylaluminium and an amine of general formula $HNR^9R^{10}$ or HN(heterocycle).

Amines $HNR^9R^{10}$ and HN(heterocycle) are either known in the art or can readily be prepared by those skilled in the art.

Also by means of step (c) compounds of general formula I wherein V is a $YNR^9R^{10}$ group wherein Y is CO or $SO_2$ and $R^9$ and $R^{10}$ are as defined for general formula I, may be prepared by treatment of a compound of general formula I wherein V is a $YNR^9R^{10}$ group wherein $R^9$ is hydrogen and $R^{10}$ is as defined for general formula I with base followed by an electrophile of general formula VII $LR^9$          VII wherein $R^9$ is as defined in general formula I but is not a hydrogen atom, a phenyl or a substituted phenyl group, and L is chloro, bromo, iodo, methanesulphonyloxy, P-toluenesulphonyloxy or trifluoromethanesulphonyloxy.

Also by means of step (c) certain compounds of general formula I wherein V is a $YNR^9R^{10}$ group, a YN(-heterocycle) group (that is to say a

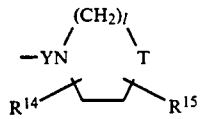

group, a

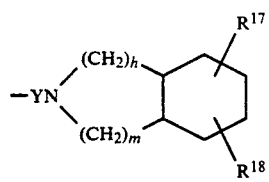

group, or a

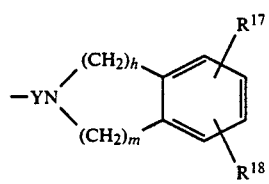

group, or a $ZR^{19}$ group can be prepared by treatment of a compound of general formula I wherein either one or both of $R^5$ and $R^6$ is a hydrogen atom, the group $-(CH_2)_k-V$ is para to the 1H-benzimidazylmethyl group, k is an integer of zero and V is a $YNR^9R^{10}$ group wherein Y is as defined for general formula I, $R^9$ and $R^{10}$ are independently groups, other than a hydrogen atom, as defined for general formula I or V is a $ZR^{19}$ group wherein Z is $CO_2$, or $SO_2$ and $R^{19}$ is a group, other than a hydrogen atom, as defined for general formula I, with a suitable base (e.g. sodium bis(trimethylsilyl)amide) in an aprotic solvent (e.g. tetrahydrofuran) followed by an electrophile of general formula $LR^5$ or $LR^6$ wherein $R^5$ and $R^6$ are $C_1-C_6$ alkyl, $C_3-C_6$ alkenyl, $CO_2C_1-C_6$ alkyl, $C_1-C_6$ alkylthio, $C_1-C_6$ alkylthio ($C_1-C_6$ alkyl), $C_1-C_6$ alkoxy ($C_1-C_6$ alkyl), and phenyl ($C_1-C_6$ alkyl) and L is chloro, bromo, iodo, methanesulphonyloxy, p-toluenesulphonyloxy or trifluoromethanesulphonyloxy. Electrophiles of general formula $LR_5$ or $LR_6$ are available in the art or can be prepared by methods analogous to those known in the art.

Benzimidazoles of general formula II may be prepared by a number of methods. The first method involves treatment of a diaminobenzene of general formula VIII

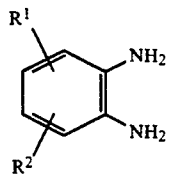          VIII wherein $R^1$ and $R^2$ are as defined in general formula I, with a compound of general formula V $R^3CO_2H$          V wherein $R^3$ is as defined in general formula I. Derivatives of compounds of general formula V, such as acid halides, trialkylorthoformates or imino ether salts are also suitable substrates for this reaction.

Diaminobenzenes of general formula VIII are available in the art or may be prepared by the reduction of a substituted benzene of general formula IX

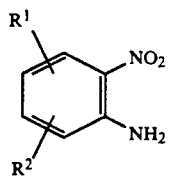          IX wherein $R^1$ and $R^2$ are as defined in general formula I, for example in the presence of hydrogen and a catalyst is such as palladium or platinum.

Substituted benzenes of general formula IX are available in the art or can be prepared by methods analogous to those known in the art.

In a second method benzimidazoles of general formula II may be prepared by the treatment of an amide nitrobenzene of general formula X

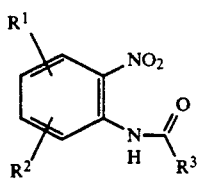

wherein $R^1$, $R^2$ and $R^3$ are as defined in general formula I, with a metal reducing agent (e.g. tin) in acid (e.g. acetic acid). Amide nitrobenzenes of general formula X may be prepared by the treatment of a substituted benzene of general formula IX with an acid chloride of general formula XI

  XI wherein $R^3$ is as defined in general formula I, in an aprotic solvent and in the presence of a suitable base such as, for example, triethylamine. Alternatively, the reaction may be conducted utilising a compound of general formula XII

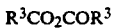  XII wherein $R^3$ is as defined in general formula I.

Another procedure for preparing amide nitrobenzenes of general formula X involves reaction of a substituted benzene of general formula IX with a compound of general formula XIII

  XIII wherein $R^3$ is as defined in general formula I, in the presence of a coupling reagent (e.g. 1,3-dicyclohexylcarbodiimide). Acid chlorides of general formula XI, acid anhydrides of general formula XII and carboxylic acids of general formula XIII are available in the art or can be prepared by methods analogous to those known in the art.

In a third method benzimidazoles of general formula II may be prepared by the treatment of a 2-methyl benzimidazole of general formula XIV

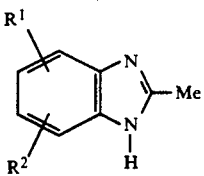  XIV wherein $R^1$ and $R^2$ are defined in general formula I, with two equivalents of a strong base (e.g. n-butyllithium) in an ethereal solvent (e.g. tetrahydrofuran) followed by an electrophile of general formula XV

  XV wherein $R^{24}$ is $C_1$–$C_5$ alkyl, $C_3$–$C_5$ alkenyl, $C_1$–$C_5$ alkoxy, $C_1$–$C_5$ alkylthio, $C_1$–$C_6$ alkoxy ($C_1$–$C_5$ alkyl), $C_1$–$C_6$ alkylthio ($C_1$–$C_5$ alkyl), or phenyl ($C_1$–$C_5$ alkyl), and L is chloro, bromo, iodo, methanesulphonyloxy, p-toluenesulphonyloxy or trifluoromethanesulphonyloxy. 2-Methylbenzimidazoles of general formula XIV are available in the art or may be prepared by treatment of a diaminobenzene of general formula VIII with acetic acid, acetyl chloride, or trialkyl orthoacetate. Electrophiles of general formula XV are available in the art or can be prepared by methods analogous to those known in the art.

Compounds of general formula III may be prepared by methods known to those skilled in the art.

Substituted diaminobenzenes of general formula IV may be prepared by the reduction of an amino nitrobenzene of general formula XVI

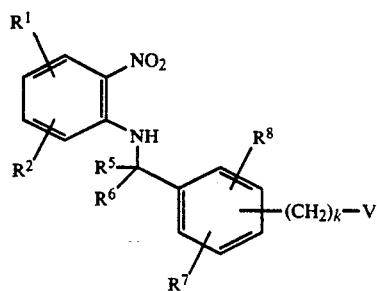  XVI wherein $R^1$, $R^2$, $R^5$, $R^6$, $R^7$, $R^8$, k and V are as in general formula I, for example in the presence of hydrogen and a catalyst such as palladium or platinum.

Amino nitrobenzenes of general formula XVI may be prepared by a number of methods. The first of these methods involves the treatment of a substituted nitrobenzene of general formula XVII

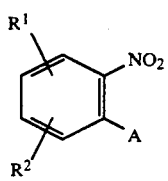  XVII wherein $R^1$ and $R^2$ are as defined in general formula I and A is halo or $C_1$–$C_4$ alkoxy; is treated with a substituted amine of general formula XVIII

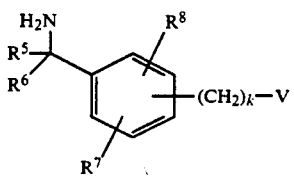  XVIII wherein $R^5$, $R^6$, $R^7$, $R^8$, k and V are as defined in general formula I. Substituted nitrobenzenes of general formula XVII are available in the art or can be prepared by methods analogous to those known in the art. Substituted amines of general formula XVIII can be prepared by procedures known to those skilled in the art.

A second procedure for the preparation of amino nitrobenzenes of general formula XVI involves the reduction of an imino nitrobenzene of general formula XIX

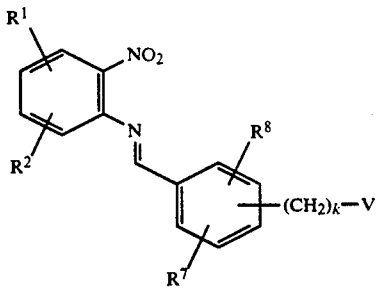

XIX wherein $R^1$, $R^2$, $R^7$, $R^8$, k and V are as defined in general formula I, for example in the presence of hydrogen and a catalyst such as palladium or platinum.

The imino nitrobenzenes of general formula XIX may be prepared by treating a substituted benzene of general formula IX with a substituted aldehyde of general formula XX

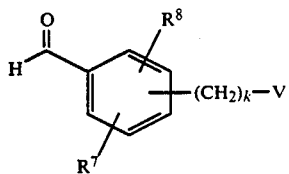

XX

Substituted aldehydes of general formula XX may be prepared by procedures known to those skilled in the art. Alternatively amino nitrobenzenes of general formula XVI may be prepared by the reduction of an amide nitrobenzene of general formula XXI

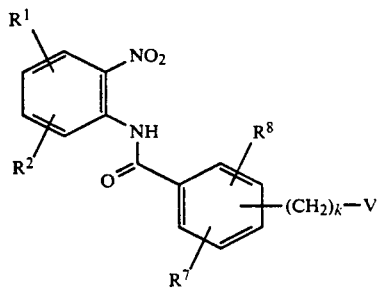

XXI wherein $R^1$, $R^2$, $R^7$, $R^8$, k and V are as defined in general formula I, with a suitable metal hydride reducing agent such as for example lithium aluminium hydride.

The amide nitrobenzenes of general formula XXI may be prepared by the coupling of a substituted benzene of general formula IX with an acid chloride of general formula XXII

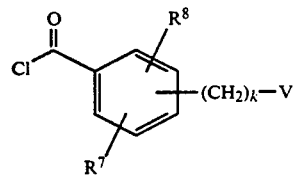

XXII wherein $R^7$, $R^8$, k and V are as defined in general formula I, in an aprotic solvent and in the presence of a suitable base such as, for example, triethylamine. Alternatively, the reaction may be conducted utilising a compound of general formula XXIII

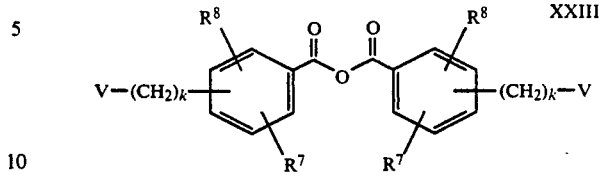

XXIII wherein $R^7$, $R^8$, k and V are as defined in general formula I. Another procedure for preparing amide nitrobenzenes of general formula XXI involves reaction of a substituted benzene of general formula IX with a compound of general formula XXIV

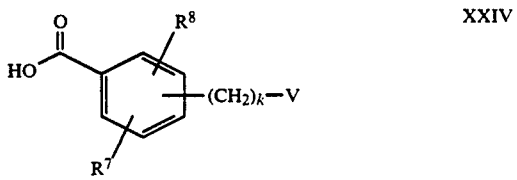

XXIV wherein $R^7$, $R^{8,}$ k and V as defined in general formula I, in the presence of a coupling reagent (e.g. 1,3-dicyclohexylcarbodiimide). Acid chlorides of general formula XXII, acid anhydrides of general formula XXIII and carboxylic acids of general formula XXIV may be prepared by procedures known to those skilled in the art.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, III and IV are valuable intermediates in the preparation of compounds of general formula I. According to a third aspect of the invention, there is therefore provided a compound of general formula II. According to a fourth aspect of the invention, there is provided a compound of general formula III. According to a fifth aspect of the invention, there is provided a compound of general formula IV.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of one or more PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a sixth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to a seventh aspect of the invention there is provided the use of a compound of general formula I in the preparation of an agent for the treatment of PAF mediated diseases; and/or for the treatment of inflammation such as rheumatoid arthritis, osteoarthritis and eye inflammation, cardiovascular disorder, thrombocytopenia, asthma, endotoxin shock, glomerulonephritis, immune regulation and psoriasis.

The compounds of general formula (I) may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to an eighth aspect of the invention there is provided a pharmaceutical or veterinary formulation comprising a compound of general formula I and a pharmaceutically and/or veterinarily acceptable carrier. One or more compounds of general formula I may be present in association with one or more non-toxic, pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared is according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or bucal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 q per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF induced functions in both the cellular and tissue levels by changing the PAF binding to its specific receptor site. The ability of compounds of general formula I to inhibit platelet aggregation in human platelet-rich plasma, and to inhibit the binding of PAF to its specific receptor binding site on human platelet plasma membranes was measured in the assay described in the pharmacology example.

The following examples illustrate the invention, but are not intended to limit the scope in any way.

The following abbreviations have been used in the Examples:
DCM—Dichloromethane
DIPE—Diisopropylether
DMF—N,N-Dimethylformamide
DPPA—Diphenyl phosphorylazide
NBS—N-Bromosuccinimide
ptlc—preparative thin layer chromatography
THF—Tetrahydrofuran

EXAMPLE 1

Ethyl 4-(1H-benzimidazylmethyl)benzoate

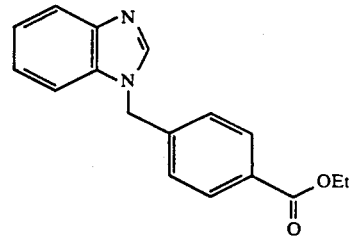

Example 1

(a) Ethyl 4-bromomethylbenzoate

To a solution of ethyl p-toluate (40.0 g, 0.24 mol) and NBS (43.44 g, 0.24 mol) in $CCl_4$ (200 ml) heated at reflux was added 2,2'-azobis(2-methylpropionitrile) (180 mg). The mixture was heated at reflux for 4 h, cooled to room temperature and stirred overnight. The white precipitate of succinimide that formed on the surface of the solution was separated and discarded. The filtrate was concentrated and crystallisation from hexane gave ethyl 4-bromomethylbenzoate (37.23 g, 63%) as an off white crystalline solid.

m.p. 34°–35° C.

i.r. (KBr) 3020, 2980, 1710 cm$^{-1}$ delta$_H$ (250 MHz, $CDCl_3$) 8.00 (2H, d, J 8.4 Hz), 7.43 (2H, d, J 8. Hz), 4.47 (2H, s), 4.35 (2H, q, J 7.1 Hz), 1.37 (3H, t, J 7.1 Hz).

(b) Ethyl 4-(1H-benzimidazylmethyl)benzoate

Sodium hydride (80% dispersion in oil) (0.61 g, 0.02 mol) was added to a stirred solution of benzimidazole (2.00 g, 0.017 mol) in dry THF (30 ml) under argon. After 90 m the mixture was cooled to 0° C. and treated with ethyl 4-bromomethylbenzoate (4.50 g, 0.019 mol) dissolved in dry THF (20 ml). The mixture was allowed to warm to ambient temperature and stirred overnight. Methanol (1 ml) was added, followed by water and the product extracted using ethyl acetate (3×75 ml). The combined organic layers were washed with water (2×50 ml), dried over $K_2CO_3$ and the solvent removed to give the crude product (4.87 g). Flash chromatography (flash silica, ethyl acetate) gave, after crystallisation from toluene, ethyl 4-[1H-benzimidazylmethyl]benzoate (1.61 g, 34%) as a white crystalline solid.

m.p. 80°–82° C.

Analysis calculated for $C_{17}H_{16}N_2O_2 \cdot 0.1H_2O$ Requires C 72.37 H 5.79 N 9.93 Found C 72.40 H 5.81 N 9.95 i.r. (nujol) 2090, 1710, 1300 cm$^{-1}$ delta$_H$(250 MHz, CDCl$_3$) 8.01 (1H, s), 7.97 (2H, d, J 6.0 Hz), 7.82 (1H, dt, J 6.0 Hz, J 1.3 Hz), 7.16–7.37 (5H, m) 5.41 (2H, s), 4.34 (2H, q, J 7.1 Hz), 1.36 (3H, t, J 7.1 Hz).

EXAMPLES 2–4

The compounds of Examples 2 to 4 were prepared by the method of Example 1 starting with the appropriate 3-substituted ethyl p-toluate.

2. Ethyl 3-bromo-4-(1H-benzimidazylmethyl)benzoate

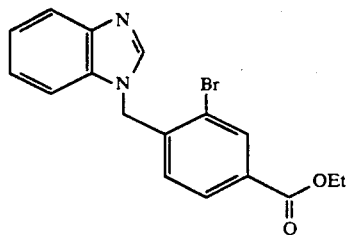

Example 2 off white crystalline solid: m.p. 103°–105° C.

Analysis calculated for $C_{17}H_{15}BrN_2O_2$ Requires C 56.84 H 4.21 N 7.80 Br 22.24 Found C 56.85 H 4.28 N 7.71 Br 22.00 i.r. (KBr) 2980, 1710, 1290 cm$^{-1}$ delta$_H$ (250 MHz, CDCl$_3$) 8.24 (1H, s), 7.93 (1H, s), 7.81 (1H, d, J 8.6 Hz), 7.67 (1H, d, J 9.3 Hz), 7.29–7.13 (3H, m), 6.71 (1H, d, J 8.1 Hz), 5.39 (2H, s), 4.31 (2H, q, J 7.1 Hz), 1.32 (3H, t, J 7.1 Hz).

3. Ethyl 3-fluoro-4-(1H-benzimidazylmethyl)benzoate

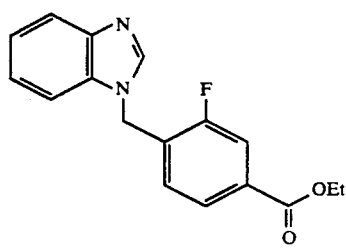

Example 3 off white crystalline solid: m.p. 99°–102° C.

Analysis calculated for $C_{17}H_{15}FN_2O_2$ Requires C 68.54 H 5.07 N 9.40 F 6.37 Found C 68.35 H 5.18 N 9.37 F 5.98 i.r. (CHCl$_3$) 2980, 1715, 1285 cm$^{-1}$ delta$_H$(250 MHz, CDCl$_3$) 7.98 (1H, s), 7.82–7.70 (3H, m), 7.29–7.24 (3H, m), 7.02 (1H, dd, J 7.8 Hz, J 7.8 Hz), 5.41 (2H, d, J 3.2 Hz), 4.34 (2H, q, J 7.1 Hz), 1.35 (3H, t, J 7.1 Hz).

4. Ethyl 3-methoxy-4-(1H-benzimidazylmethyl)benzoate

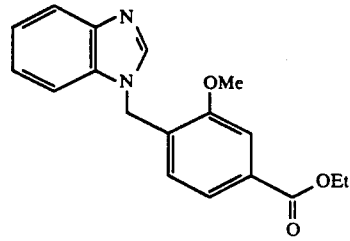

Example 4

White crystalline solid: m.p. 114°–116° C.

Analysis calculated for $C_{18}H_{18}N_2O_3$ Requires C 69.66 H 5.85 N 9.03 Found C 69.48 H 5.93 N 8.96 i.r. (CHCl$_3$) 2980, 1710, 1290 cm$^{-1}$ delta$_H$ (250 MHz, CDCl$_3$) 7.89 (1H, s,), 7.73 (1H, dd, J 6.6 Hz, J 2.2 Hz), 7.47 (1H, s), 7.45 (1H, dd, J 8.2 Hz, J 1.0 Hz), 7.25–7.10 (3H, m), 6.87 (1H, d, J 8.2 Hz), 5.22 (2H, s), 4.25 (2H, q, J 7.1 Hz), 3.80 (3H, s), 1.26 (3H, t, J 7.1 Hz).

EXAMPLE 5

(A) Ethyl 4-(1H-6-methoxybenzimidazylmethyl)benzoate and (B) Ethyl 4-(1H-5-methoxybenzimidazylmethyl)benzoate

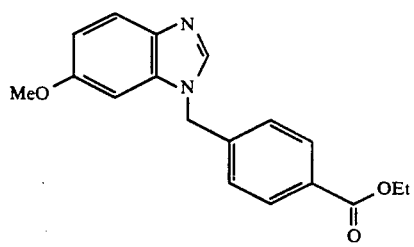

Example 5a

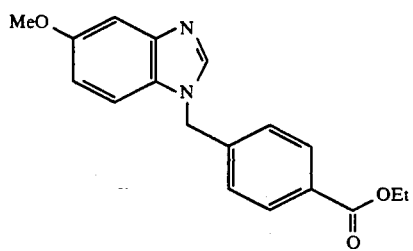

Example 5b (a) 5-Methoxybenzimidazole

4-Methoxy-1,2-phenylenediamine (5.00 g, 36 mmol) was dissolved in formic acid (10 ml) and heated at reflux for 2 hours. The solution was allowed to cool to room temperature overnight then treated with calcium carbonate (5.0 g). After dilution with ethanol (150 ml) the mixture was heated at reflux for 1 h then filtered, the residue being washed with hot ethanol (50 ml). The combined filtrates were evaporated at reduced pressure to give an oil from which a solid crystallised. The material was slurried with diethyl ether (50 ml) then filtered to give an orange solid which was recrystallised from ethyl acetate to give 5-methoxybenzimidazole (5.33 g, 99%) as a yellow crystalline solid.

m.p. 103°–105° C.

i.r. (KBr) 3090, 1390, 1290 cm$^{-1}$ delta$_H$ (250 MHz, CD$_3$OD) 8.32 (1H, s), 8.20 (1H, bs), 7.51 (1H, d, J 8.9 Hz), 7.13 (1H, d, J 2.4 Hz), 6.96 (1H, dd, J 8.9 Hz, J 2.4 Hz), 3.83,(3H, s).

(b) Ethyl 4-(1H-6-methoxybenzimidazylmethyl)benzoate and Ethyl 4-(1H-5-methoxybenzimidazylmethyl)benzoate Utilising the procedure described in Example 1(b) but employing 5-methoxybenzimidazole (1.48 g, 10.0 mmol) in lieu of benzimidazole yielded, after filtration through a pad of silica gel using chloroform as eluent, a crude product (1.83 g, 59%). Purification by column chromatography (flash silica gel, gradient elution 0–10% methanol in DCM) gave ethyl 4(1H-6-methoxybenzimidazylmethyl)benzoate (less polar isomer) as an off white crystalline solid;

m.p. 89°–91° C.

Analysis calculated for C$_{18}$H$_{18}$N$_2$O$_3$ Requires C 69.66 H 5.85 N 9.03 Found C 69.48 H 5.97 N 8.90 i.r. (KBr) 2980, 1720 cm$^{-1}$ delta$_H$ (250 MHz, CDCl$_3$) 7.94 (2H, d, J 8.5 Hz, phenyl H$_{ortho}$), 7.79 (1H, s, benzimidazole H-2), 7.65 (1H, d, J 8.8 Hz, benzimidazole H-4), 7.14 (1H, d, J 8.5 Hz, phenyl H$_{meta}$), 6.86 (1H, dd, J 8.8 Hz, J 2.4 Hz, benzimidazole H-5), 6.59 (1H, d, J 2.4 Hz, benzimidazole H-7), 5.28 (2H, s, NCH$_2$), 4.30 (2H, q, J 7.1 Hz, OCH$_2$), 3.70 (3H, s, OCH$_3$), 1.32 (3H, t, J 7.1 Hz, CH$_2$CH$_3$). In a differential NOE NMR experiment irradiation of benzylic protons (delta 5.28 ppm) showed enhancements to benzimidazole H-2 (3%), phenyl meta protons (7%) and to benzimidazole H-7 (2.5%).

and ethyl 4-(1H-5-methoxybenzimidazylmethyl) benzoate (more polar isomer) as an off white crystalline solid:

m.p. 128° C.

Analysis calculated for C$_{18}$H$_{18}$N$_2$O$_3$.0.75H$_2$O Requires C 69.26 H 5.88 N 8.97 Found C 69.17 H 5.91 N 8.96 i.r. (KBr) 2980, 1720 cm$^{-1}$ delta$_H$ (250 MHz, CDCl$_3$) 7.99 (2H, d, J 8.3 Hz, phenyl H$_{ortho}$), 7.89 (1H, s, benzimidazole H-2), 7.29 (1H, d, J 2.3 Hz, benzimidazole H-4), 7.19 (2H, d, J 8.4 Hz, phenyl H$_{para}$), 7.05 (1H, d, J 8.8 Hz, benzimidazole H-7), 6.86 (1H, dd, J 8.8 Hz, J 2.4 Hz, benzimidazole H-6), 5.35 (2H, s, NCH$_2$), 4.34 (2H, q, J 7.1 Hz, OCH$_2$), 3.83 (3H, s, OCH$_3$), 1.36 (3H, t, J 7.1 Hz, CH$_2$CH$_3$). In a differential NOE NMR experiment irradiation of benzylic protons (delta 5.35 ppm) showed enhancements to benzimidazole H-2 (4%), phenyl meta protons (4.5%) and to benzimidazole H-7 (2%).

EXAMPLE 6

Ethyl 4-(1H-5-nitrobenzimidazylmethyl)benzoate

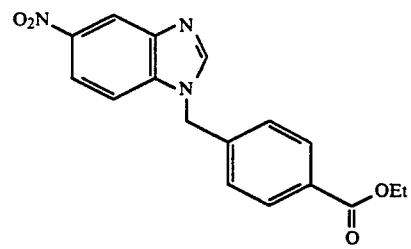

Example 6

Utilising the procedure described in Example 1(b) but employing 5-nitrobenzimidazole (3.0 g, 18.4 mmol) in lieu of benzimidazole yielded a crude product which was purified by column chromatography (flash silica gel, gradient elution 0–100% ethyl acetate in hexane) to give a 1:1 mixture of ethyl 4(1H-5-nitrobenzimidazylmethyl)benzoate and 4(1H-6-nitrobenzimidazylmethyl)benzoate (2.66 g, 44%). Repeated fractional crystalisation from methanol gave pure ethyl 4(1H-5-nitrobenzimidazylmethyl)benzoate as a white crystalline solid.

m.p. 167°–169° C.

Analysis calculated for C$_{17}$H$_{15}$N$_3$O$_4$ Requires C 62.76 H 4.65 N 12.92 Found C 62.84 H 4.77 N 12.87 i.r. (CHCl$_3$) 3010, 1715, 1525 cm$^{-1}$ delta$_H$ (250 MHz, CDCl$_3$) 8.74 (1H, d, J 1.9 Hz, benzimidazole H-4), 8.18 (1H, dd, J 9.0 Hz, J 1.9 Hz, benzimidazole H-6), 8.15 (1H, s, benzimidazole H-1), 8.04 (2H, d, J 8.2 Hz, phenyl H$_{ortho}$), 7.30 (1H, d, J 9.0 Hz, benzimidazole H-7), 7.23 (2H, d, J 8.1 Hz, phenyl H$_{meta}$), 5.49 (2H, s, NCH$_2$), 4.37 (2H, q, J 7.0 Hz, OCH$_2$), 1.37 (3H, t, J 7.0 Hz). In a differential NOE NMR experiment irradiation of benzylic protons (delta 5.49 ppm) showed enhancements to benzimidazole H-2 (2.5%), phenyl meta protons (5%) and to benzimidazole H-7 (4%).

EXAMPLE 7

N-Cyclohexyl 4-(1H-benzimidazylmethyl)benzamide

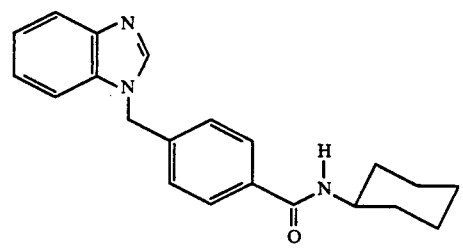

Example 7

(a) Potassium 4-(1H-benzimidazylmethyl)benzoate

To a stirred solution of ethyl 4-(benzimidazolemethyl)benzoate (1.0 g, 3.6 mmol) in ethanol (5 ml) was added a solution of 1M aqueous potassium hydroxide (3.8 ml, 3.8 mmol). The mixture was heated under reflux for 3 h. The solution was evaporated under reduced pressure, toluene (4×25 ml) was added and removed after each addition by evaporation giving the crude product. To remove any unreacted ethyl ester diethyl ether was added and the solution extracted with water (3×40 ml). The aqueous layer was then concentrated and freeze dried to yield crude potassium 4-(1H-benzimidazylmethyl)benzoate (0.49 g, 46%) as a white solid.

delta$_H$ (250 MHz, d$_6$-DMSO) 8.40-7.17 (9H, m), 5.50 (2H, s).

(b) N-Cyclohexyl 4-(1H-benzimidazylmethyl)benzamide

A stirred suspension of crude potassium 4-(1H-benzimidazylmethyl)benzoate (0.49 g, 1.7 mmol) in dry DMF (10 ml) under argon was treated with cyclohexylamine (0.2 g, 2.0 mmol) and triethylamine (0.34 g, 3.4 mmol). The solution was cooled to −5° C. and DPPA (0.53 g, 1.9 mmol) in DMF (10 ml) was added. The solution was allowed to warm to room temperature, stirred overnight and concentrated to give the crude product. Chromatography (silica gel, ethyl acetate) followed by crystallisation from toluene gave N-cyclohexyl 4-(1H-benzimidazylmethyl)benzamide (91 mg, 16%) as a white crystalline solid.

m.p. 189°-191° C.

Analysis calculated for C$_{21}$H$_{23}$N$_3$O Requires C 75.65 H 6.95 N 12.60 Found C 75.49 H 6.97 N 12.51 i.r. (KBr) 3340, 3060, 2940, 1630 cm$^{-1}$ delta$_H$ (250 MHz, CDCl$_3$) 7.95 (1H, s), 7.82 (1H, dt J 4.8 Hz, J 1.3 Hz), 7.70 (2H, d, J 7.6 Hz), 7.34-7.18 (5H, bm), 5.89 (1H, bd), 3.95 (1H, m), 2.01-1.13 (10H, bm).

EXAMPLE 8

N-Benzyl 4-(1H-benzimidazylmethyl)benzamide

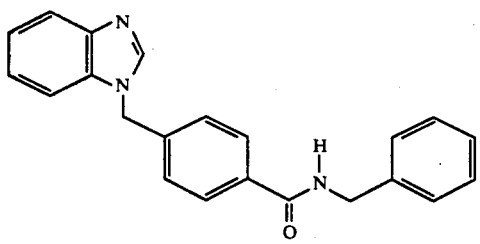

Example 8

A 2M solution of trimethylaluminium in hexane (1.05 ml, 2.1 mmol) was added to dry carbon tetrachloride (15 ml) under argon and the resulting mixture stirred and cooled to −10° C. Benzylamine (0.22 g, 2.0 mmol) was added slowly. The cooling bath was removed 20 m after the addition was completed and the mixture allowed to warm to ambient temperature over a 45 m period. A solution of ethyl 4-(1H-benzimidazylmethyl)-benzoate (0.50 g, 1.8 mmol) in dry carbon tetrachloride (10 ml) was added. The resulting solution was heated at reflux for 48 h. After cooling the mixture to ambient temperature water (0.5 ml) was added and the mixture stirred for 5 m. Aqueous 15% sodium hydroxide (1.5 ml) was added, the mixture stirred for 45 m, water (1.5 ml) added and the mixture stirred for 1 h. The granular precipitate was removed by filtration and exhaustively washed with ethyl acetate. The combined filtrates were concentrated and the residue chromatographed (flash silica gel, gradient elution 0-100% ethyl acetate in hexane) to give, after crystallisation from chloroform/hexane, N-benzyl 4-(1H-benzimidazylmethyl)benzamide (0.10 g, 16%) as a white crystalline solid.

m.p. 178°-180° C.

Analysis calculated for C$_{22}$H$_{19}$N$_3$O.0.1H$_2$O Requires C 76.99 H 5.64 N 12.22 Found C 76.89 H 5.72 N 12.22 i.r. (KBr) 3320, 3060, 2920, 1640 cm$^{-1}$ delta$_H$ (290 MHz, d$_6$- DMSO) 9.01 (1H, t, J 6.0 Hz), 7.95-6.89 (14H, bm), 5.59 (2H, s), 4.46 (2H, d, i 6.0 Hz).

EXAMPLE 9

N-Phenyl 4-(1H-benzimidazylmethyl)benzamide

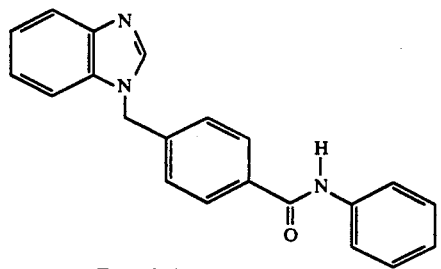

Example 9

Utilising a modification of the procedure described in Example 8 employing 4 equivalents of trimethylaluminium and 4 equivalents of aniline (0.67 g, 7.2 mmol) in lieu of benzylamine with respect to 1 equivalent of ethyl 4-(1H-benzimidazylmethyl)benzoate yielded a crude product was purified by column chromatography (flash silica gel, gradient elution 0-100% ethyl acetate in hexane) and recrystallised from methanol to give N-phenyl 4-(1H-benzimidazylmethyl)benzamide (75 mg, 13%) as a white crystalline solid.

m.p. 214°-216° C.

Analysis calculated for C$_{21}$H$_{17}$N$_3$O.0.1H$_2$O Requires C 76.62 H 5.27 N 12.76 Found C 76.54 H 5.41 N 12.79 i.r. (KBr) 3400, 3050, 2980, 1710 cm$^{-1}$ delta$_H$ (250 MHz, d$_6$-DMSO) 7.89 (2H, d, J 7.9 Hz), 7.73 (2H, d, J 7.5 Hz), 7.61 (1H; bs), 7.43 (1H, d, J 7.9 Hz), 7.39-7.00 (7H, bm), 5.61 (2H, s).

EXAMPLES 10-13

The compounds of Examples 10 to 13 were prepared by the method of Example 9 starting with the appropriate amine and reacting with trimethylaluminium and ethyl 4-(1H-benzimidazylmethyl)benzoate.

10. N-3-Chlorophenyl 4-(1H-benzimidazylmethyl)-benzamide

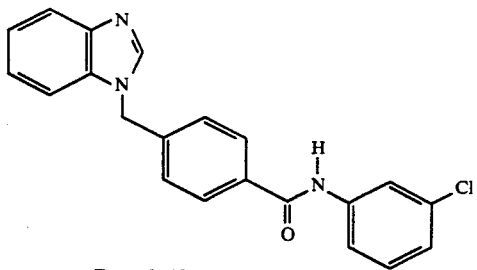

Example 10

White crystalline solid: m.p. 242°-2440° C.

Analysis calculated for C$_{21}$H$_{16}$N$_3$OCl Requires C 69.71 H 4.46 N 11.61 Cl 9.80 Found C 69.81 H 4.60 N 11.44 Cl 9.77 i.r. (KBr) 3200, 3060, 2980, 1650 cm$^{-1}$ delta$_H$ (250 MHZ, d$_6$-DMSO) 10.36 (1H, s), 8.45 (1H, s), 7.94-7.12 (12H, bm), 5.61 (2H, s).

11. N-3-methoxyphenyl 4-(1H-benzimidazylmethyl)-benzamide

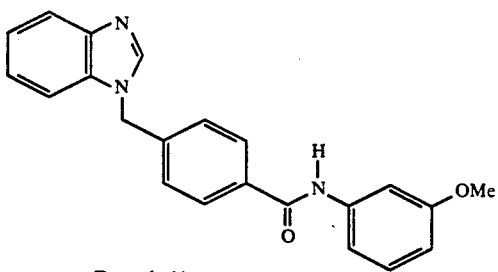

Example 11

White crystalline solid: m.p. 213°–215° C.
Analysis calculated for $C_{22}H_{19}N_3O_2.0.2\ H_2O$
Requires C 73.19 H 5.42 N 11.64 Found C 73.15 H 5.42 N 11.43
i.r. (KBr) 3360, 3040, 2980, 1660, 1300 cm$^{-1}$
$\delta_H$ (250 MHz, d$_6$-DMSO) 8.45 (1H, bs), 7.89 (2H, d, J 8.2 Hz), 7.68 (1H, bs), 7.58–7.12 (9H, bm), 6.67 (1H, dt, i 7.9 Hz, J 1.4 Hz), 5.60 (2H, s), 3.73 (3H, S).

12. N-3-Benzoxyphenyl 4-(1H-benzimidazylmethyl)-benzamide

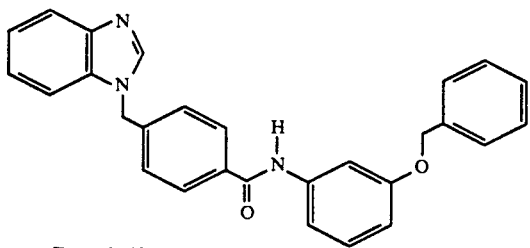

Example 12

White crystalline solid: m.p. 189°–191° C.
Analysis calculated for $C_{28}H_{23}N_3O_2$ Requires C 77.58 H 5.35 N 9.69 Found C 77.42 H 5.44 N 9.76
i.r. (KBr) 3300, 3040, 2940, 1660 cm$^{-1}$
$\delta_H$ (250 MHz, d$_6$-DMSO) 10.17 (1H, s), 8.47 (1H, s), 7.88 (2H, d, J 8.2 Hz), 7.67 (1H, bd, J 3.0 Hz), 7.63–7.17 (13H, bm), 6.75 (1H, dd, J 6.5 Hz, J 1.6 Hz), 5.54 (2H, s), 5.04 (2H, s).

13. N-Tetradecyl 4-(1H-benzimidazylmethyl)benzamide

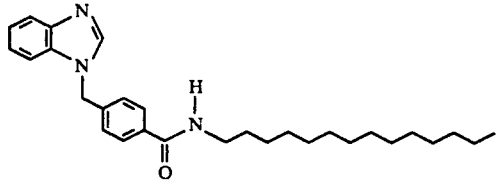

Example 13

White crystalline solid: m.p. 88°–89° C.
Analysis calculated for $C_{29}H_{41}N_3O$ Requires C 77.81 H 9.23 N 9.37 Found C 77.55 H 9.34 N 9.22
i.r. (KBr) 3350, 3060, 2920, 1680 cm$^{-1}$
$\delta_H$ (250 MHz, d$_6$-DMSO) 8.46 (1H, bs), 8.37 (1H, bt, J 5.1 Hz), 7.78 (2H, d, J 8.1 Hz), 7.68 (1H, bs), 7.49 (1H, bs), 7.36 (2H, d, J 8.0 Hz), 7.20 (2H, d, J 4.6 Hz), 5.56 (2H, s), 3.20 (2H, m), 1.48 (2H, bm), 1.23 (22H, bs), 0.85 (3H, t, J 6.4 Hz).

EXAMPLE 14

N-Cyclohexyl 3-(1H-benzimidazylmethyl)benzamide

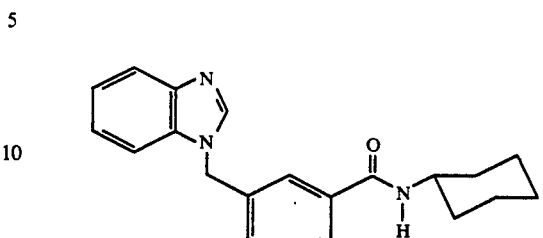

Example 14

(a) Ethyl 3-(1H-benzimidazylmethyl)benzoate
Ethyl 3-(1H-benzimidazylmethyl)benzoate was prepared by the method of Example 1 employing ethyl m-toluate in lieu of ethyl o-toluate.
White crystalline solid: m.p. 68°–70° C.
Analysis calculated for $C_{17}H_{16}N_2O_2$
Requires C 72.84 H 5.75 N 9.99 Found C 72.61 H 5.82 N 9.90
$\delta_H$ (250 MHz, CDCl$_3$) 7.90 (2H, m), 7.80 (1H, s), 7.40 (1H, m), 7.24 (4H, m), 5.40 (2H, s), 4.38 (2H, q), 1.40 (3H, t).

(b) N-Cyclohexyl 3-(1H-benzimidazylmethyl)benzamide
N-Cyclohexyl 3-(1H-benzimidazylmethyl)benzamide was prepared by the method of example 9 starting with cyclohexylamine and reacting with trimethylaluminium and ethyl 3-(1H-benzimidazylmethyl)benzoate.
White crystalline solid: m.p. 132°–134° C.
Analysis calculated for $C_{21}H_{23}N_3O.0.2H_2O$ Requires C 74.84 H 7.00 N 12.47 Found C 74.68 H 6.88 N 12.27
i.r. (KBr) 3600, 3015, 1800 cm$^{-1}$
$\delta_H$ (250 MHz, CDCl$_3$) 8.00 (1H, s), 7.85 (1H, d), 7.82 (1H, s), 7.70 (1H, d), 7.40–7.20, (5H, bm), 5.9 (1H, bs), 5.40 (2H, s) 3.95, 3.65 (1H, s), 1.8–1.0 (10H, bm).

EXAMPLE 15

N-Cyclohexyl-N-methyl 3-(1H-benzimidazylmethyl)benzamide

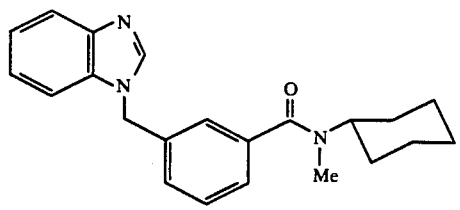

Example 15

N-Cyclohexyl-N-methyl 3-(1H-benzimidazylmethyl)benzamide was prepared by the method of Example 9 starting with N-methylcyclohexylamine and reacting with trimethylaluminium and ethyl 3-(1H-benzimidazylmethyl)benzoate.
White crystalline solid: m.p. 99°–101° C.
Analysis calculated for $C_{22}H_{225}N_3O.0.1H_2O$ Requires C 75.66 H 7.27 N 12.03 Found C 75.71 H 7.20 N 12.00
i.r. (KBr) 3050, 1660, 1420 cm$^{-1}$ delta $_H$ (250 MHz, CDCl$_3$) 8.00 (1H, s), 7.80 (1H, m), 7.25 (7H, m), 5.40 (2H, s), 5.45, 3.23 (1H, s), 2.65-2.75 (3H, s), 1.25-2.00 (10H, bm).

EXAMPLE 16

Benzoyl 4-(1H-2-methylbenzimidazylmethyl)benzene

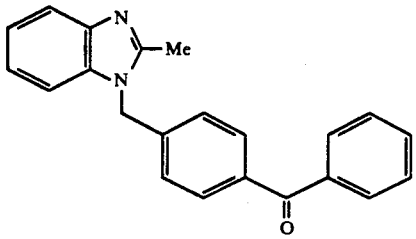

Example 16

Benzoyl 4-(1H-2-methylbenzimidazylmethyl)benzene was prepared by the method of Example 1 employing 4-methylbenzophenone in lieu of ethyl o-toluate and 2-methylbenzimidazole in lieu of benzimidazole.

Colourless crystalline solid: m.p. 119°-120° C.

Analysis calculated for C$_{22}$H$_{18}$N$_2$O

Requires C 80.96 H 5.56 N 8.58 Found C 80.71 H 5.67 N 8.61 i.r. (CHCl$_3$) 2900, 1600 cm$^{-1}$ delta$_H$ (250 MHz, CDCl$_3$) 7.80-7.11 (13H, m), 5.41 (2H, s), 2.59 (3H, s).

EXAMPLE 17

N-Cyclohexyl-N-methyl 4-(1H-benzimidazylmethyl)benzamide

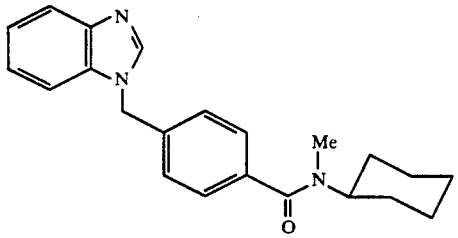

Example 17

(a) N-Cyclohexyl-N-methyl 4-methylbenzamide

To an ice cold stirred solution of N-methylcylohexylamine (20 ml, 0.15 mol) and triethylamine (22 ml) in dry THF (100 mi) under argon was slowly added p-toluoyl chloride (20 ml, 0.15 mol). A white precipitate formed. The ice bath was removed and the mixture stirred at ambient temperature for 24 h. Ice cold 2M hydrochloric acid (100 ml) was added and the organic layer separated. The aqueous layer was extracted with ethyl acetate (3×100 ml). The combined organics were washed with brine (3×100 ml), dried over Na$_2$SO$_4$, filtered and evaporated to give the crude amide, which was crystallised from hexane to give N-cyclohexyl-N-methyl 4-methylbenzamide (30.9 g, 87%) as a white crystalline solid.

m.p. 70°-71° C.

i.r. (nujol) 2920, 1640 cm$^{-1}$ delta$_H$(250 MHz, CDCl$_3$) 7.26 (2H, d, J 8.0 Hz), 7.18 (2H, d, J 8.3 Hz), 4.50, 3.50 (1H, 2bm), 3.08-2.68 (3H, bm), 2.37 (3H, s), 1.93°-0.93 (10H, bm).

(b) N-Cyclohexyl-N-methyl 4-bromomethylbenzamide

Utilising the procedure described in Example 1(a) employing N-cyclohexyl-N-methyl 4-methylbenzamide (5.0 g, 22 mmol) in lieu of ethyl 4-methylbenzoate yielded crude N-cyclohexyl-N-methyl 4-bromomethylbenzamide (4.4 g, 67%) as an orange waxy solid.

i.r. (CH$_2$Cl$_2$) 2935, 1720 cm$^{-1}$ delta$_H$ (250MHz, CDCl$_3$) 7.46 (2H, d, i 8.1 Hz), 7.34 (2H, d, J 8.1 Hz), 4.51 (2H, s), 3.78, 3.50 (1H, 2bm), 2.97 (3H, bs), 1.89-0.98 (10H, bm).

(c) N-Cyclohexyl-N-methyl 4-(1H-benzimidazylmethyl)benzamide

Utilising the procedure described in Example 1(b) employing crude N-cyclohexyl-N-methyl 4-bromomethylbenzamide (1.48 g, 5 mmol) in lieu of ethyl 4-bromomethylbenzoate yielded a crude product which was purified by column chromatography (flash silica gel, gradient elution 0-50% ethyl acetate in toluene) to yield, after crystallisation from ethyl acetate/toluene, N-cyclohexyl-N-methyl 4-(1H-benzimidazylmethyl)benzamide (0.59 g, 34%) as a white crystalline solid.

m.p. 148°-150° C.

Analysis calculated for C$_{22}$H$_{25}$N$_3$O.0.5H$_2$O

Requires C 74.13 H 7.35 N 11.79 Found C 74.23 H 7.24 N 11.68 i.r. (KBr) 2920, 1610 cm$^{-1}$ delta$_H$(250 MHz, CDCl$_3$) 7.92 (1H, s), 7.78 (1H, dt, J 6.4 Hz, J 1.9 Hz), 7.37-7.13(7H, m), 5.32 (2H, s), 4.44, 3.34 (1H, 2bm), 2.90, 2.71 (3H, 2bs), 1.92-0.89 (10H, bm).

EXAMPLE 18

N-Methyl-N-phenyl 4-(1H-benzimidazylmethyl)benzamide

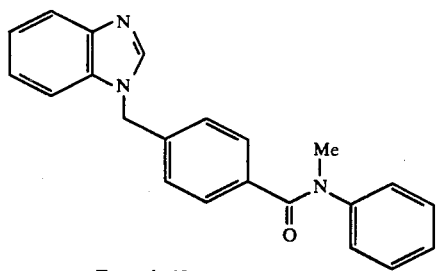

Example 18

N-Methyl-N-phenyl 4-(1H-benzimidazylmethyl)benzamide was prepared by the method of Example 17 employing N-methylaniline in lieu of N-methylcyclohexylamine.

White crystalline solid: 211°-213° C.

Analysis calculated for C$_{22}$H$_{19}$N$_3$0.0.1 Requires C 76.99 H 5.64 N 12.24 Found C 76.85 H 5.68 N 12.23 i.r. (CHCl$_3$):2970, 1640 cm$^{-1}$ delta$_H$(250 MHz, CDCl$_3$) 7.86 (1H, s), 7.81 (1H, d, J 7.2 Hz), 7.31-7.10 (8H, m), 7.05-6.95 (4H, m), 5.28 (2H, s), 3.49 (3H, S).

EXAMPLE 19

N-Cyclohexyl-N-ethyl 4-(1H-benzimidazylmethyl)benzamide

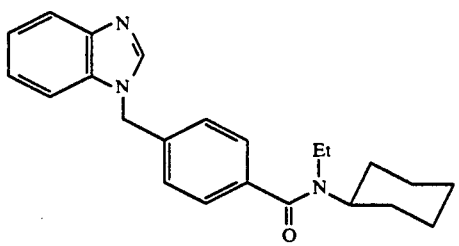

Example 19

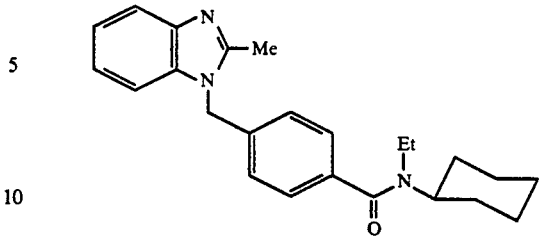

Example 21

N-Cyclohexyl-N-ethyl 4-(1H-benzimidazylmethyl)-benzamide was prepared by the method of Example 9 starting with N-ethylcyclohexylamine and reacting with trimethylaluminium and ethyl 4-(1H-benzimidazylmethyl)benzoate.

White crystalline solid: m.p. 118°–119° C.

Analysis calculated for $C_{22}H_{27}N_3O$ Requires C 76.42 H 7.53 N 11.62 Found C 76.34 H 7.61 N 11.33 i.r. (KBr) 3080, 2940, 1660 cm$^{-1}$ delta $_H$(250 MHz, CDCl$_3$) 7.96 (1H, s), 7.82 (1H, m), 7.34–7.11 (7H, bm), 5.38 (2H, s), 3.40 (2H, bm), 4.30, 3.17 (1H, 2bm), 1.92 (13H, bm).

EXAMPLE 20

N-Cyclohexyl-N-methyl 4-(1H-2-methylbenzimidazylmethyl)benzamide

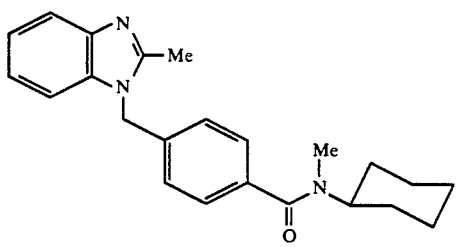

Example 20

N-Cyclohexyl-N-methyl 4-(1H-2-methylbenzimidazylmethyl)benzamide was prepared by the method of Example 17(c) employing 2-methylbenzimidazole in lieu of benzimidazole.

White crystalline solid: m.p. 157°–160° C.

Analysis calculated for $C_{23}H_{27}N_3O \cdot 0.1H_2O$ Requires C 76.04 H 7.55 N 11.57 Found C 75.83 H 7.53 N 11.41 i.r. (nujol) 2920, 1620 cm$^{-1}$ delta$_H$ (250 MHz, CDCl$_3$) 7.78 (1H, d, J 7.0 Hz), 7.38–7.12 (7H, m), 5.37 (2H, s), 4.46, 3.38 (1H, 2bm), 2.98, 2.78 (3H, 2bs), 2.59 (3H, s), 1.90–0.95 (10H, bm).

EXAMPLE 21

N-Cyclohexyl-N-ethyl 4-(1H-2-methylbenzimidazylmethyl)benzamide

N-Cyclohexyl-N-ethyl 4-(1H-2-methylbenzimidazylmethyl)benzamide was prepared by the method of Example 17 employing N-ethylcyclohexylamine in lieu of N-methylcyclohexylamine and 2-methylbenzimidazole in lieu of benzimidazole.

Off white crystalline solid: m.p. 158°–160° C.

Analysis calculated for $C_{24}H_{29}N_3O$ Requires C 76.77 H 7.78 N 11.19 Found C 76.54 H 7.86 N 11.12 i.r. (CHCl$_3$) 2930, 1600 cm$^{-1}$ delta$_H$ (250 MHz, CDCl$_3$) 7.74 (1H, d, J 7 Hz), 7.33–7.18 (5H, m), 7.06 (2H, d, J 7 Hz), 5.33 (2H, s), 4.30, 3.38, 3.18 (3H, bm and 2bs), 2.58 (3H, s), 1.88–0.86 (13H, m).

EXAMPLE 22

N,N-Dicyclohexyl 4-(1H-2-methylbenzimidazylmethyl)benzamide

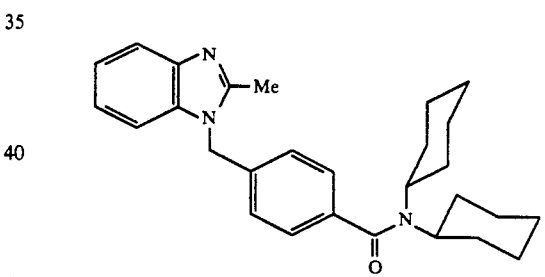

Example 22

N,N-Dicyclohexyl 4-(1H-2-methylbenzimidazylmethyl)benzamide was prepared by the method of Example 9 starting with dicyclohexylamine and reacting with trimethylaluminium and ethyl 4-(1H-2-methylbenzimidazylmethyl)benzoate.

White crystalline solid: m.p. 177°–179° C.

Analysis calculated for $C_{28}H_{35}N_3O \cdot 0.2H_2O$ Requires C 77.63 H 8.24 N 9.70 Found C 77.74 H 7.99 N 10.35 i.r. (KBr) 1625 cm$^{-1}$ delta$_H$ (250 MHz, CDCl$_3$) 7.76–7.66 (1H, m), 7.29 to 7.03 (7H, m), 5.34 (2H, s), 3.12 (2H, bs), 2.57 (3H, s), 2.04–1.13 (20H, bm).

EXAMPLES 23–26

The compounds of Examples 23 to 26 were prepared by the method of Example 17(c) starting from the appropriate 2-substituted benzimidazole.

23. N-Cyclohexyl-N-methyl 4-(1H-2-ethylbenzimidazylmethyl)benzamide

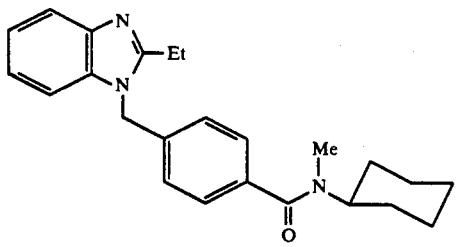

Example 23

White amorphous solid.
Analysis calculated for $C_{24}H_{29}N_3O.H_2O$ Requires C 74.97 H 7.87 N 10.93 Found C 75.05 H 7.80 N 10.73
i.r. (KBr) 2920, 1640 cm$^{-1}$
$delta_H$ (250 MHz, d$_6$-DMSO) 7.80 (1H, d, J 6.5 Hz), 7.37–7.02 (7H, m), 5.38 (2H, s), 4.42, 3.40 (1H, 2bm), 2.96, 2.77 (3H, 2bs), 2.82 (2H, q, J 8 Hz), 1.44 (3H, t, J 8 Hz), 1.94–0.98 (10H, bm).

24. N-Cyclohexyl-N-methyl 4-(1H-2-isopropylbenzimidazylmethyl) benzamide

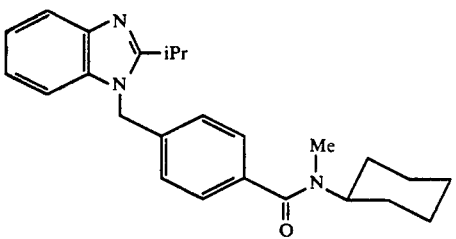

Example 24

White crystalline solid: m.p. 54°–56° C.
Analysis calculated for $C_{25}H_{31}N_3O.0.8H_2O$ Requires C 74.00 H 8.14 N 10.36 Found C 74.01 H 7.81 N 10.18
i.r. (nujol) 2920, 1640 cm$^{-1}$
$delta_H$ (250 MHz, CDCl$_3$) 7.80 (1H, d, J 7 Hz), 7.34–6.98 (7H, m), 5.40 (2H, s), 4.44, 3.38 (1H, 2bm), 3.10 (1H, m), 2.92, 2.76 (3H, 2bs), 1.88–0.98 (10H, bm), 1.40 (6H, d, J 8 Hz).

25. N-Cyclohexyl-N-methyl 4-(1H-2-tert-butylbenzimidazylmethyl) benzamide

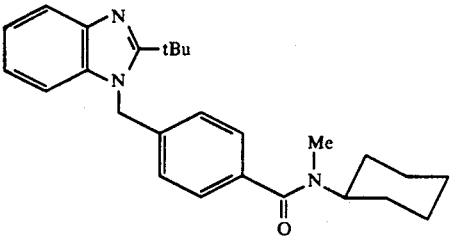

Example 25

Yellow crystalline solid: m.p. 102°–105° C.
Analysis calculated for $C_{26}H_{33}N_3O.0.4H_2O$ Requires C 76.02 H 8.29 N 10.23 Found C 76.17 H 8.35 N 10.02
i.r. (nujol) 2920, 1630 cm$^{-1}$
$delta_H$ (250 MHz, CDCl$_3$) 7.82 (1H, d, J 9 Hz), 7.32–6.94 (7H, m), 5.62 (2H, s), 4.42, 3.38 (1H, 2bm), 2.98, 2.80 (3H, 2bs), 1.90–0.98 (10H, bm), 1.54 (9H, s).

26. N-Cyclohexyl-N-methyl 4-(1H-2-thiomethylbenzimidazylmethyl) benzamide

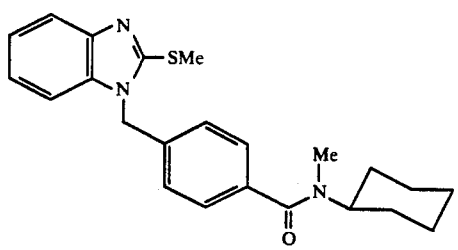

Example 26

White crystalline solid: m.p. 115°–118° C.
Analysis calculated for $C_{23}H_{27}N_3OS.0.2H_2O$ Requires C 69.56 H 6.95 N 10.58 Found C 69.64 H 6.91 N 10.43
i.r. (nujol) 2920, 1610 cm$^{-1}$
$delta_H$ (250 MHz, CDCl$_3$) 7.74 (1H, d, J 8 Hz), 7.38–7.16 (7H, M), 5 (2H, s), 4.46, 3.42 (1H, 2bm), 2.98, 2.78 (3H, 2bs), 2.81 (3H, s), 1.90–0.96 (10H, bm).

EXAMPLE 27

N-Cyclohexyl-N-methyl 4-(1H-2-methylsulphinylbenzimidazylmethyl) benzamide

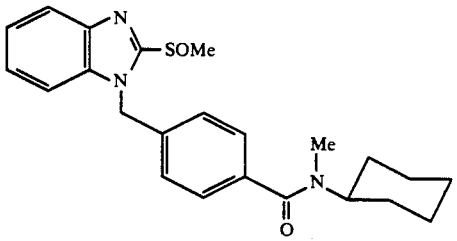

Example 27

N-Cyclohexyl-N-methyl 4-(1H-2-thiomethylbenzimidazylmethyl)benzamide (393 mg, 1 mmol) was dissolved in 20 ml methanol and metachloroperbenzoic acid (190 mg, 1.1 mmol) was added over 2 minutes. The mixture was left to stir at room temperature for 2 hours and then partitioned between ethyl acetate (100 ml) and saturated sodium bicarbonate solution (200 ml). The organic layer was dried (Na$_2$SO$_4$ filtered and concentrated to give the crude product as a solid. Recrystallisation from hot DIPE gave N-cyclohexyl-N-methyl 4-(1H-2-methylsulphinylbenzimidazylmethyl)benzamide (250 mg, 61%) as a white crystalline solid.
m.p. 142°–143° C.
Analysis calculated for $C_{23}H_{27}N_3O_2S$ Requires C 67.45 H 6.65 N 10.26 Found C 67.32 H 6.71 N 10.01
i.r (KBr) 2950, 1630, 1310 cm$^{-1}$
$delta_H$ (250 MHz, d$_6$-DMSO) 7.82 (1H, m), 7.40–7.20 (7H, m), 5.82 (2H, s), 4.42, 3.40 (1H, 2bm), 3.21 (3H, s), 2.96, 2.77 (3H, 2bs), 1.95–0.96 (10H, bm).

EXAMPLE 28

N-Cyclohexyl-N-methyl 4-(1H-2-methylaulphonylbenzimidazylmethyl) benzamide

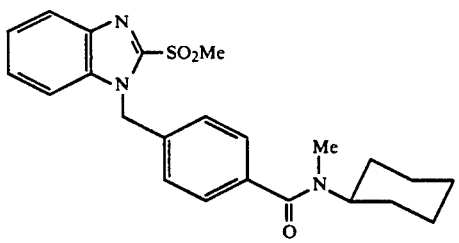

Example 28

Utilising the above procedure employing N-cyclohexyl-N-methyl 4-(1H-2-thiomethylbenzimidazylmethyl)benzamide (393 mg, 1 mmol) was dissolved in methanol (20 ml) and reacted with metachloroperbenzoic acid (688/mg, 4 mmol). The product was purified by column chromatography (flash silica, ethyl acetate) and crystallised from diisopropyl ether-hexane to give N-cyclohexyl-N-methyl 4-(1H-2-methylsulphonylbenzimidazylmethyl)benzamide (100 mg, 24%) as a white crystalline solid.

m.p. 185°–186° C.

Analysis calculated for $C_{23}H_{27}N_3O_3S$ Requires C 64.92 H 6.40 N 9.87 Found C 64.72 H 6.41 N 9.87 i.r. (KBr) 3040, 2920, 1620, 1320, 1140 cm$^{-1}$ delta$_H$ (250 MHz, d$_6$-DMSO) 7.92–7.83 (1H, m), 7.42–7.18 (7H, m), 5.82 (2H, s), 4.42, 3.38 (1H, 2bm), 3.50 (3H, s), 2.96, 2.76 (3H, 2bs), 1.90–0.98 (10H, bm).

EXAMPLE 29

N-Cyclohexyl-N-methyl 4-(1H-2-(2-thiomethylethyl)benzimidazylmethyl)benzamide

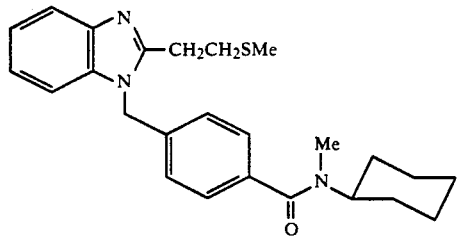

Example 29

(a) 2-(2-Thiomethylethyl)benzimidazole n-Butyllithium (16.4 ml of 2.5 M solution in hexane) was added to a stirred solution of 2-methylbenzimidazole (2.60 g, 20 mmol) in dry THF (120 ml) at 0° C. under argon. The resulting mixture was allowed to warm up to ambient temperature and stirred for 0.5 h before cooling to −200° C. A solution of chlorothiomethyl ether (1.93 g, 20 mmol) in dry THF (20 ml) was added dropwise and the mixture allowed to slowly warm to ambient temperature and was stirred overnight. Aqueous ammonia (2 ml. 0.88M) was added and the mixture stirred for 2 h. The reaction mixture was partitioned between ethyl acetate and brine, the organic layer separated and dried (Na$_2$SO$_4$). The product was purified by column chromatography mash silica gel, ethyl acetate) followed by crystallisation from ethyl acetate/hexane to give 2-(2-thiomethylethyl)benzimidazole (0.22 g, 6%) as a yellow crystalline solid.

m.p. 156°–158° C.

delta$_H$ (250 MHz, CDCl$_3$) 7.78–7.22 (4H, 2bm), 3.22 (2H, t, J 8 Hz), 3.00 (2H, t, J 8 Hz), 2.18 (3H, s).

(b) N-Cyclohexyl-N-methyl 4-(1H-2-(2-thiomethylethyl)benzimidazylmethyl)benzamide Utilising the procedure described in Example 17(c) employing 2-(2-thiomethylethyl)benzimidazole (259 mg, 1.35 mmol) in lieu of benzimidazole gave a crude product which was purified by column chromatography (flash silica gel, ethyl acetate) to yield N-cyclohexyl-N-methyl 4-(1H-2-(2-thiomethylethyl)benzimidazylmethyl)benzamide (100 mg, 18%) as a yellow gum.

Analysis calculated for $C_{25}H_{31}N_3OS.0.5H_2O$ Requires C 69.73 H 7.49 N 9.76 Found C 69.87 H 7.38 N 9.61 i.r. (neat) 2920, 1610 cm$^{-1}$ delta$_H$ (250 MHz, CDCl$_3$) 7.78 (1H, d, i 8 Hz), 7.36–7.02 (7H, m), 5.42 (2H, s), 4.44, 3.38 (1H, 2bm), 3.18–2.96 (4H, m), 2.94, 2.76 (3H, 2bs), 2.12 (3H, s), 1.94–1.00 (10H, bm).

EXAMPLES 30–34

The compounds of Examples 30 to 34 were prepared by the method of Example 17(c) starting from the appropriate substituted benzimidazole.

30. N-Cyclohexyl-N-methyl 4-(1H-2-trifluoromethylbenzimidazylmethyl) benzamide

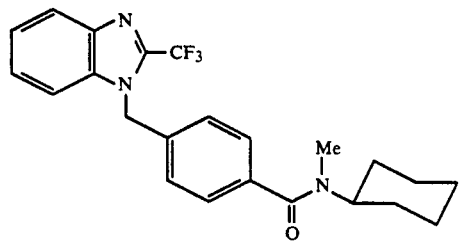

Example 30

Off white crystalline solid: m.p. 168°–171° C.

Analysis calculated for $C_{23}H_{24}F_3N_3O$ Requires C 66.49 H 5.82 N 10.11 Found C 66.13 H 5.92 N 9.80 i.r. (nujol) 2915, 1620 cm$^{-1}$ delta$_H$ (250 MHz, CDCl$_3$) 7.94 (1H, m), 7.42–7.04 (7H, m), 4.46, 3.38 (1H, 2bm), 3.00, 2.88 (3H, 2bs), 1.88–0.96 (10H, bm).

31. N-Cyclohexyl-N-methyl 4-(1H-2-(4-thiazolyl)-benzimidazylmethyl) benzamide

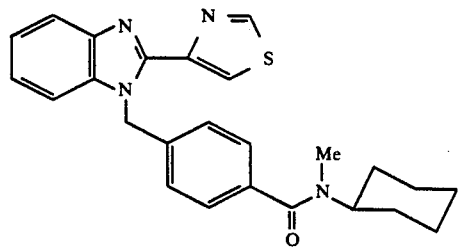

Example 31

White crystalline solid: m.p. 143°–145° C.

Analysis calculated for $C_{25}H_{26}N_4OS.0.2H_2O$ Requires C 69.16 H 6.13 N 12.90 Found C 69.26 H 6.11 N 13.00 i.r. (nujol) 2915, 1620 cm$^{-1}$ delta$_H$ (250 MHz, CDCl$_3$) 8.90 (1H, s), 8.38 (1H, s), 7.82 (1H, d, J 8 Hz), 7.40-7.12 (7H, m), 6.12 (2H, s), 4.46, 3.40 (1H, 2bm), 2.98, 2.74 (3H, 2bs), 1.94-0.94 (10H, bm).

32. N-Cyclohexyl-N-methyl 4-(1H-2-phenylbenzimidazylmethyl)benzamide

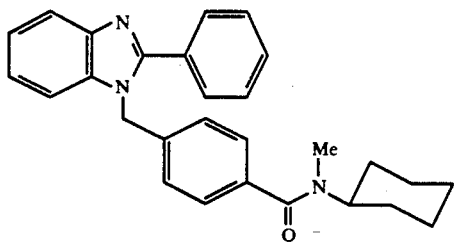

Example 32

White crystalline solid: m.p. 154°-156° C.

Analysis calculated for C$_{28}$H$_{29}$N$_3$O.0.2H$_2$O Requires C 78.73 H 6.94 N 9.84 Found C 78.50 H 6.91 N 9.65
i.r. (nujol) 2920, 1615 cm$^{-1}$ delta$_H$ (250 MHz, CDCl$_3$) 7.91 (1H, d, J 7 Hz), 7.70-7.08 (12H, m), 5.46 (2H, s), 4.52, 3.42 (1H, 2bm), 3.00, 2.82 (3H, 2bs), 1.94-1.02 (10H, bm).

33. N-Cyclohexyl-N-methyl 4-(1H-2-(2-chlorophenyl)benzimidazylmethyl) benzamide

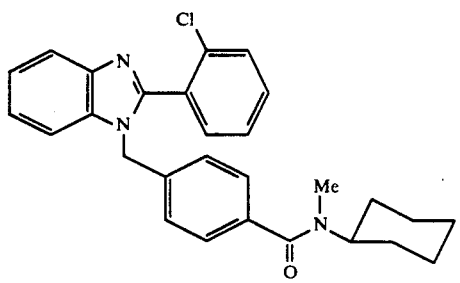

Example 33

White crystalline solid: m.p. 93°-950° C.

Analysis calculated for C$_{28}$H$_{28}$N$_3$OCl.1.0.CCl$_4$ Requires C 71.30 H 5.96 N 8.88 Found C 71.45 H 6.11 N 8.79
i.r. (CH$_2$Cl$_2$) 2930, 1620 cm$^{-1}$ delta$_H$ (250 MHZ, CDCl$_3$) 7.87 (1H, d,), 7.55-7.18 (9H, m), 6.98 (2H, d, J 8.1 Hz), 5.28 (2H, s), 4.48, 3.33, (1H, 2bm), 2.92, 2.72 (3H, 2bs), 1.91-0.90 (10H, bm).

34. N-Cyclohexyl-N-methyl 4-(1H-5,6-dimethylbenzimidazylmethyl) benzamide

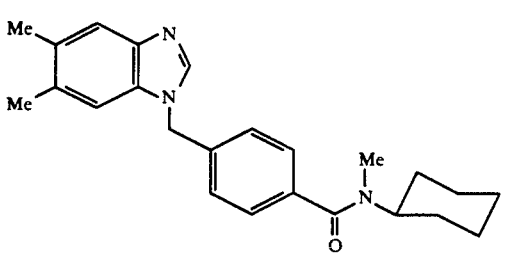

Example 34

White crystalline solid: m.p.177°-178° C.

Analysis calculated for C$_{24}$H$_{29}$N$_3$O.0.2H$_2$O Requires C 76.04 H 7.82 N 11.08 Found C 76.18 H 7.75 N 11.09
i.r. (CHCl$_3$) 2930, 1620 cm$^{-1}$ delta$_H$ (250 MHz, CDCl$_3$) 7.85 (1H, s), 7.58 (1H, s), 7.32 (2H, d, J 7.9 Hz), 7.16 (2H, d, J 8.1 Hz), 7.01 (1H, s), 5.33 (2H, s), 4.49, 3.38 (1H, 2bm), 2.90-2.75 (3H, 2bs), 2.36 (3H, s), 2.32 (3H, s), 1.90-0-95 (10H, bm).

EXAMPLES 35-37

The compounds of Examples 35 to 37 were prepared by the method of Example 9 starting with N-methylcyclohexylamine and reacting with trimethylamine and the appropriately substituted ethyl 4-(1H-benzimidazylmethyl)benzoate derivative.

35. N-Cyclohexyl-N-methyl 3-bromo-4-(1H-2-benzimidazylmethyl)benzamide

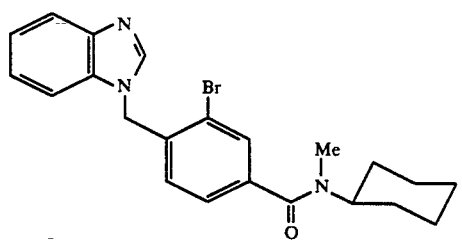

Example 35

Off white crystalline solid: m.p. 140°-142° C.

Analysis calculated for C$_{22}$H$_{24}$N$_3$OBr Requires C 61.98 H 5.67 N 9.86 Found C 61.92 H 5.52 N 10.79
i.r. (KBr) 3050, 1625, 750 cm$^{-1}$ delta$_H$ (250 MHz, CDCl$_3$) 7.90 (2H, m), 7.65 (1H, s), 7.30 (4H, m), 6.75 (1H, d), 5.45 (2H, s), 4.45, 3.35 (1H, 2bm), 2.85 (3H, 2bs), 1.40 (10H, m).

36. N-Cyclohexyl-N-methyl 3-fluoro-4-(1H-2-benzimidazylmethyl) benzamide

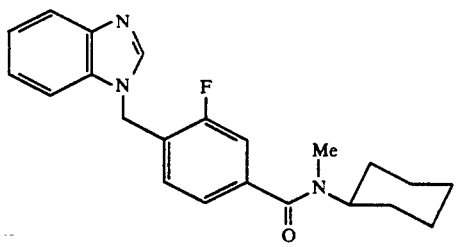

Example 36

White crystalline solid: m.p. 98°-100° C.

Analysis calculated for C$_{22}$H$_{24}$N$_3$OF.0.2H$_2$O Requires C 71.60 H 6.66 N 11.39 Found C 71.46 H 6.65 N 11.17 delta$_H$ (250 MHz, CDCl$_3$) 8.00 (1H, s), 7.82 (1H, m), 7.30 (3H, m), 7.10 (3H, m), 5.40 (2H, s), 4.40, 3.80 (1H, 2bm), 2.83 (3H, 2bs), 2.00-1.00 (10H, m).

37. N-Cyclohexyl-N-methyl 3-methoxy-4-(1H-2-benzimidazylmethyl) benzamide

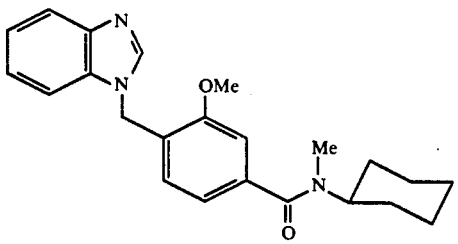

Example 37

White crystalline solid: m.p. 169°–171° C.

Analysis calculated for $C_{23}H_{27}N_3O_2.0.1H_2O$ Requires C 69.85 H 7.39 N 10.62 Found C 69:92 H 7.39 N 10.36

$delta_H$ (250 MHz, CDCl$_3$) 8.00 (1H, s), 7.80 (H, m), 7.35 (1H, m), 7.25 (2H, m), 6.95 (2H, m), 6.25 (1H, m), 5.35 (2H, s), 4.25, 3.25 (1H, 2bm), 3.90 (3H, s), 2.85 (3H, 2bs), 1.50 (10H, m).

EXAMPLE 38

N-Cyclohexyl 4-(1H-benzimidazylmethyl)benzenesulphonamide

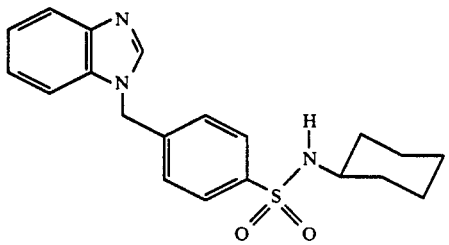

Example 38

(a) N-Cyclohexyl 4-methylbenzenesulphonamide

Utilising the procedure described in Example 17(a) but employing p-toluenegulphonyl chloride (33.0 g, 0.17 mol) in lieu of p-toluoyl chloride and cyclohexylamine (20.0 ml, 0.17 mol) in lieu of N-methylcyclohexylamine, yielded a crude product which was crystallised from hexane/ethyl acetate to give N-cyclohexyl 4-methylbenzenesulphonamide (35.0 g, 79%) as a white crystalline solid.

m.p. 91°–92° C.

i.r. (CH$_2$Cl$_2$) 3380, 3280, 2935, 1325, 1160 cm$^{-1}$ $delta_H$ (250 MHz, CDCl$_3$) 7.77 (2H, d, J 8.3 Hz), 7.30 (2H, d, J 8.2 Hz), 4.39 (1H, d, J 7.5 Hz), 3.14 (1H, m), 2.34 (3H, s), 1.83–1.05 (10H, m).

(b) N-Cyclohexyl 4-bromomethylbenzenesulphonamide

Utilising the procedure described in Example 1(a) employing N-cyclohexyl 4-methylbenzenesulphonamide (24.3 g, 0.096 mol) in lieu of ethyl 4-methylbenzoate yielded crude N-cyclohexyl 4-bromomethylbenzenesulphonamide (4.2 g, 13%) as a pale yellow waxy solid.

i.r. (CH$_2$Cl$_2$) 3380, 3280, 2935, 1325, 1160 cm$^{-1}$ $delta_H$ (250 MHz, CDCl$_3$) 7.85 (2H, d, J 8.3 Hz), 7.53 (2H, d, J 8.3 Hz), 4.80 (1H, d, J 7.5 Hz), 4.50 (2H, 1.90–0.83 (10H, m).

(c) N-Cyclohexyl 4-(1H-benzimidazylmethyl)benzenesulphonamide

Utilising the procedure described in Example 1(b) employing crude N-cyclohexyl 4-bromomethylbenzenesulphonamide (2.9 g, 8.7 mmol) in lieu of ethyl 4-bromomethylbenzoate yielded a crude product which was purified by column chromatography (flash silica gel, gradient elution 0–100% ethyl acetate in hexane) followed by crystallisation from acetone to give N-cyclohexyl 4-(1H-benzimidazylmethyl) benzenesulphonamide (0.47 g, 15%) as a white crystalline solid.

m.p. 192°–193° C.

Analysis calculated for $C_{20}H_{23}N_3O_2S.0.4H_2O$ Requires C 63.77 H 6.37 N 11.15 Found C 63.59 H 6.20 N 10.95 i.r. (CH$_2$Cl$_2$) 3370, 2940, 1330, 1160 cm$^{-1}$ $delta_H$ (250 MHz, CDCl$_3$) 8.00 (1H, s), 7.85 (3H, m), 7.35–7.20 (5H, m), 5.46 (2H, S), 4.39 (1H, d, J 7.7 Hz), 3.15 (1H, m), 1.82–1.05 (10H, m).

EXAMPLE 39

N-Cyclohexyl 4-(1H-2-methylbenzimidazylmethyl)benzenesulphonamide

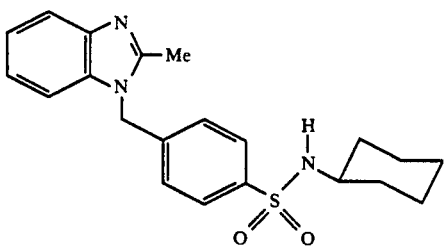

Example 39

N-Cyclohexyl 4-(1H-2-methylbenzimidazylmethyl)benzenesulphonamide was prepared by the method of 38(c) employing 2-methylbenzimidazole in lieu of benzimidazole.

White crystalline solid: m.p. 185°–1870° C.

Analysis calculated for $C_{21}H_{25}N_3SO_2.0.3H_2O$ Requires C 64.85 H 6.63 N 10.80 Found C 64.92 H 6.49 N 10.76 i.r. (KBr) 3420, 1320, 1160 cm$^{-1}$ $delta_H$ (250 MHz, (CDCl$_3$) 7.81–7.71 (3H, m), 7.28–7.13 (5H, m), 5.37 (2H, s), 4.72 (1H, d, J 7.6 Hz), 3.11 (1H, bs), 2.55 (3H, s), 1.86–1.05 (10H, bm).

EXAMPLE 40

N-Cyclohexyl-N-methyl.4-(1H-benzimidazylmethyl)benzenesulphonamide

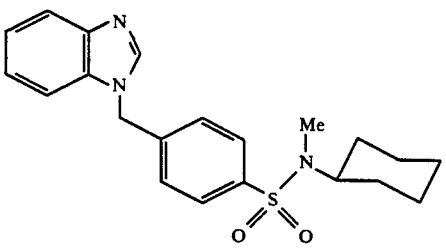

Example 40

(a) N-Cyclohexyl-N-methyl 4-methylbenzenesulphonamide

Utilising the procedure described in Example 10(a) but employing p-toluenesulphonyl chloride (58.0 g, 0.30 mol) in lieu of p-toluoyl chloride yielded a crude product which was crystallised from hexane/ethyl acetate to give N-cyclohexyl 4-methylbenzenesulphonamide (68.4 g, 82%) as a white crystalline solid.

m.p. 83°-84° C.

i.r. (CH$_2$Cl$_2$) 2935, 1330, 1150 cm$^{-1}$ delta$_H$ (250 MHz, CDCl$_3$) 7.70 (2H, d, J 8.3 Hz), 7.29 (2H, d, J 8.6 Hz), 3.77 (1H, m), 2.73 (3H, s), 2.42 (3H, s), 1.68–0.78 (10H, m).

(b) N-Cyclohexyl-N-methyl 4-bromomethylbenzenesulphonamide

Utilising the procedure described in Example 1(a) employing N-cyclohexyl-N-methyl 4-methylbenzenesulphonamide (20.0 g, 0.075 mol) in lieu of ethyl 4-methylbenzoate and two equivalents of NBS (27.0 g, 0.15 mol) yielded a crude product of N-cyclohexyl-N-methyl 4-bromomethylbenzenesulphonamide (23.4 g, 90%) as an orange oil.

i.r. (neat) 2935, 1330, 1150 cm$^{-1}$ delta$_H$ (250 MHz, CDCl$_3$) 7.78 (2H, d, J 8.3Hz), 7.50 (2H, d, J 8.3 Hz), 4.49 (2H, s), 3.78 (1H, M), 2.75 (34 s), 1.83–0.93 (10H, bm).

(c) N-Cyclohexyl-N-methyl 4-(1H-benzimidazylmethyl)benzenesulphonamide

Utilising the procedure described in Example 1(b) employing crude N-cyclohexyl-N-methyl 4-bromomethylbenzenesulphonamide (8.0 g, 23 mmol) in lieu of ethyl 4-bromomethylbenzoate yielded a crude product a portion of which was purified by column chromatography (flash silica gel, gradient elution 0–100% ethyl acetate in hexane) followed by ptlc (silica gel, ethyl acetate) and crystallisation from ethyl acetate/hexane to give N-cyclohexyl-N-methyl 4-(1H-benzimidazylmethyl)benzenesulphonamide (0.21 g, 3%) as a white crystalline solid.

m.p. 191°–193° C.

Analysis calculated for C$_{21}$H$_{25}$N$_3$SO$_2$.0.8H$_2$O Requires C 63.39 H 6.74 N 10.56 Found C 63.16 H 6.35 N 10.50 i.r. (CH$_2$Cl$_2$) 2935, 1330, 1150 cm$^{-1}$ delta$_H$ (250 MHz, CDCl$_3$) 7.85 (1H, s), 7.72 (1H, dd, J 6.7 Hz, J 1.6 Hz), 7.63 (2H, d, J 8.3 Hz), 7.25–7.05 (5H, m), 5.30 (2H, s), 3.60 (1H, m), 2.59 (3H, s), 1.93–0.78 (10H, bm).

EXAMPLES 41–48

The compounds of Examples 41 to 48 were prepared by the method of Example 40(c) starting from the appropriate substituted benzimidazole.

41. N-Cyclohexyl-N-methyl 4-(1H-2-methylbenzimidazylmethyl) benzenesulphonamide

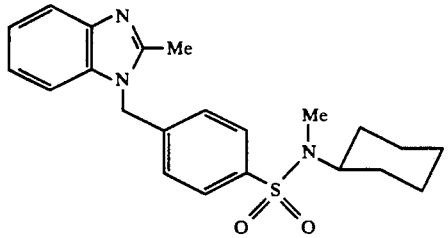

Example 41

Colourless viscous oil.

Analysis calculated for C$_{22}$H$_{27}$N$_3$SO$_2$.0.7H$_2$O Requires C 64.43 H 6.98 N 10.24 Found C 64.36 H 6.65 N 10.27 i.r. (CH$_2$Cl$_2$) 2935, 1330, 1150 cm$^{-1}$ delta$_H$ (250 MHz, CDCl$_3$) 7.85–7.74 (3H, m), 7.33–7.15 (5H, m), 5.39 (2H, s), 3.75 (1H, m), 2.72 (3H, s), 2.56 (3H, s), 1.81–0.93 (10H, bm).

42. N-Cyclohexyl-N-methyl 4-(1H-2-ethylbenzimidazylmethyl) benzenesulphonamide

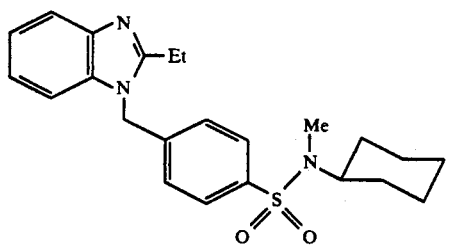

Example 42

White amorphous solid: m.p. 54°–57° C.

Analysis calculated for C$_{23}$H$_{29}$N$_3$OS.0.4H$_2$O Requires C 65.97 H 7.17 N 10.03 Found C 65.95 H 7.01 N 10.01 i.r. (CH$_2$Cl$_2$) 2940, 1330, 1150 cm$^{-1}$ delta$_H$ (250 MHz, CDCl$_3$) 7.79 (1H, d, J 8.5 Hz), 7.7., (2H, d, J 8.3 Hz), 7.31–7.20 (3H, m), 7.16 (2H, d, J 8.4 Hz), 5.40 (2H, s), 3.72 (1H, bm), 2.84 (2H, q, J 7.5 Hz), 2.72 (3H, s), 1.80–0.90 (10H, bm), 1.41 (3H, to J 7.5 Hz).

43. A) N-Cyclohexyl-N-methyl 4-(1H-2-methyl-5-chlorobenzimidazylmethyl)benzenesulphonamide B) N-Cyclohexyl-N-methyl 4-(1H-2-methyl-6-chlorobenzimidazylmethyl)benzenesulphonamide

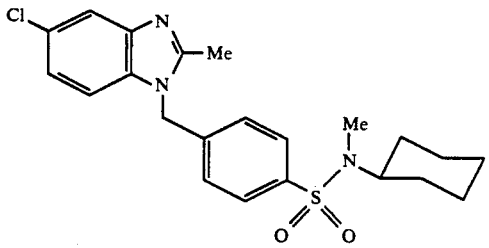

Example 43a

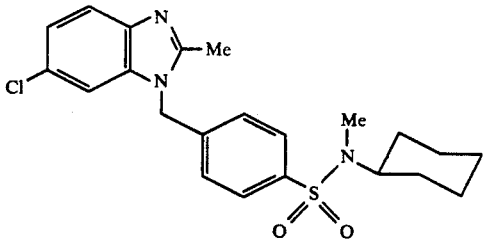

Example 43b

Product obtained as a 1:1 mixture of the two regioisomers A and B. Off white crystalline solid: m.p. 119°–121° C.

Analysis calculated for C$_{22}$H$_{26}$N$_3$O$_2$Cl Requires C 61.17 H 6.07 N 9.73 Found C 60.94 H 6.04 N 9.66 i.r (KBr) 1330, 1160 cm$^{-1}$ delta$_H$ (250 MHz, d$_6$- DMSO) 7.81–7.60 (2H, m), 7.30–7.00 (5H, m), 5.36 (2H, s), 3.80–3.65 (1H, m), 2.72 (3H, s), 2.55 (3H, s), 1.80–0.90

44. N-Cyclohexyl-N-methyl 4-(1H-2-methyl-5-nitrobenzimidazylmethyl) benzenesulphonamide

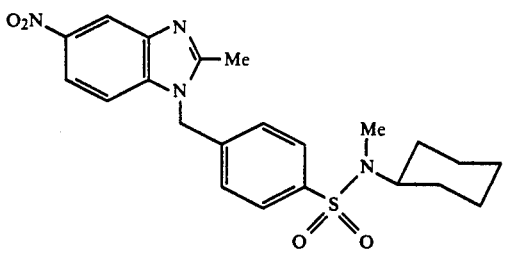

Example 44

Pale yellow crystalline solid: m.p. 159°–161° C.

Analysis calculated for C$_{22}$H$_{26}$N$_4$O$_4$S.0.8H$_2$O Requires C 57.83 H 6.09 N 12.26 Found C 58.13 H 5.78 N 11.90 i.r. (KBr) 1330, 1160 cm$^{-1}$ delta$_H$ (250 MHz, d$_6$-DMSO) 8.61 (1H, d, J 2 Hz), 8.15 (1H, dd, J 8.9 Hz, J 2 Hz), 7.76 (2H, d, J 8.4 Hz), 7.23 (1H, d, J 8.9 Hz), 7.15 (2H, d, J 8.4 Hz), 5.44 (2H, S), 3.79–3.62 (1H, m), 2.71 (3H, s), 2.61 (3H, s) 1.80–0.84 (10H, m).

45. N-Cyclohexyl-N-methyl 4-(1H-2-(2-pyridyl)benzimidazylmethyl) benzenesulphonamide

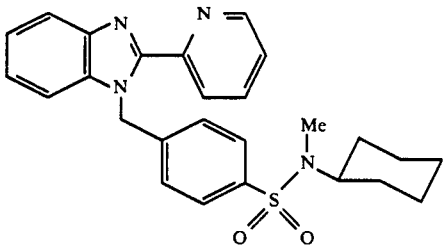

Example 45

White crystalline solid: m.p. 134°–135° C.

Analysis calculated for C$_{26}$H$_{28}$N$_4$O$_2$ Requires C 67.80 H 6.13 N 12.16 Found C 67.77 H 6.20 N 12.12 i.r. (KBr) 2930, 2850, 1330, 1160 cm$^{-1}$ delta$_H$ (250 MHz, CDCl$_3$) 8.58 (1H, d, J 0.9 Hz), 8.46 (1H, d, J 7.0 Hz), 7.85 (2H, m), 7.68 (2H, d, J 8.3 Hz), 7.33 (6H, m), 6.24 (2H, s),, 3.71 (1H, m), 2.69 (3H, s), 1.71–0.90 (10H, m).

46. N-Cyclohexyl-4-methyl 4-(1H-2,5,6-trimethylbenzimidazylmethyl) benzenesulphonamide

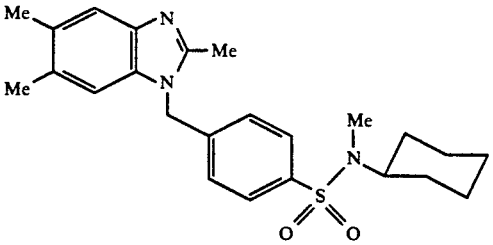

Example 46

White crystalline solid: m.p. 176°–177° C.

Analysis calculated for C$_{24}$H$_{31}$N$_3$O$_2$S.0.2H$_2$O Requires C 67.73 H 7.34 N 9.87 Found C 67.26 H 7.28 N 9.66 i.r. (KBr) 2930, 1330, 1160 cm$^{-1}$ delta$_H$ (250 MHz, CDCl$_3$) 7.74 (2H, d, i 8.3 Hz), 7.49 (1H, s), 7.15 (2H, d, J 8.3 Hz), 6.92 (1H, s), 5.33 (2H, s), 3.74 (1H, m), 2.72 (3H, s), 2.51 (3H, s), 2.51 (3H, s), 2.37 (3H, s), 1.78–0.85 (10H, m).

47. N-Cyclohexyl-N-methyl 4-(1H-naphtha[2,3-d]imidazylmethyl) benzenesulohonamide

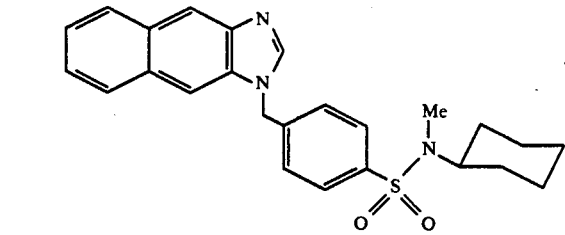

Example 47

Off white crystalline solid: m.p. 195°–197° C.

Analysis calculated for C$_{25}$H$_{27}$N$_3$O$_2$S.0.3H$_2$O Requires C 68.40 H 6.34 N 9.57 Found C 68.29 H 6.30 N 9.46 i.r. 1160 cm$^{-1}$ delta$_H$(250 MHz, d$_6$-DMSO) 8.34 (1H, s) 8.17 (1H, s), 8.10–8.00 (1H, m), 7.90–7.75 (3H, m), 7.61 (1H,-s), 7.48–7.38 (2H, m), 7.34 (2H, d, J 8.4 Hz), 5.53 (2H, s), 3.81–3.62 (1H, m), 2.71 (3H, s), 1.80–0.81 (10H, m).

48. N-Cyclohexyl-N-methyl 4-(1H-2-methylnaphth[2,3-d]imidazylmethyl) benzenesulphonamide

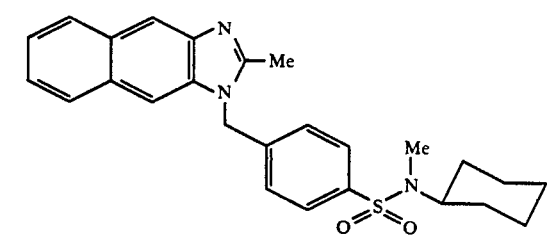

Example 48

Light brown crystalline solid: m.p. 198°–200° C.

Analysis calculated for C$_{26}$H$_{29}$N$_3$O$_2$S.0.2 H$_2$O Requires C 69.21 H 6.–47 N 9.31 Found C 69.20 H 6.52 N 9.23 i.r .(KBr) 1330, 1160 cm$^{-1}$ delta $_H$ (250 MHz, d$_6$-DMSO) 8.30–8.26 (1H, s), 8.11–7.95 (1H, m), 7.93–7.13 (8H, m), 5.42 (2H, s), 3.82–3.60 (1H, m), 2.70 (3H, S), 2.60 (3H, s), 1.90–0.84 (10H, n) .

EXAMPLES 49 TO 53

The compounds of Examples 49 to 53 were prepared by the method of Example 40 starting from the appropriate amine.

49. N-Cyclohexyl-N-ethyl 4-(1H-2-(2-methyl)benzimidazylmethyl) benzenesulphonamide

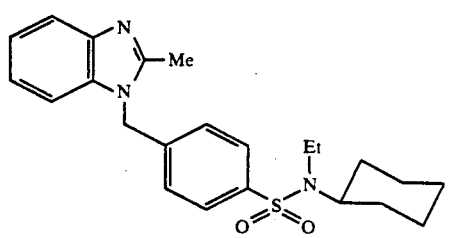

Example 49

Off white amorphous solid: m.p. 55°-570° C.

Analysis calculated for $C_{23}H_{29}N_3SO_2.0.3H_2O$ Requires C 56.25 H 7.16 N 10.08 Found C 66.22 H 7.06 N 10.07 i.r. (KBr) 1320, 1150 cm$^{-1}$ delta$_H$ (250MHz, CDCl$_3$) 7.79-7.73 (3H, m), 7.30-7.14 (5H, m), 5.38 (2H, s), 3.59 (1H, s), 3.19 (2H, q, J 7Hz), 2.56 (3H, s), 1.82-0.95 (10H, bm), (3H, t, J 7 Hz).

50. Piperidinyl 4-(1H-2-methylbenzimidazylmethyl)-benzenesulphonamide

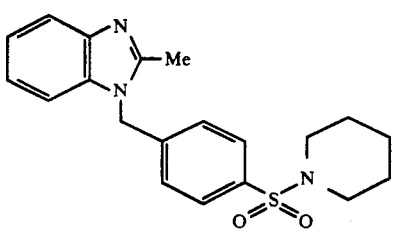

Example 50

Off white crystalline solid: m.p. 157-159° C.

Analysis calculated for $C_{20}H_{23}N_3O_2S.0.5H_2O$ Requires C 63.47 H 6.39 N 11.10 Found C 63.19 H 6.00 N 10.86 i.r. (KBr) 1330, 1160 cm$^{-1}$ delta$_H$ (250 MHz, d$_6$-DMSO) 7.80-7.65 (3H, m), 7.35-7.13 (5H, m), 5.40 (2H, s), 2.96 (4H, t, J 5.3 Hz), 2.58 (3H, s), 1.73-1.55 (4H, m), 1.50-1.35 (2H, m).

51. Morpholinyl 4-(1H-2-methylbenzimidazylmethyl)benzenesulphonamide

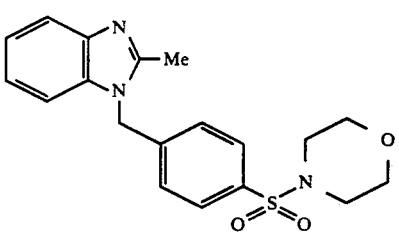

Example 51

Off white crystalline solid: m.p. 178°-180° C.

Analysis calculated for $C_{19}H_{21}N_3O_3S.0.1H_2O$ Requires C 61.44 H 5.70 N 11.31 Found C 61.06 H 5.75 N 11.01 i.r. (KBr) 1330, 1160 cm$^{-1}$ delta$_H$ (250 MHz, d$_6$-DMSO) 7.80-7.65 (3H, m), 7.34-7.13 (5H, 2H, s), 3.73 (4H, t, J 4.5 Hz), 2.98 (4H, t, J 4.5 Hz), 2.58 (3H, s).

52. Morpholinyl 4-(1H-benzimidazylmethyl)benzenesulphonamide

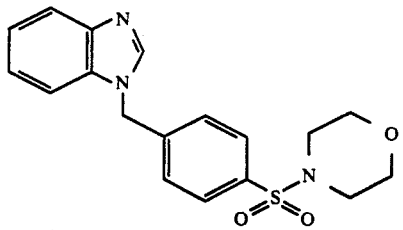

Example 52

Off white crystalline solid: m.p. 244°-246° C.

Analysis calculated for $C_{18}H_{19}N_3O_3S.0.8H_2O$ Requires C 58.14 H 5.58 N 11.30 Found C 58.17 H 5.26 N 11.01 i.r. (KBr) 1330, 1160 cm$^{-1}$ delta$_H$ (250 MHz, d$_6$-DMSO) 8.00 (1H, s), 7.92-7.85 (1H, m), 7.75-7.73 (2H, d, J 8.3 Hz), 7.35-7.20 (4H, m), 5.48 (2H, s), 3.73 (4H, t, J 4.5 Hz), 2.99 (4H, t, J 4.5 Hz).

53. 2-tiethylpiperidinyl 4-(1H-2-methylbenzimidazylmethyl) benzenesulphonamide

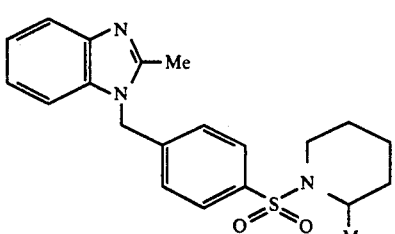

Example 53

White crystalline solid: m.p. 191°-195° C.

Analysis calculated for $C_{21}H_{25}N_3O_2S.0.7H_2O$ Requires C 63.68 H 6.72 N 10.61 Found C 63.56 H 6.35 N 10.38 i.r. (CHCl$_3$) 2930, 1340, 1155 cm$^{-1}$ delta$_H$ (250 MHz, CDCl$_3$) 7.80-7.70 (3H, m), 7.32-7.15 (5H, m), 5.41 (2H, s), 3.74 (2H, d, J 11 Hz), 2.58 (3H, s), 2.27 (2H, m), 1.66 (2H, m), 1.29 (3H, m), 0.90 (3H, d).

EXAMPLE 54

N-Methyl-N-4-(1H-2-methylbenzimidazylmethyl)-benzyl phenylsulphonamide

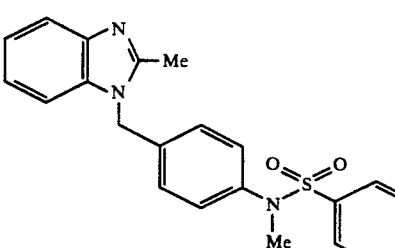

Example 54

(a) N-4-Methylbenzyl phenylsulphonamide

To an ice cold stirred solution of p-toluidine (5.00 g, 47 mmol) and triethylamine (6.5 ml, 51 mmol) in dry THF (100 ml) under argon was slowly added benzenesulphonyl chloride (5.9 ml, 47 mmol). A white precipitate formed. The ice bath was removed and the reaction stirred at ambient temperature for four hours. THF was evaporated under reduced pressure and the resulting oil partitioned between ethyl acetate (100 ml) and 2M hydrochloric acid (100 ml). The organic layer was separated and washed with 2M hydrochloric acid (3×75 ml), water (75 ml), 5% sodium hydrogen carbonate (3×75 ml) and finally water (75 ml). 4-he solution was then dried over MgSO4, filtered and evapourated to give the crude sulphonamide, which was crystallised from ethyl acetate/hexane to give N-4-methylbenzll phenylsulphonamide (9.8 g, 85%) as a white crystalline solid.

i.r. (CH₂Cl₂) 1330, 1165 cm⁻¹ delta$_H$(250 MHz, CDCl₃) 7.77 (2H, m), 7.45 (3H, m), 7.04 (2H, d, J 8.4 Hz), 6.96 d, J 8.5 Hz), 6.81 (1H, s), 2.28 (3H, s).

(b) N-Methyl-N-4-methylbenzyl phenylsulphonamide

Sodium hydride (80% dispersion in oil) (0.24 g, 10 mmol) was added to a stirred solution of N-4-methylbenzyl phenylsulphonamide (2.47 g, 10 mmol) in dry THF (50 mi) under argon. After 1.5 h the grey solid of sodium hydride disappeared and a white precipitate formed. The mixture was cooled to 0° C. and treated with methyl iodide (0.62 ml, 10 mmol). The reaction was allowed to warm to ambient temperature and stirred or 16 h. Methanol (1 ml) was added and the reaction mixture evaporated to dryness. The residue was partitioned between ethyl acetate (80 ml) and water (80 ml). The organic layer was separated, washed with water (2×50 ml), dried over MgSO4, filtered and the solvent removed to give the crude product. Flash chromatography (flash silica, gradient elution 0–10% ethyl acetate in hexane) gave, after crystallisation from ethyl acetate/hexane, N-methyl N-4-methylbenzyl phenylsulphonamide (0.89 g, 34%) as a white crystalline solid.

delta$_H$(250 MHz, CDCl₃) 7.55 (3H, m) 7.44 (2H, m), 7.08 (2H, d, J 8.0 Hz), 6.95 (2H, d, J 8.3 Hz), 3.14 (3H, s), 2.32 (3H, s).

(c) N-4-Bromomethylbenzyl-N-methyl phenysulphonamide

Utilising the procedure described in Example 1(a) employing N-methyl-N-4-methylbenzyl phenylsulphonamide (0.80g, 3.1 mmol) in lieu of ethyl p-toluate gave a crude product containing both brominated and unbrominated material. Flash chromatography (flash silica, gradient elution 0–10% ethyl acetate in hexane) gave, after crystallisation from ethyl acetate/hexane N-4 bromomethylbenzyl-N-methyl phenylsulphonamide (0.69 g, 66%) as a white crystalline solid.

delta$_H$(250 MHz, CDCl₃) 7.52 (5H, m), 7.64 (2H, d, J 8.5 Hz), 7.06 (2H, d, J 8.5 Hz), 7.06 (2H, d, J 8.5 Hz), 4.46 (2H, s), 3.15 (3H, s).

(d) N-methyl-N-4-(1H-2-methylbenzimidazylmethyl)benzyl phenylsulphonamide

Utilising the procedure described in Example 1(b) employing 2-methylbenzimidazole (268 mg, 2.0 mmol) and N-4-bromomethylbenzyl-N-methyl phenylsulphonamide(690 mg, 2.0 mmol) in lieu of benzimidazole and ethyl 4-bromomethylbenzoate respectively yielded a crude product which was purified by flash chromatography (flash silica gel, gradient elution 0–100% ethyl acetate in hexane) followed by crystallisation from ethyl acetate/hexane to yield N-methyl-N-4-(1H-2-methylbenzimidazylmethyl)benzyl phenylsulphonamide (156 mg, 20%) as a white crystalline solid.

m.p. 144°–146° C.

Analysis calculated for C₂₂H₂₁N₃O₂S.0.2H₂O Requires C 66.89 H 5.41 N 10.63 Found C 67.06 H 5.43 N 10.60 i.r. (KBr) (CH₂Cl₂) 1350, 1175 cm⁻¹ delta$_H$(250 MHz, CDCl₃) 7.70 (1H, m), 7.56 (2H., m), 7.48 (3H, m), 7.20 (3H, m), 7.00 (4H, m), 5.28 (2H, s), 3.11 (3H, s), 2.55 (3H, s).

EXAMPLES 55-56

The compounds of Examples 55 and 56 were prepared by the method of Example 54 starting from the appropriate sulphonyl chloride.

55. N-methyl-N-4-(1H-2-methylbenzimidazylmethyl)benzyl 2-naphthylsulphonamide

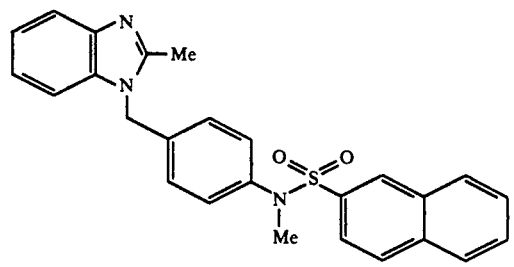

Example 55

White crystalline solid: m.p. 187° C.

i.r. (KBr) 1345, 1170 cm⁻¹ delta$^H$(250 MHz, CDCl₃) 7.10 (1H, d, J 1.5 Hz) 7.84 (3H, m), 7.62 (1H, d, J 7.6 Hz), 7.59 (2H, m), 7.43 (1H, dd, J 8.6 Hz, J 1.8 Hz), 7.21 (3H, m), 6.99 (4H, m), 5.29 (2H, s), 3.16 (3H, s), 2.55 (3H, s).

56. N-methyl-N-4-(1H-2-methylbenzimidazylmethyl)benzyl 4-bromophenylsulphonamide

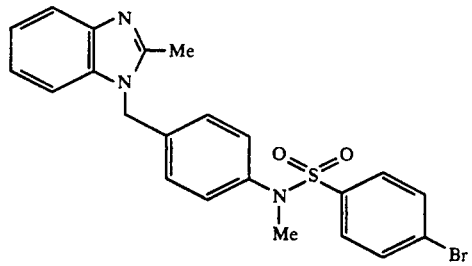

Example 56

White crystalline solid: m.p. 120° C.

Analysis calculated for C₂₂H₂₀BrN₃O₂S Requires C 56.18 H 4.29 N 8.93 Found C 56.09 H 4.33 N 8.89 i.r. (KBr) 1345, 1170 cm⁻¹ delta$_H$(250 MHz, CDCl₃) 7.68 (2H, m), 7.51 (4H, m), 7.32 (4H, m), 7.18 (2H, m) 5.24 (2H, s), 3.08 (3H, s), 2.52 (3H, s).

EXAMPLE 57

N-4-(1H-2-Methylbenzimidazylmethyl)benzyl phenylamide

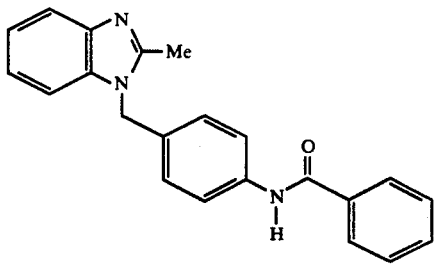

Example 57

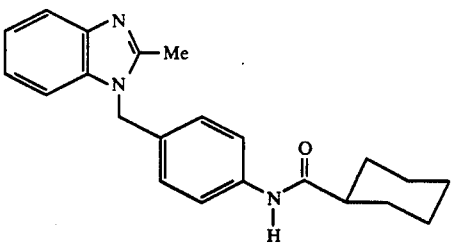

Example 58

(a) N-4-Methylbenzyl phenylamide

Utilising the procedure described in Example 54(a) employing benzoyl chloride (7.0 ml, 60 mmol) in lieu of benzenesulphonyl chloride gave a crude product which was purified by crystallisation from ethyl acetate to yield N-4-methylbenzyl phenylamide (10.50 g, 84%) as a white crystalline solid.

i.r. $(CH_2Cl_2)$ 3430, 1660 cm$^{-1}$ delta$_H$(250 MHz, CDCl$_3$) 7.86 (3H, m), 7.51 (4H, m), 7.17 (2H, d, J 8.4 Hz), 2.35 (3H, s).

(b) N-Methyl-N-4-methylbenzyl phenylamide

Utilising the procedure described in Example 54(b) employing N-4-methylbenzyl phenylamide (4.22 g, 20 mmol) in lieu of N-4-methylbenzyl phenylsulphonamide followed by flash chromatography (flash silica, gradied elution 0–10% ethyl acetate in hexane) gave, after crystallisation from ethyl acetate/hexane, N-methyl-N-4-methylbenzyl phenylamide (2.70 g, 60%) as a white crystalline solid.

delta$_H$(250 MHz, CDCl$_3$) 7.84 (3H, n), 7.49 (4H, m), 7.10 (2H, d, J 8.4 Hz), 3.15 (3H, s), 2.33 (3H, s).

(c) N-4-Bromomethylbenzyl phenyl amide

Utilising the procedure described in Example 1(a) employing N-methyl-N-4-methylbenzyl phenylamide (2.20 g, 9.8 mmol) in lieu of ethyl p-toluate cave N-4-bromomethylbenzyl phenyl amide (2.21 g) as a crude product. (Note: The reaction proceeds in an unusual fashion with demethylation of the amide nitrogen occurring.)

delta$_H$(250 MHz, CDCl$_3$) 7.28 (7H, m), 6.92 (2H, d, J 8.5 Hz), 4.38 (2H, s).

(d) N-4-(1H-2-Methylbenzimidazylmethyl)benzyl phenylamide

Utilising the procedure described in Example 1(b) employing 2-methylbenzimidazole (955 mg, 7.2 mmol) and crude N-4-bromomethylbenzyl phenylamide (2.00 g, 6.58 mmol) in lieu of benzimidazole and ethyl 4-bromomethylbenzoate respectively yielded a crude product which was purified by flash chromatography (flash silica gel, gradient elution 0–100% ethyl acetate in hexane) followed by crystallisation from ethyl acetate/hexane to give N-4-(1H-2-methylbenzimidazyolmethyl)benzyl phenylamide (110 mg, 4.9%).

m.p. 225° C.

Analysis calculated for $C_{22}H_{19}N_3O.0.5H_2O$ Requires C 75.41 H 5.75 N 11.99 Found C 75.71 H 5.68 N 11.75 i.r. $(CH_2Cl_2)$ 3420, 1685 cm$^{-1}$ delta$_H$(250 MHz, CDCl$_3$) 7.80 (2H, d, J 7.5 Hz), 7.59 (3H, m), 7.38 (3H, 7.10 (3H, m), 6.93 (2H, d, J 7.5 Hz), 5.21 (2H, s), 2.43 (3H, s).

EXAMPLE 58

N-4-(1H-2-Methylbenzimidazylmethyl)benzyl cyclohexylamide

N-4-(1H-2-Methylbenzimidazylmethyl)benzyl cyclohexylamide was prepared by the method of Example 57 starting from cyclohexanecarbonyl chloride.

White crystalline solid: m.p. 197° C.

Analysis calculated for $C_{22}H_{25}N_3O.0.3H_2O$ Requires C 74.88 H 7.23 N 11.91 Found C 74.92 H 7.24 N 11.83 i.r. (KBr) $(CH_2Cl_2)$ 3425, 1680 cm$^{-1}$ delta$_H$(250 MHz, CDCl$_3$) 7.68 (1H, m), 7.52 (2H, m), 7.22 (2H, m), 6.98 (2H, d, J 7.6 Hz), 5.25 (2H, s), 2.54 (3H, s).

EXAMPLE 59

N-Methyl-N-4-(1H-2-methylbenzimidazylmethyl)-benzyl diphenylphosphonamide

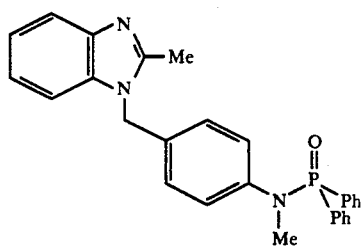

Example 59

(a) N-4-methylbenzyl diphenylphosphonamide

Utilising the procedure described in Example 54(a) employing diphenylphosphinic chloride (3.00 ml, 15.7 mmol) in lieu of benzenesulphonyl chloride gave a crude product which was purified by crystallisation from ethyl acetate to yield N-4-methylbenzyl diphenylphosphonamide-(3.50 g 72%) as a white crystalline solid.

i.r. $(CH_2Cl_2)$ 1200 cm$^{-1}$ delta$_H$(250 MHz, CDCl$_3$) 7.88 (4H, m), 7.42 (6H, m), 6.95 (4H, m), 2.21 (3H, s).

(b) N-Methyl-N-4-methylbenzyl diphenylphosphonamide

Utilising the procedure described in Example 54(b) employing N-4-methylbenzyl diphenylphosphonamide (1.10 g, 3.6 mmol) in lieu of N-4-methylbenzyl phenylsulphonamide followed by flash chromatography (flash silica, gradient elution 0–50% ethyl acetate in hexane) gave, after crystallisation from ethyl acetate/hexane, N-methyl-N-4-methylbenzyl diphenylphosphonamide (0.72 g, 62%) as a white crystalline solid.

delta$_H$(250 MHz, CDCl$_3$) 7.82 (4H, m), 7.36 (6H, m), 7.18 (28, d, J 8.5 Hz), 6.96 (2H, d, J 8.5 Hz), 3.08 (3H, d, J 10.4 Hz), 2.20 (3H, s).

(c) N-4-Bromomethyl-N-methyl diphenylphosphonamide

Utilising the procedure described in Example 1(a) employing N-methyl-N-4-methylbenzyl diphenylphosphonamide (700 mg, 1.9 mmol) in lieu of ethyl p-toluate gave a crude product (850 mg) which contained both brominated and unbrominated material. The crude material containing 11-4-bromomethyl-N-methyl diphenylphosphonamide was not purified.

(d) N-Methyl-N-4-(1H-2-methylbenzimidazylmethyl)benzyl diphenylphosphonamide.

Utilising the procedure described in Example 1(b) employing 2-methylbenzimidazole (380 mg, 2.9 mmol) and crude N-4-bromomethyl-N-methyl diphenyphosphonamide (0.85 g, 2.0 mmol) in lieu of benzimidazole and ethyl 4-bromomethylbenzoate respectively yielded a crude product which was purified by flash chromatography (flash silica gel, gradient elution 0-100% ethyl acetate in hexane and 0-1% methanol in ethyl acetate) followed by crystallisation from ethyl acetate/hexane to give N-methyl-N-4-(1H-2-methylbenzimidazylmethyl)benzyl diphenylphosphonamide (153 mg, 16%) as a white crystalline solid.

m.p. 198°-200° C.

Analysis calculated for $C_{28}H_{26}N_3OP.0.2H_2O$ Requires C 73.90 H 5.85 N 9.23 Found C 73.79 H 5.90 N 9.04 i.r. $(CH_2Cl_2)$ 1205 cm$^{-1}$ $delta_H$ (250 MHz, CDCl$_3$) 7.75 (5H, m), 7.38 (5H, m), 7.19 (6H, m), 6.85 (2H, d, J 7.6 Hz) , 5.14 (2H, s) , 3.02 ( 3H, d, J 9.7 Hz) , 2.43 (3H, s)

EXAMPLE 60

N-Cyclohexyl-N-methyl-4-(1-(1H-benzimidazylmethyl)benzamide

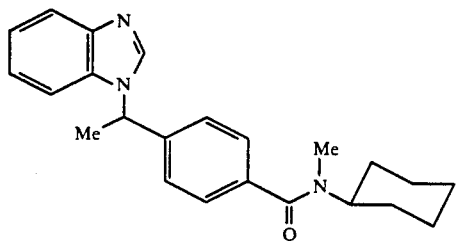

Example 60

To a stirred solution of N-cyclohexyl-N-methyl 4-(1H-benzimidazylmethyl)benzamide (347 mg, 1 mmol) in dry THF (20 ml) at −78 ° C. was added sodium bis(trimethylsilyl)amide (1.1 ml of 1M solution in THF) under argon. The mixture was left to stir at −78° C. for 40 minutes, a solution of methyl iodide (170 mg, 1.2 mmol) in dry THF (2 ml) was added and the mixture left to warm to ambient temperature overnight. The reaction mixture was partitioned between ethyl acetate and brine, the organic layer dried (Na$_2$SO$_4$), concentrated to give a crude product which was purified by column chromatography (flash silica gel, 4% methanol in DCM) to yield N-cyclohexyl-N-methyl 4-(1-(1H-benzimidazyl)ethyl)benzamide (40 mg, 11%) as a white crystalline solid.

m.p. 142°-145° C.

Analysis calculated for $C_{23}H_{27}N_3O.0.2H_2O$ Requires C 75.67 H 7.56 N 11.51 Found C 75.62 H 7.57 N 11.46 i.r. (nujol) 2910, 1630 cm$^{-1}$ $delta_H$ (250 MHz, CDCl$_3$) 8.14 (1H, s), 7.82 (1H, d, J 8 Hz), 7.38-7.04 (7H, m), 5.63 (1H, q, J 8 Hz), 4.48, 3.40 (1H, 2bm), 3.00, 2.78 (3H, 2bs), 2.03 (3H, d, J 8 Hz), 1.90–0.98 (10H, bm).

EXAMPLES 61-66

The compounds of Examples 61 to 66 were prepared by the method of Example 60 starting from N-cyclohexyl-N-methyl 4-(1H-benzimidazylmethyl)benzamide.

61. N-Cyclohexyl-N-methyl 4-(1-(1H-benzimidazyl)propyl)benzamide

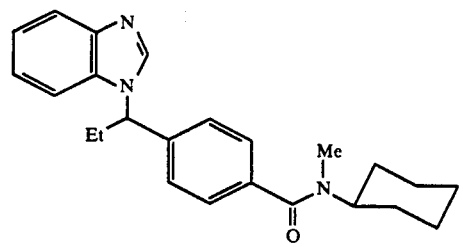

Example 61

White crystalline solid: m.p. 106°-108° C.

Analysis calculated for $C_{24}H_{29}N_3O$ Requires C 76.77 H 7.78 N 11.19 Found C 76.56 H 7.88 N 11.01 i.r. (KBr) 1615 cm$^{-1}$ $delta_H$ (250 MHz, CDCl$_3$) 8.11 (1H, s), 7.82 (1H, m), 7.39-7.16 (7H, n), 5.18 (2H, t, J 7.6 Hz), 4.50, 3.37 (1H, 2bs), 3.03-2.63 (3H, bd), 2.45 (2H, m), 1.89-1.11 (10H, bm), 1.00 (3H, t, J 7.3 Hz).

62. N-Cyclohexyl-N-methyl 4-(1-(1H-benzimidazyl)-but-3-enyl)benzamide

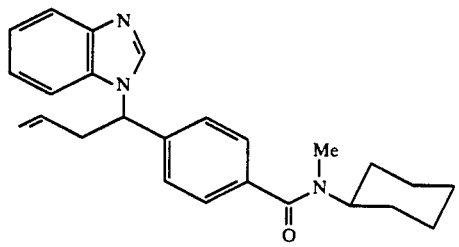

Example 62

White crystalline solid: m.p. 146°-147° C.

Analysis calculated for $C_{25}H_{29}N_3O$ Requires C 76.07 H 7.61 N 10.65 Found 76.09 H 7.45 N 10.72 i.r. (KBr) 1330, 1160 cm$^{-1}$ $delta_H$ (250 MHz, d$_6$-DMSO) 8.14 (1H, s) 7.81 (1H, d, J 7 Hz) 7.40-7.21 (7H, m), 5.82-5.60 (1H, m), 5.56 (1H, t, J 8 Hz), 5.02-5.19 (2,m), 4.44, 3.39 (1H, 2bm), 3.01-3.24 (2H, m), 2.99, 2.77 (3H, 2bs), 1.95-0.96 (10H, bm).

63. N-Cyclohexyl-N-methyl 4-(1H-benzimidazylthiomethylmethyl) benzamide

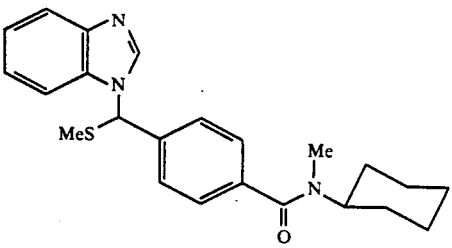

Example 63

White crystalline solid: m.p. 63°-66° C.

Analysis calculated for $C_{23}H_{27}N_3OS.0.4H_2O$

Requires C 68.93 H 6.99 N 10.49

Found C 69.05 H 7.02 N 10.29 i.r. (nujol) 2920, 1610 cm$^{-1}$ $delta_H$(250 MHz, CDCl$_3$) 8.42 (1H, s), 7.83 (1H, d, J 8 Hz), 7.38–7.20 (7H, m), 6.56 (1H, s), 4.44, 3.38 (1H, 2bm), 2.99, 2.76 (3H, 2bs), 2.18 (3 s), 1.92–0.94 (10H, bm).

64. N-Cyclohexyl-N-methyl 4-(1H-benzimidazyldithiomethylmethyl) benzamide

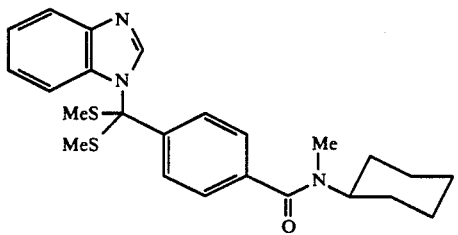

Example 64

Yellow crystalline solid: m.p. 42°–46° C.

Analysis calculated for $C_{24}H_{29}N_3OS_2$

Requires C 65.57 H 6.65 N 9.56

Found C 65.42 H 6.85 N 8.73 i.r. (nujol) 2910, 1605 cm$^{-1}$ $delta_H$(250 MHz, CDCl$_3$) 8.63 (1H, s), 7.81 (1H, d, J 8 Hz), 7.38–6.84 (7H, m), 4.50, 3.28 (1H, 2bm), 3.00, 2.80 (3H, 2bs), 1.96 (6H, s), 1.92–0.88 (10H, bm).

65. N-Cyclohexyl-N-methyl 4-(1H-benzimidazylthioethylmethyl) benzamide

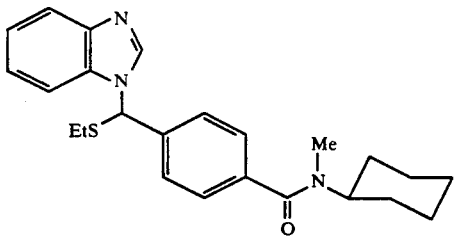

Example 65

White crystalline solid: m.p. 89°–91° C.

Analysis calculated for $C_{24}H_{29}N_3SO$

Requires C 70.73 H 7.17 N 10.31

Found C 71.00 H 7.21 N 10.21 i.r. (KBr) 1610 cm$^{-1}$ $delta_H$(250 MHz, CDCl$_3$) 8.47 (1H, s), 7.84 (1H, dd, J 6.8 Hz, J 1.2 Hz), 7.39–7.21 (7H, m), 6.61 (1H, s), 4.49–3.39 (1H, 2bs), 3.02–2.68 (3H, bd), 2.55 (2H, m), 1.28 (3H, t, J 7.4 Hz) 1.94–0.95 (10H, bm).

66. N-Cyclohexyl-N-methyl 4-(1H-benzimidazylthiophenylmethyl) benzamide

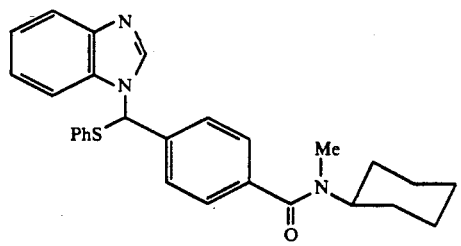

Example 66

White crystalline solid: m.p. 137°–139° C.

Analysis calculated for $C_{28}H_{29}N_3SO$

Requires C 73.81 H 6.42 N 9.22

Found C 74.14 H 6.57 N 9.25 i.r. (KBr) 1610 cm$^{-1}$ $delta_H$(250 MHz, CDCl$_3$) 8.15 (1H, s), 7.78 (1H, m), 7.43–7.21 (12H, m), 6.79 (1H, s), 4.50, 3.38 (1H, 2bs), 3.04–2.63 (3H, bd), 1.91–0.95 (10H, bm).

EXAMPLE 67

N-Cyclohexyl-N-methyl 4-(1H-benzimidazylmethylsulphonylmethyl) benzamide

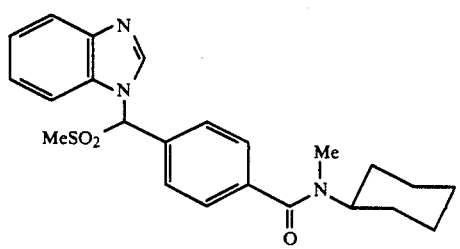

Example 67

Utilising the procedure described in Example 27 employing N-cyclohexyl-N-methyl 4-(1H-benzimidazylthiomethylmethyl)benzamide (250 mg, 0.64 mmol) in lieu of N-cyclohexyl-N-methyl 4-(1H-2-thiomethylbenzimidazylmethyl) benzamide, reaction in methanol (18 ml) with metachloroperbenzoic acid (400 mg, 2.3 mmol) gave a crude product which was purified by column chromatography (flash silica gel, ethyl acetate) followed by crystallisation from ethyl acetate to yield N-cyclohexyl-N-methyl 4-(1H-benzimidazylmethylsulphonylmethyl)benzamide (141 mg, 52.2%) as a white crystalline solid.

m.p. 142°–143° C.

i.r (KBr) 1610, 1330, 1145 cm$^{-1}$ $delta_H$(250 MHz, CDCl$_3$) 8.56 (1H, s), 7.88 (1H, m), 7.70 (2H, d, J 8.2 Hz), 7.61–7.26 (5H, m), 6.55 (1H, s), 4.50, 3.38 (1H, bs), 3.08–2.66 (3H, 2bs), 2.79 (3H, s), 1.95–0.95 (10H, bm).

EXAMPLE 68

N-Cyclohexyl-N-methyl 4-(1H-2-methylbenzimidazylthiomethylmethyl) benzamide

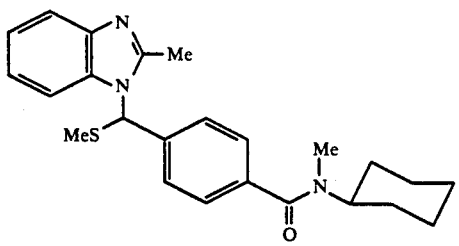

Example 68

N-Cyclohexyl-N-methyl 4-(1H-2-methylbenzimidazylthiomethylmethyl) benzamide was prepared by the method of Example 60 starting from N-cyclohexyl-N-methyl 4-(1H-2-methylbenzimidazylmethyl)benzamide and reacting with methyl disulphide.

Colourless viscous oil.
Analysis calculated for $C_{24}H_{29}N_3OS.0.4H_2O$
Requires C 69.50 H 7.24 N 10.13
Found C 69.50 H 7.38 N 9.78
i.r. (KBr) 2920, 1610 cm$^{-1}$
delta$_H$ (250 MHz, CDCl$_3$) 7.77 (1H, d, J 8 Hz), 7.43–7.22 (7H, m), 6.72 (1H, s), 4.52, 3.38 (1H, 2bm), 2.99, 2.78 (3H, 2bs), 2.63 (3H, s), 2.02 (3H, s), 1.91–0.97 (10H, bm).

69. N-Cyclohexyl-N-methyl 4-(1H-2-thiomethylbenzimidazylthiomethylmethyl)benzamide

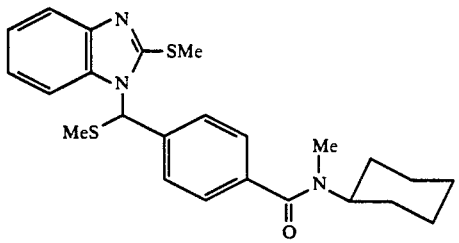

Example 69

N-Cyclohexyl-N-methyl 4-(1H-2-thiomethylbenzimidazylthiomethylmethyl) benzamide was prepared by the method of Example 60 starting from N-cyclohexyl-N-methyl 4-(1H-benzimidazylmethyl)benzamide and reacting with methyl disulphide.

White crystalline solid: 170°–171° C.
i.r. (KBr) 1650 cm$^{-1}$
delta$_H$ (250 MHz, CDCl$_3$) 7.70 (1H, d, J 8 Hz), 7.40–7.05 (7H, m), 6.75 (1H, s), 3.48–3.36 (1H, 2bs), 2.94 (3H, s), 2.97–2.71 (3H, bd), 2.01 (3H, s) 1.87–0.89 (10H, bm).

delta$_C$ (62.9 MHz, CDCl$_3$) 170.04, 153.33, 144.10, 136.99, 134.20, 127.18, 126.90, 126.55, 122.28, 121.68, 118.34, 112.74, 63.84, 58.20, 52.79, 30.71, 29.54, 27.41, 25.42, 25.03, 15.13, 14.57.

EXAMPLE 70

N-Cyclohexyl-N-ethyl 4-(1H-benzimidazylthiomethylmethyl) benzamide

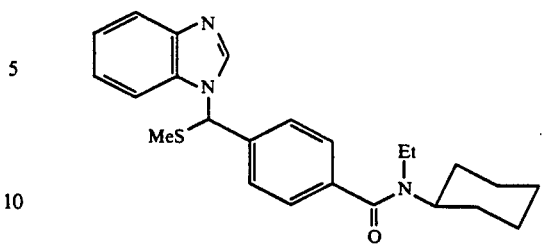

Example 70

N-Cyclohexyl-N-ethyl 4-(1H-benzimidazylthiomethylmethyl)benzamide was prepared by the method of Example 60 starting from N-cyclohexyl-N-ethyl 4-(1H-benzimidazylmethyl)benzamide and reacting with methyl disulphide.

White crystalline solid: m.p. 114°–115° C.
Analysis calculated for $C_{24}H_{29}N_3SO$
Requires C 70.73 H 7.17 N 10.31
Found C 70.71 H 7.19 N 10.28
i.r. (KBr) 1610 cm$^{-1}$
delta$_H$ (250 MHz, CDCl$_3$) 8.43 (1H, s), 7.84 (1H, dd, J 7.2 Hz, J 1.3 Hz), 7.35–7.19 (7H, m), 6.53 (1H, s), 3.39 (2H, bs), 3.18 (1H, bs), 2.11 (3H, s), 1.87–0.89 (13H, bm).

EXAMPLE 71

N-Cyclohexyl-N-methyl 4-(1H-benzimidazylthiomethylmethyl) benzenesulphonamide

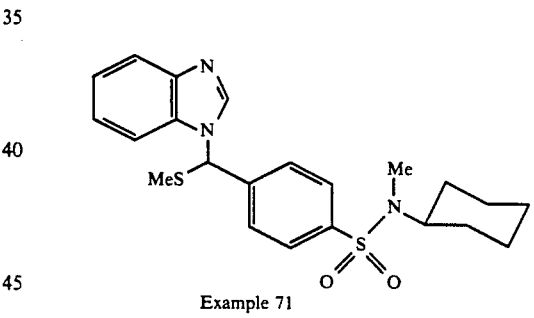

Example 71

N-Cyclohexyl-N-methyl 4-(1H-benzimidazylthiomethylmethyl) benzenesulphonamide was prepared by the method of Example 60 starting from N-cyclohexyl-N-methyl 4-(1H-benzimidazylmethyl)benzenesulphonamide and reacting with methyl disulphide. White crystalline solid: m.p. 60°–63° C.

Analysis calculated for $C_{22}H_{27}N_3O_2S_2$
Requires C 61.51 H 6.33 N 9.78 S 14.93
Found C 61.94 H 6.46 N 9.36 S 14.45
i.r. (KBr) 2920, 2850, 1620, 1450, 1330, 1150 cm$^{-1}$
delta$_H$ (250 MHz, CDCl$_3$) 8.41 (1H, s), 7.84 (1H, d, J 8.3Hz) 7.72 (2H, d, J 8.3 Hz), 7.36 (2H, d, J 8.3 Hz), 7.31–7.19 (3H, m), 6.55 (1H, s), 3.96 (1H, m), 2.68 (3H, s), 2.09, 2.01 (3H, 2bs), 1.86–1.19 (10H, m).

EXAMPLE 72

N-3-Chlorophenyl 4-(1H-2-methylbenzimidazylmethyl) benzenesulphonamide

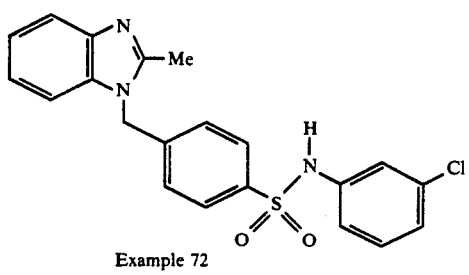

Example 72

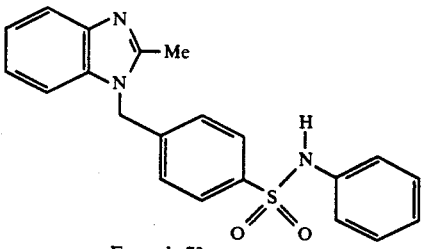

Example 73

(a) Utilising the procedure described in Example 1(a) employing p-toluenesulphenyl chloride (38 g, 0.2 mol) in benzene (150 ml) in lieu of ethyl 4-methylbenzoate in CCl₄ yielded after crystallisation (from DIPE) 4-bromomethylbenzenesulphenyl chloride (16.7 g, 31%) as a white crystalline solid.

delta$_H$ (250 MHz, CDCl₃) 8.02 (2H, d, J 8.5 Hz), 7.64 (2H, d, J 8.5 Hz), 4.52 (2H, s).

(b) Utilising the procedure described in Example (17a) but employing 4-bromomethylbenzenesulphenyl chloride (2.0 g, 7.4 mmol) in lieu of p-toluoyl chloride and 3-chloroaniline (0.95 g, 8 mmol) in lieu of N-methylcyclohexylamine yielded crude N-3-chlorophenyl 4-bromomethylbenzenesulphonamide (1.0 g, 38%) as an orange oil.

delta$_H$ (250 MHz, CDCl₃) 7.34–7.78 (3H, ,n), 7.43 (2H, m), 7.16–7.00 (4H, m), 4.53 (2H, s).

(c) the procedure described in Example 1(b) employing crude N-3-chloroaniline 4-bromomethylbenzenesulphonamide (1.0 g, 2.8 mmol) in lieu of ethyl 4-methylbenzoate, 2-methylbenzimidazole (0.41 g, 3.1 mmol) in lieu of benzimidazole and sodium bis(trimethylsilyl)amide (1M in hexane) (3.64 ml, 3.64 mmol) in lieu of sodium hydride yielded a crude product, which was purified by column chromatography (flash silica gel, 5% methanol/DCM) followed by crystallisation from methanol to give N-3-chlorophenyl 4-(1H-2-methylbenzimidazylmethylbenzenesulphonamide (290 mg, 25%) as a white crystalline solid.

m.p. 213°–214° C.

Analysis calculated for C₂₁H₁₈N₃SO₂Cl.0.1H₂O

Requires C 60.97 H 4.43 N 10.16

Found C 60.99 H 4.52 N 10.07 i.r. (KBr) 3400, 1330, 1160 cm⁻¹ delta$_H$ (250 MHz, CDCl₃) 7.67–7.55 (3H, m), 7.16–6.97 (10H, m), 5.26 (2H, s) 2.46 (3H, s).

EXAMPLES 73–97

The compounds of Examples 73 to 97 were prepared by the method of Example 72 starting from the appropriate amine.

73. N-Phenyl 4-(1H-2-methylbenzimidazylmethyl)-benzenesulphonamide

Colourless oil.

delta$_H$ (250 MHz, CDCl₃) 7.75–7.63 (3H, m), 7.30–7.00 (10H, m), 5.32 (2H, s), 2.51 (3H, s).

delta$_C$ (62.9 MHz, CDCl₃) 151.7, 142.4, 141.0, 139.0, 136.3, 135.0, 129.3, 127.9, 126.7, 125.5, 122.6, 122.4, 121.7, 109.1, 46.5.

74. N-4-Bromophenyl 4-(1H-2-methylbenzimidazylmethyl) benzenesulphonamide

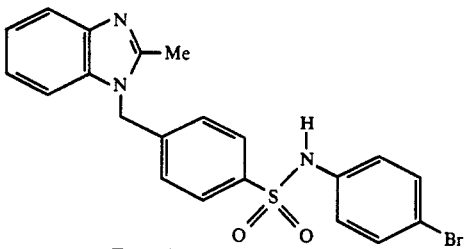

Example 74

Off white Crystalline solid: m.p. 111°–113° C.

Analysis calculated for C₂₁H₁₈N₃SO₂Br

Requires C 54.41 H 4.09 N 9.06

Found C 54.41 H 4.24 H 8.70 i.r. (KBr),3250, 1330, 1160 cm⁻¹ delta$_H$ (250 MHz, CDCl₃) 7.75–7.60 (3H, n), 7.40–6.93 (9H, m), 5.34 (2H, s), 2.53 (3H, s), 1.80–1.60 (1H, m).

75. N-3,4-Dimethoxyphenyl 4-(1H-2-methylbenzimidazylmethyl) benzenesulphonamide

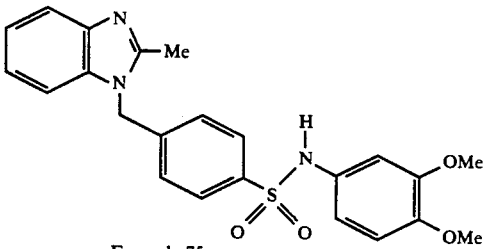

Example 75

White crystalline solid: m.p. 120° C.

Analysis calculated for C₂₃N₂₃N₃SO₄.0.4H₂O

Requires C 62.12 H 5.39 N 9.45

Found C 62.45 H 5.43 N 9.08 i.r. (KBr) 3250, 1330, 1160 cm⁻¹ delta$_H$ (250 MHz, CDCl₃) 8.10 (1H, brs), 7.65–7.50 (3H, m), 7.30–6.95 (5H, m), 6.70–6.46 (3H, m), 5.28 (2H, s), 3.77 (3H, s), 3.67 (3H, s), 2.50 (3H, s).

76. N-3,4,5-Trimethoxyphenyl 4-(1H-2-methylbenzimidazylmethyl) benzenesulphonamide

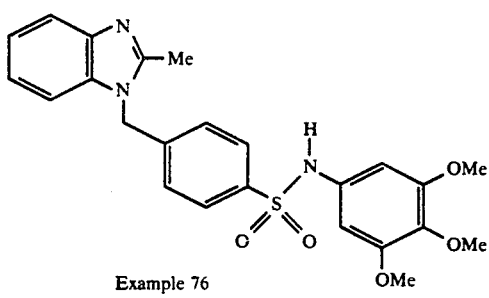

Example 76

Colourless oil.

delta$_H$(250 MHz, CDCl$_3$) 7.71-7.62 (3H, m) 6.28 (2H, s) , 5.32 (2H, s), 3.76 (3H, s), 3.65 (6H, s), 2.52 (3H, s).

77. N-3-Benzoylphenyl 4-(1H-2-methylbenzimidazylmethyl) benzenesulphonamide

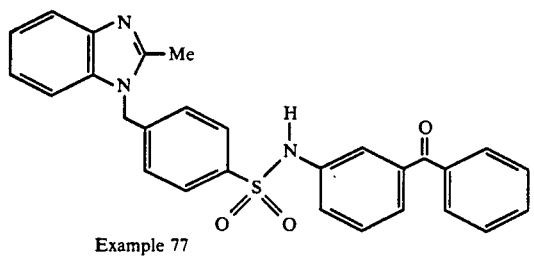

Example 77

Brown crystalline solid: m.p. 157°-158° C.
Analysis calculated for C$_{28}$H$_{23}$N$_3$SO$_3$.0.1H$_2$O
Requires C 69.58 H 4.84 N 8.69
Found C 69.57 H 4.93 N 8.64
i.r. (KBr) 3400, 1710, 1340, 1160 cm$^{-1}$
delta$_H$ (250 MHz, CDCl$_3$) 7.73-705 (18H, bm), 5.34 (2H, s), 2.51 (3H, s).

78. N-3-Benzoxyphenyl 4-(1H-2-methylbenzimidazylmethyl) benzenesulphonamide

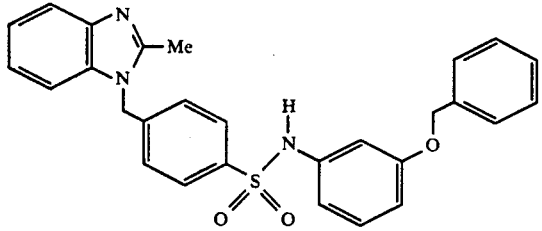

Example 78

Colourless oil.

delta$_H$ (250 MHz, CDCl$_3$) 7.95 (1H, bs), 7.75-7.60 (3H, m), 7.40-6.93 (11H, m), 6.82-6.59 (3H, m), 5.30 (2H, s), 4.97 (2H, s), 2.52 (3H, s).

79. N-Benzyl 4-(1H-2-methylbenzimidazylmethyl)-benzenesulphonamide

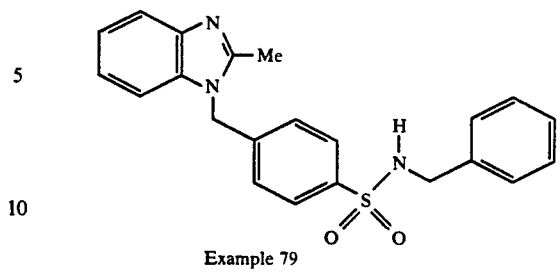

Example 79

Colourless oil.

delta$_H$ (250 MHz, CDCl$_3$) 7.84-7.66 (3H, m), 7.34-7.05 (10H, m), 5.34 (2H, s), 4.18-4.08 (2H, m), 2.57 (3H, s).

delta$_C$ (62.9 MHz, CDCl$_3$) 151.6, 140.7, 140.0, 135.1, 128.6, 128.5, 128.1, 127.8, 127.7, 127.2, 127.1, 126.8, 122.6, 122.4, 119.3, 109.1, 47.1, 46.5.

80. N-2-Chlorobenzyl 4-(1H-2-methylbenzimidazylmethyl) benzenesulphonamide

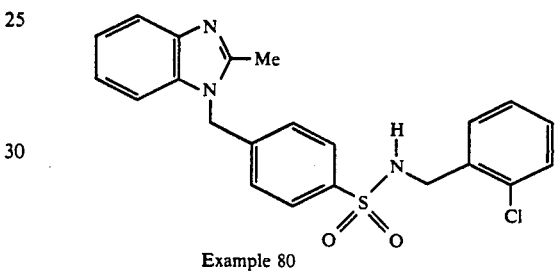

Example 80

White crystalline solid: m.p. 208°-210° C.
Analysis calculated for C$_{22}$H$_{20}$N$_3$SO$_2$Cl.0.1H$_2$O
Requires C 61.78 H 4.76 N 9.82
Found 61.38 H 4.83 N 9.63
i.r. (KBr) 3400, 1310, 1150 cm$^{-1}$
delta (250 MHz, CDCl$_3$) 7.77-7.69 (3H, m), 7.32-7.04 (9H, bm), 5.35 (2H, s), 5.03 (1H, t, J 6.5 Hz), 4.26 (2H, d, J 6.5 Hz), 2.57 (3H, s).

81. N-3-Chlorobenzyl 4-(1H-2-methylbenzimidazylmethyl) benzenesulphonamide

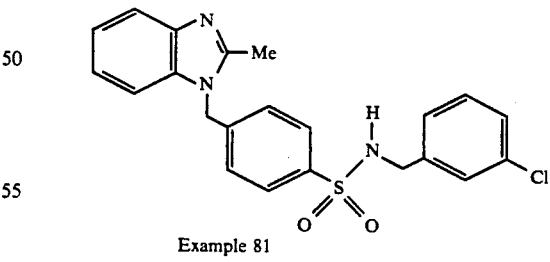

Example 81

White crystalline solid: m.p. 157°-158° C.
Analysis calculated for C$_{22}$H$_{20}$N$_3$SO$_2$Cl
Requires C 62.04 H 4.73 N 9.87
Found C 61.96 H 4.79 N 9.81
i.r. (KBr) 3400, 1325, 1150 cm$^{-1}$
delta$_H$ (250 MHz, CDCl$_3$) 7.82-7.58 (3H, m), 7.32-7.03 (9H, bm), 5.40 (2H, s) 4.96 (1H, t, J 6.2 Hz), 4.15 (2H, d, J 6.2 Hz), 2.58 (3H, s).

82. N-4-Chlorobenzyl 4-(1H-2-methylbenzimidazylmethyl) benzenesulphonamide

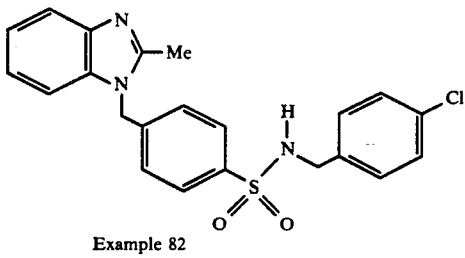

Example 82

White crystalline solid: m.p. 146°–147° C.
Analysis calculated for $C_{22}H_{20}N_3SO_2Cl.0.1H_2O$
Requires C 61.78 H 4.76 N 9.82
Found C 61.85 H 4.91 N 9.62
i.r. (KBr) 3400, 1320, 1155 cm$^{-1}$
$\delta_H$ (250 MHz, CDCl$_3$) 7.71–7.70 (3H, m), 7.26–707 (9H, bm), 5.38 (2H, s), 5.06 (1H, bs), 4.11 (2H, d, J 6.4 Hz), 2.56 (3H, s).

83. N-3,4-Dimethoxybenzyl 4-(1H-2-methylbenzimidazylmethyl) benzenesulphonamide

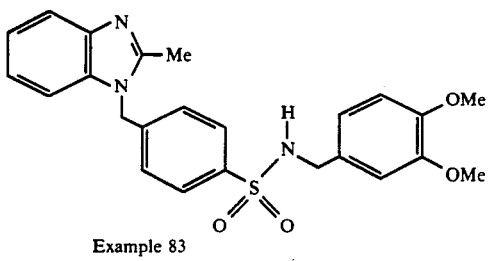

Example 83

White crystalline solid: m.p. 190°–191° C.
Analysis calculated for $C_{24}H_{25}N_3SO_4$
Requires C 63.84 H 5.58 N 9.31
Found C 63.54 H 5.62 N 9.09
i.r. (KBr) 3400, 1330, 1150 cm$^{-1}$
$\delta_H$ (250 MHz, CDCl$_3$) 7.83–7.72 (3H, m), 7.31–7.15 (5H, m), 6.77–6.61 (3H, m), 5.39 (2H, s), 4.73 (1H, t, J 6.0 Hz), 4.07 (2H, d, J 6.0 Hz), 5.83 (3H, s), 3.78 (3H, s), 3.78 (3H, s), 2.56 (3H, s).

84. N-4-tert-butylcyclohexyl 4-(1H-2-methylbenzimidazylmethyl) benzenesulphonamide

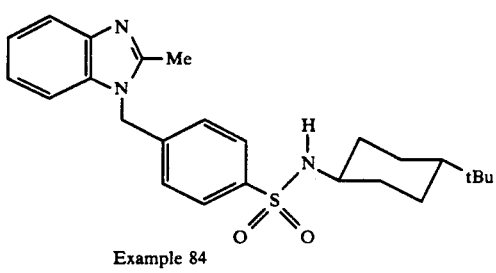

Example 84

White crystalline solid: m.p. 128°–131° C.
Analysis calculated for $C_{25}H_{33}N_3SO_2.0.3H_2O$
Requires C 68.30 H 7.57 N 9.56
Found C 67.52 H 7.54 N 9.29
i.r. (KBr) 3380, 2960, 1350, 1155 cm$^{-1}$
$\delta_H$ (250 MHz, CDCl$_3$) 7.78 (2H, d, J 8.3 Hz), 7.75 (1H, m), 7.31–7.16 (5H, bm), 5.40 (2H, s), 4.65, 4.31 (1H, 2d, J 7.5 Hz), 3.50, 3.04 (1H, 2bm), 2.58 (3H, s), 1.87–0.90 (9H, bm), 0.81 (9H, d, J 3.7 Hz).

85. N-1,2,3,4-Tetrahydro-1-naphthyl 4-(1H-2-methylbenzimidazylmethyl) benzenesulphonamide

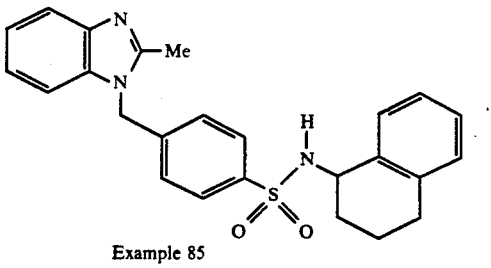

Example 85

White crystalline solid: m.p. 195°–197° C. (dec.
i.r. (CHCl$_3$) 3360, 2840, 1145 cm$^{-1}$
$\delta_H$ (250 MHz, CDCl$_3$) 7.81 (2H, d, J 8.3 Hz), 7.64 (1H, d, J 6.1 Hz), 7.27–6.87 (9H, m), 5.67 (1H, bs), 5.34 (2H, s), 4.43 (1H, m), 2.65 (2.11, m), 2.50 (3H, s), 1.78 (4H, m).
$\delta_C$ (62.9 MHz, CDCl$_3$) 151.6, 141.1, 140.7, 137.5, 135.3, 135.1, 129.2, 128.6, 128.5, 127.8, 127.7, 127.0, 126.1, 122.6, 122.4, 119.4, 109.1, 63.6, 52.0, 46.7, 30.8, 28.8.

86. N,N-Dicyclohexyl 4-(1H-2-methylbenzimidazylmethyl) benzenesulphonamide

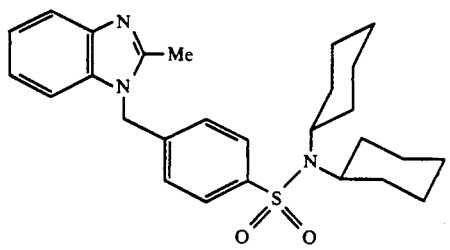

Example 86

Colourless oil.
$\delta_H$ (250 MHz, CDCl$_3$) 7.80–7.74 (3H, m), 7.37–7.04 (5H, M), 5.32 (2H, s), 3.33–3.12 (2H, n), 2.53 (3H, s), 1.90–1.50 (12H, m), 1.44–1.00 (8H, m).

87. 4-Phenylpiperidinyl 4-(1H-2)methylbenzimidazylmethyl) benzenesulphonamide

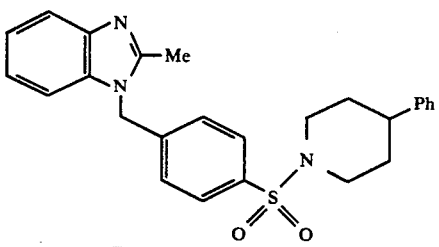

Example 87

White crystalline solid: m.p. 181°182° C.
Analysis calculated for $C_{26}H_{27}N_3O_2S$
Requires C 70.08 H 6.11 N 9.43
Found C 70.03 H 6.19 N 9.30
i.r. (CHCl$_3$) 2945, 1355, 1160 cm$^{-1}$
$\delta_H$ (250 MHz, CDCl$_3$) 7.77 (3H, m), 7.35–7.13 (10H, m), 5.43 (2H, s), 3.93 (2H, d, J 11.5 Hz), 2.60 (3H, s), 2.50–2.30 (3H, m), 1.95–1.80 (4H, m).

88. 3,3-Dimethylpiperidinyl 4-(1H-2-methylbenzimidazylmethyl) benzenesulphonamide

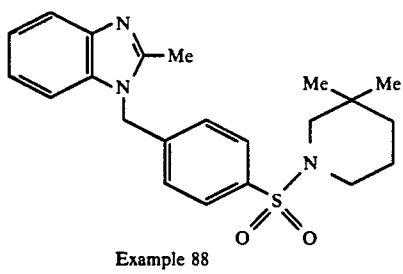

Example 88

White foam.
Analysis calculated for $C_{22}H_{27}N_3SO_2.0.6H_2O$
Requires C 64.71 H 6.96 N 10.29
Found C 64.67 H 6.74 N 10.02
i.r. (KBr) 1330, 1160 cm$^{-1}$
$\delta_H$ (250 MHz, CDCl$_3$) 7.80–7.60 (3H, m), 7.33–7.12 (5H, m), 5.39 (2H, s), 2.91 (2H, t, J 5.5 Hz), 2.62 (2H, s), 2.58 (3H, s), 1.74–1.60 (2H, 1.22 (2H, t, J 6.0 Hz), 0.96 (6H, s).

89. 4-(3-propylphenyl)piperazinyl 4-(1H-2-methylbenzimidazylmethyl) benzenesulphonamide

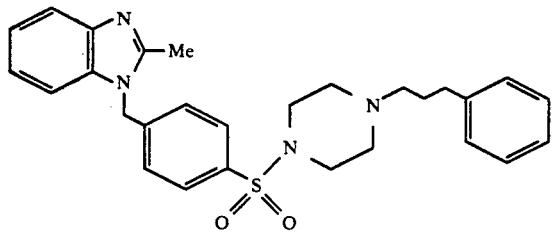

Example 89

Brown crystalline solid: m.p. 131°–133° C.
Analysis calculated for $C_{28}H_{32}N_4O_2S.0.6H_2O$
Requires C 67.33 H 6.70 N 11.22
Found C 67.44 H 6.54 N 11.03
i.r. (KBr) 1330, 1160 cm$^{-1}$
$\delta_H$ (250 MHz, d$_6$-DMSO) 7.80–7.63 (3H, m), 7.35–7.10 (10H, m), 5.40 (2H, s), 3.16–2.93 (4H, m), 2.66–2.45 (9H, m), 2.35 (2H, t, J 6.6 Hz), 1.82–1.70 (2H, m).

90. 4-Decylpiperazinyl 4-(1H-2-methylbenzimidazylmethyl) benzenesulphonamide

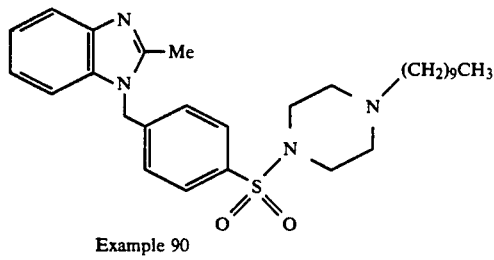

Example 90

Off white crystalline solid: m.p. 114°–116° C.
Analysis calculated for $C_{29}H_{42}N_4O_2S.0.6H_2O$
Requires C 66.79 H 8.35 N 10.74
Found C 66.86 H 8.07 N 10.63
i.r. (KBr) 1330, 1160 cm$^{-1}$
$\delta_H$ (250 MHz, d$_6$-DMSO) 7.80–7.63 (3H, m), 7.33–7.10 (5H, m) 5.39 (2H, s), 3.07–2.93 (4H, m), 2.56 (3H, s), 2.48 (4H, t, J 4.8 Hz) 2.34–2.25 (2H, m), 1.50–1.15 (16H, m), 0.87 (3H, t, J 6.3 Hz).

91. N-Decyl 4-(1H-2-methylbenzimidazylmethyl)-benzenesulphonamide

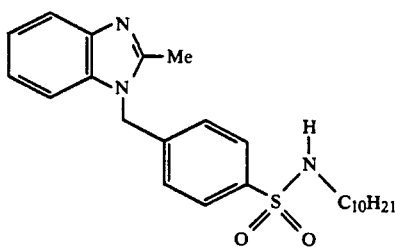

Example 91

White amorphous solid: m.p. 115°–116° C.
Analysis calculated for $C_{25}H_{35}N_3SO_2$
Requires C 67.99 H 7.99 N 9.51
Found C 67.93 H 7.95 N 9.51
i.r. (KBr) 3400, 1320, 1160 cm$^{-1}$
$\delta_H$ (250 MHz, CDCl$_3$) 7.83–7.83 (3H, m), 7.31–7.14 (5H, n), 5.40 (2H, s), 4.34 (1H, t, J 6.1 Hz), 2.94 (2H, q, J 6.6 Hz), 2.58 (3H, s), 1.43 (2H, bm), 0.88 (3H, t, J 6.6 Hz).

92. trans-Decahydroquinolinyl 4-(1H-2-methylbenzimidazylmethyl) benzenesulphonamide

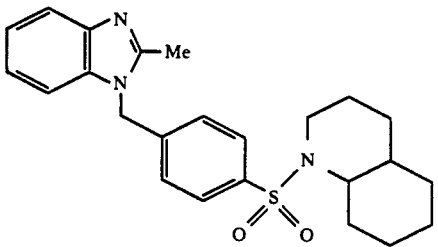

Example 92

Yellow oil.
i.r. (KBr) 2925, 1330, 1150 cm$^{-1}$
delta (250 MHz, CDCl$_3$( 7.74 (3H, m), 7.27–7.11 (5H, m), 5.35 (2H, s), 3.95 (1H, m), 3.64 (1H, m), 2.89 (1H, ddd, J 13 Hz, J 13 Hz, J 5 Hz), 2.54 (3H, s), 1.70–1.20 (13H, m).
$\delta_C$ (62.9 MHz, CDCl$_3$) 151.6, 142.5, 141.5, 140.1, 135.1, 127.3, 126.7, 122.4, 122.2, 119.2, 109.1, 55.3, 46.5, 40.2, 34.9, 31.3, 25.4, 23.8, 23.2, 19.3, 13.8.

93. N-1-Adamantyl 4-(1H-2-methylbenzimidazylmethyl)benzenesulphonamide

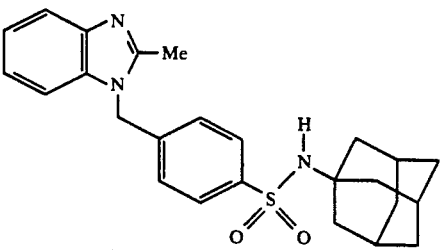

Example 93

White crystalline solid: m.p. 153° C. (dec.)
i.r. (KBr) 3250, 1325, 1150 cm$^{-1}$
$\delta_H$ (250 MHz, CDCl$_3$) 7.83–7.68 (3H, m), 7.30–7.02 (5H, m) 5.32 (2H, s), 5.20 (1H, bs), 2.53 (3H, s), 2.00–1.91 (3H, m), 1.80–1.65 (6H, m), 1.61–1.42 (6H, m).

$delta_C$ (62.9 MHz, CDCl$_3$) 151.7, 143.8, 142.5, 140.0, 135.1, 127.5, 126.6, 119.2, 122.2, 109.1, 55.2, 46.6, 42.9, 35.7, 29.3.

94. N-Methyl-N-phenyl 4-(1H-2-methylbenzimidazylmethyl) benzenesulphonamide

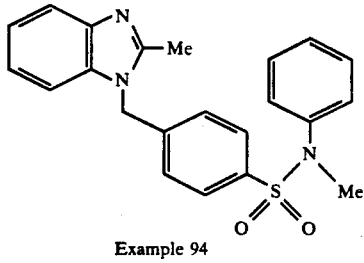

Example 94

Colourless oil.

$delta_H$ (250 MHz, CDCl$_3$) 7.81–7.78 (1H, m), 7.50 (2H, d, J 8 Hz), 7.37–7.10 (10H, m), 5.40 (2H, s), 3.17 (3H, s), 2.61 (3H, s).

$delta_C$ (62.9 MHz, CDCl$_3$) 151.5, 141.2, 128.9, 128.6, 127.5, 126.6, 126.5, 122.9, 122.7, 119.2, 109.1, 46.8, 38.2.

95. N-Benzyl-N-methyl 4-(1H-2-methylbenzimidazylmethyl) benzenesulphonamide

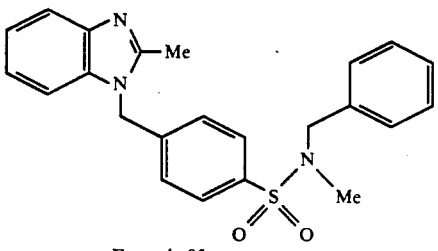

Example 95

Colourless oil.

$delta_H$ (250 MHz, CDCl$_3$) 7.81–7.71 (3H, m), 7.40–7.15 (10H, m), 5.39 (2H, s), 4.13 (2H, m), 2.58 (6H, s).

$delta_C$ (62.3 MHz, CDCl$_3$) 151.6, 142.6, 140.9, 137.4, 135.3, 125.1, 128.6, 128.3, 128.2, 128.0, 126.9, 122.6, 122.4, 119.4, 109.0, 54.0, 46.6, 34.4.

96. N-Benzyl-N-phenyl 4-(1H-2-methylbenzimidazylmethyl) benzenesulphonamide

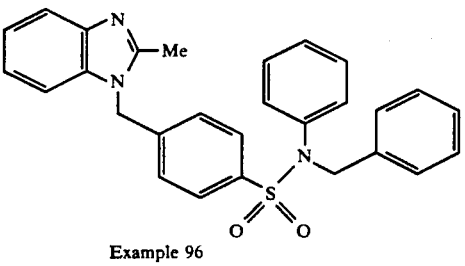

Example 96

White crystalline solid: m.p. 155°–156° C.
Analysis calculated for C$_{28}$H$_{25}$N$_3$SO$_2$
Requires C 71.91 H 5.39 N 8.99
Found C 71.80 H 5.49 N 8.89

$delta_H$ (250 MHz, CDCl$_3$) 7.79 (1H, d, J 7.5 Hz), 7.62 (1H, d, J 8.3 Hz), 7.26–7.15 (12H, bm), 6.92 (1H, m), 5.43 (2H, s), 4.72 (2H, s), 2.64 (3H, s).

97. N-Benzyl-N-2-phenylethyl 4-(1H-2-methylbenzimidazylmethyl) benzenesulphonamide

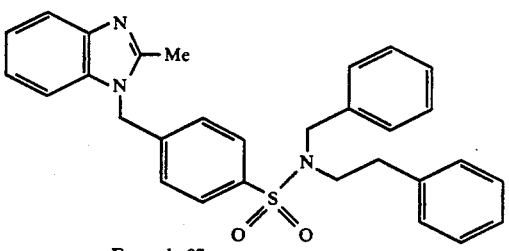

Example 97

Off white crystalline solid: m.p. 187° C.
Analysis calculated for C$_{30}$H$_{29}$N$_3$SO$_2$
Requires C 72.70 H 5.90 N 8.48
Found C 72.61 H 5.93 N 8.40
i.r. (KBr) 2940, 1340, 1155 cm$^{-1}$ $delta_H$ (250 MHz, CDCl$_3$) 7.77 (3H, m), 7.31–7.16 (13H, bm), 6.92 (2H, dd, J 7.9 Hz), 5.40 (2H, s), 4.33 (2H, s), 3.25 (2H, t, J 8.3 Hz), 2.60 (2H, t, J 8.3 Hz), 2.59 (3H, s).

EXAMPLE 98

N-3-Chlorobenzyl-N-methyl 4-(1H-2-methylbenzimidazylmethyl) benzenesulphonamide

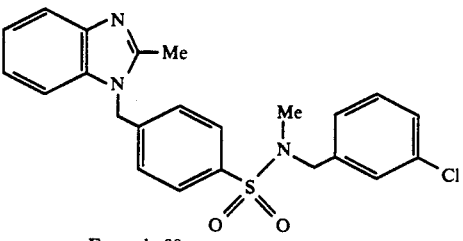

Example 98

A suspension of sodium hydride (60% dispersion 4-n oil (24 mg, 0.607 mmol) in dry THF (3 ml) under argon at 0° C. was treated with a solution of N-3-chlorobenzyl 4-(1H-2-methyl-benzimidazylmethyl) benzenesulphonamide (250 mg, 0.607 mmol) in dry THF (3 ml). The resulting solution was allowed to warm to room temperature for 10 minutes before before being quenched with methyl iodide (0.083 ml, 0.0607 mmol). The mixture was stirred at room temperature overnight. The reaction mixture was partitioned between ethyl acetate and ammonium chloride, the organic layer washed with brine, dried over MgSO$_4$ and the solvent removed. The crude product was purified by ptlc (2 mm silica TLC plate, 2% methanol/DCM) to yield N-3-chlorobenzyl-N-methyl 4-(1H-2-methylbenzimidazylmethyl) benzenesulphonamide (15.1 mg, 6%) as a colourless oil.

$delta_H$ (250 MHz, CDCl$_3$) 7.81–7.75 (3H, m), 7.31–7.12 (9H, m), 5.42 (2H, s), 4.12 (2H, s), 2.62 (3H, s), 2.59 (3H, s).

$delta_C$ (62.9 MHZ, CDCl$_3$) 137.50, 134.60, 130.00, 128.30, 128.20, 127.00, 126.30, 122.60, 122.40, 109.0, 53.5, 46.6, 34.5.

EXAMPLES 99–100

The compounds of Examples 99–100 were prepared by the method of Example 98 starting from the appropriate N-substituted 4-(1H-2-methylbenzimidazylmethyl)benzenesulphonamide.

99. N-4-Chlorobenzyl-N-methy 4-(1H-2-methylbenzimidazylmethyl) benzenesulphonamide

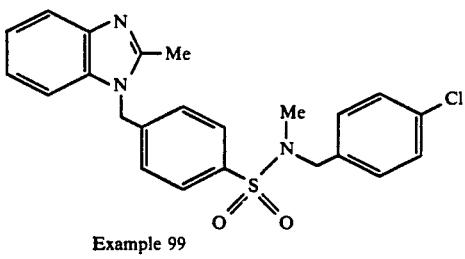

Example 99

Colourless oil.

$\delta_H$ (250 MHz, CDCl$_3$) 7.81–7.75 (3H, m), 7.38–7.16 (9H, m), 5.42 (2H, s), 4.11 (2H, s), 2.59 (6H, s).

$\delta_C$ (62.9 MHz, CDCl$_3$) 133.8, 128.8, 128.1, 126.9, 122.5, 122.3, 119.4, 108.9, 53.3, 46.5, 34.3.

100. N-1-Adamantyl-N-methyl 4-(1H-2-methylbenzimidazylmethyl) benzenesulphonamide

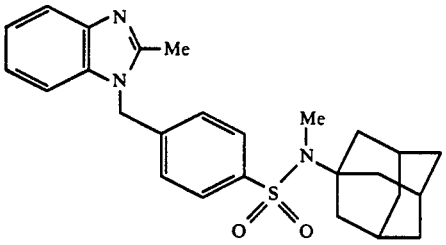

Example 100

Colourless oil.

$\delta_H$ (250 MHz, CDCl$_3$) 7.80–7.73 (3H, m), 7.32–7.13 (5H, m), 5.39 (2H, s), 2.93 (3H, s), 2.57 (3H, s), 2.17–1.93 (9H, m), 1.65–1.52 (6H,m).

$\delta_C$ (62.01 MHz, CDCl$_3$) 151.6, 143.6, 139.7, 135.2, 127.5, 126.6, 122.5, 122.3, 119.4, 109.1, 60.3, 46.7, 40.9, 36.0, 31.0, 30.0.

COMPARATIVE EXAMPLE

N-Cyclohexyl-N-methyl 4-(1H-imidazo(4,5-c]pyridin-1-ylmethyl)benzamide

This compound is not within the scope of the invention: It has been included here as a comparative example. This compound was described in EP-A-0260613.

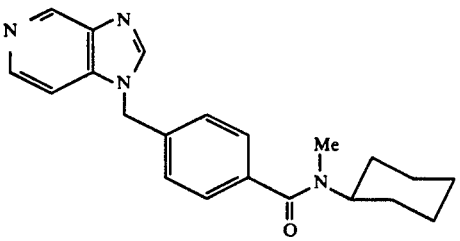

Comparative Example

Sodium bis(trimethylsilyl)amide (22 ml of 1M solution in THF) was added to a stirred solution of imidazo(4,5-c]pyridine (2.60 g, 0.02 mol) in dry TEF (200 ml) under-argon. A fine white precipitate formed. After 90 m the mixture was treated with purified N-cyclohexyl-N-methyl 4-bromomethylbenzamide (6.20 g, 0.02 mol) dissolved in dry THF (50 ml). The mixture was allowed to warm to ambient temperature and stirred overnight. Methanol (1 ml) was added, followed by water and the product extracted using ethyl acetate (3×150 ml). The combined organic layers were washed with water (2×100 ml), dried over K$_2$CO$_3$ and the solvent removed to give the crude product. Flash chromatography (flash silica, 10% methanol in ethyl acetate) followed by repeated fractional crystallisation (6 times from ethyl acetate/DIPE) gave the desired regioisomer N-cyclohexyl-N-methyl 4-(1H-imidazo(4,5-c]pyridin-1-ylmethyl)benzamide (0.39 g, 5%) as an off white crystalline solid.

m.p. 121°–123° C.

Analysis calculated for C$_{21}$H$_{24}$N$_4$O.0.6H$_2$O

Requires C 70.21 H 7.07 N 15.60

Found C 70.08 H 6.91 N 15.37 i.r. (KBr) 3080, 2930, 1615 cm$^{-1}$ $\delta_H$ (250 MHz, CDCl$_3$) 9.17 (1H, s), 8.42 (1H, d, J 5.6 Hz), 8.03 (1H, s), 7.37 (2H, d, J 7.8 Hz), 7.27–7.19 (3H, 5.42 (2H, s), 4.50, 3.37 (1H, 2bm), 2.96, 2.76 (3H, 2bs), 2.05–1.02 (10H, bm).

Pharmacology Example

The inhibition of $^3$H-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 Mm NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mM MgCl$_2$, 2 mM EDTA, pH 7.0), snap-freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was reseated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of a Tris-buffered solutions of the selected antagonist of predetermined concentrations. Each of these solutions contained $^3$H-PAF (0.5 nM; 1-O-($^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgCl$_2$, pH 7.0, 0.25% BSA) to make the final volume 1 ml. Incubation was initiated by the addition of 100 μg of the isolated membrane fraction to each of the above solutions at 0° C. Two control samples, one which (C13) contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fiber falter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation.

%Inhibition = [(TB−TBA)/SB]×100 where the specific binding SB=TB−NSB.

Table I lists results from this assay for inhibition of $^3$H-PAF receptor binding for illustrative examples of the compounds of this invention. Also presented in Table I is the result for a comparative example is (N-cyclohexyl-N-methyl 4-(1H-imidazo(4,5-c)pyridin-1-ylmethyl)benzamide). This compound (a PAF antagonist described in EP-A-0260613) is not within the scope of the invention.

TABLE I

Results for inhibition of $^3$H-PAF receptor binding

| Example | Inhibition of $^3$H-PAF binding IC$_{50}$ μM |
|---|---|
| 21 | 0.5 |
| 22 | 0.65 |
| 26 | 3 |
| 41 | 0.3 |
| 44 | 5 |
| 49 | 0.5 |
| 50 | 2 |
| 58 | 2 |
| 59 | 0.5 |
| 63 | 0.5 |
| 80 | 0.9 |
| 92 | 0.7 |
| Comparative Example | 10 |

We claim:

1. A compound of general formula I:

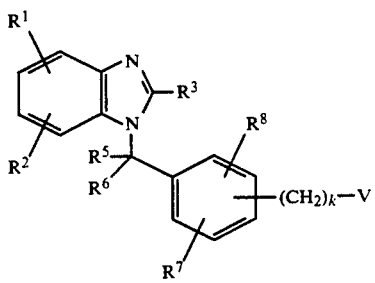

wherein:
each of $R^1$ and $R^2$ represents independently hydrogen, $C_1$-$C_6$ alkyl, $C_2$-$C_6$ alkenyl, halogen, CN, $CO_2H$, $CO_2$($C_1$-$C_6$) alkyl, $CO_2$($C_3$-$C_8$)cycloalkyl, $CONH_2$, CHO, $CH_2OH$, $CF_3$, $C_1$-$C_6$ alkoxy, $C_1$-$C_6$ alkylthio, SO($C_1$-$C_6$)alkyl, $SO_2$($C_1$-$C_6$) alkyl, $SO_3H$, $NH_2$, NHCOMe, or $NO_2$ or $R^1$ and $R^2$ together with the carbon atoms to which they are attached form a fused phenyl ring;

$R^3$ represents a hydrogen, $C_1$-$C_6$ alkyl, $C_1$-$C_6$ alkenyl, $C_1$-$C_6$ alkoxy, $C_1$-$C_6$ alkylthio, $C_1$-$C_6$ alkoxy ($C_1$-$C_6$) alkyl, $C_1$-$C_6$ alkylthio ($C_1$-$C_6$) alkyl, SO($C_1$-$C_6$) alkyl, $SO_2$($C_1$-$C_6$) alkyl, $CF_3$, phenyl ($C_1$-$C_6$) alkyl, thiophenyl, thiazole, pyridyl or a

group wherein $R^4$ represents hydrogen, $C_1$-$C_6$ alkyl, $C_2$-$C_6$ alkenyl, halogen, OH, SH, CN, $CO_2H$, $CO_2$($C_1$-$C_6$) alkyl, $CONH_2$, CHO, $CH_2OH$, $CF_3$, $C_1$-$C_6$ alkoxy, $C_1$-$C_6$ alkylthio, SO($C_1$-$C_6$) alkyl, ($SO_2$($C_1$-$C_6$) alkyl, $NH_2$, NHCOMe, or $NO_2$;

each of $R^5$ and $R^6$ represents independently hydrogen, $C_1$-$C_6$ alkyl, $C_2$-$C_6$ alkenyl, $CO_2$($C_1$-$C_6$) alkyl, $C_1$-$C_6$ alkylthio, SO($C_1$-$C_6$) alkyl, $SO_2$($C_1$-$C_6$) alkyl, $C_1$-$C_6$ alkylthio ($C_1$-$C_6$) alkyl, $C_1$-$C_6$ alkoxy ($C_1$-$C_6$) alkyl, phenyl ($C_1$-$C_6$) alkyl and thiophenyl;

k is an integer from 0 to 2;

each of $R^7$ and $R^8$ independently represents hydrogen, $C_1$-$C_6$ alkyl, $C_2$-$C_6$ alkenyl, $C_1$-$C_6$ alkoxy, $C_1$-$C_6$ alkylthio, $C_1$-$C_6$ alkoxy ($C_1$-$C_6$) alkyl, $C_1$-$C_6$ alkylthio ($C_1$-$C_6$) alkyl, halogen, $CF_3$, CN, OH, SH, $CH_2OH$, $CH_2SH$ or $CONH_2$;

V represents;

a) a $YNR^9R^{10}$ group wherein Y is $SO_2$, $PO_2$, CO or CS and each of $R^9$ and $R^{10}$ is independently hydrogen, $C_1$-$C_{18}$ alkyl, $C_2$-$C_{18}$ alkenyl, $C_3$-$C_8$ cycloalkyl, $C_4$-$C_8$ cycloalkenyl, phenyl ($C_1$-$C_6$) alkyl, adamantyl, decalynyl, naphthyl, $C_3$-$C_8$ cycloalkyl ($C_1$-$C_6$) alkyl, $C_4$-$C_8$ cycloalkenyl ($C_1$-$C_6$) alkyl or a group G wherein G represents a group:

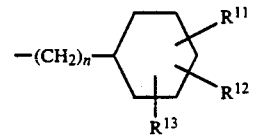

or a group:

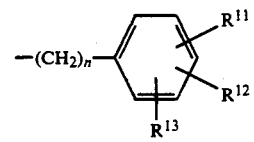

wherein n is an integer of from 1 to 6 and each of $R^{11}$, $R^{12}$ and $R^{13}$ is independently hydrogen, halogen, $C_1$-$C_{18}$ alkyl, $C_2$-$C_{18}$ alkenyl, $C_3$-$C_8$ cycloalkyl, $C_4$-$C_8$ cycloalkenyl, phenyl ($C_1$-$C_6$) alkyl, $C_3$-$C_8$ cycloalkyl ($C_1$-$C_6$) alkyl, $C_4$-$C_8$ cycloalkenyl ($C_1$-$C_6$) alkyl or a $C_1$-$C_6$ alkoxy, benzoxy, $C_1$-$C_6$ alkylthio, benzthio or benzoyl; or b) a $ZR^{19}$ group wherein Z represents tetrazole, CO, $CO_2$, $NR^{20}CO$, $NR^{20}CO_2$, $SO_2$, $NR^{20}SO_2$, $O_2C$, or $OCONR^{20}$ and each of $R^{19}$ and $R^{20}$ independently represents hydrogen, $C_1$-$C_{18}$ alkyl, $C_2$-$C_{18}$ alkenyl, $C_3$-$C_8$ cycloalkyl, $C_4$-$C_8$ cycloalkenyl, adamantyl, decalynyl, phenyl ($C_1$-$C_6$) alkyl, $C_3$-$C_8$ cycloalkyl ($C_1$-$C_6$) alkyl, $C_4$-$C_8$ cycloalkenyl, ($C_1$-$C_6$) alkyl, naphthyl, or a group G as defined above;

c) an $NR^{21}POR^{22}R^{23}$ group wherein each $R^{21}$, $R^{22}$ and $R^{23}$ independently represents hydrogen, $C_1$-$C_{18}$ alkyl, $C_2$-$C_{18}$ alkenyl, $C_3$-$C_8$ cycloalkyl, $C_4$-$C_8$ cycloalkenyl, adamantyl, decalynyl, phenyl ($C_1$-$C_6$) alkyl, $C_3$-$C_8$ cycloalkyl ($C_1$-$C_6$) alkyl, $C_4$-$C_8$ cycloalkenyl ($C_1$-$C_6$) alkyl, naphthyl or a group G as defined above;

or a pharmaceutically or veterinarily acceptable acid addition salt or hydrate thereof, provided that one of the following conditions is met:
a) when either of $R^1$ or $R^2$ is hydrogen the other is not halogen or ($C_1$-$C_6$) alkyl; or
b) $R^1$ and $R^2$ are not both halogen or ($C_1$-$C_6$) alkyl; or
c) $R^3$ is not H or ($C_1$-$C_6$) alkyl; or
d) when either of $R^5$ or $R^6$ is hydrogen the other is not hydrogen or ($C_1$-$C_6$) alkyl; or
e) $R^7$ and $R^8$ are not both hydrogen; or
f) when $k=0$, $V=ZR^{19}$ and $Z=SO_2$, $R^{19}$ is not phenyl($C_1$-$C_6$)alkyl.

2. A compound as claimed in claim 1, in which $R^1$ represents a hydrogen atom, a $C_1$-$C_6$ alkoxy group, a nitro group or, together with $R^2$ and the carbon atoms to which they are attached, forms a fused phenyl ring.

3. A compound as claimed in claim 1, wherein $R^2$ represents a hydrogen atom, a $C_1$-$C_6$ alkoxy group, a nitro group or, together with $R^1$ and the carbon atoms to which they are attached, forms a fused phenyl ring.

4. A compound as claimed in claim 1, wherein $R^3$ represents a hydrogen atom, a ($C_1$-$C_6$) alkyl group, a ($C_1$-$C_6$) alkylthio group, an $SO(C_1$-$C_6)$ alkyl group, an $SO_2(C_1$-$C_6)$ alkyl group, a $C_1$-$C_6$ alkylthio ($C_1$-$C_6$) alkyl group, a trifluoromethyl group, a thiazole group, a pyridyl group or a

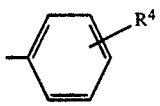

group.

5. A compound as claimed in claim 1, wherein $R^4$ represents a hydrogen or halogen atom.

6. A compound as claimed in claim 1, wherein $R^5$ represents a hydrogen atom, a $C_1$-$C_6$ alkyl group, a $C_2$-$C_6$ alkenyl group, a $C_1$-$C_6$ alkylthio group, a $SO_2(C_1$-$C_6)$ alkyl group or a thiophenyl group.

7. A compound as claimed in claim 1, wherein $R^6$ represents a hydrogen atom or a $C_1$-$C_6$ alkylthio group.

8. A compound as claimed in claim 1, wherein k represents an integer of zero.

9. A compound as claimed in claim 1, wherein $R^7$ represents a hydrogen atom, a $C_1$-$C_6$ alkoxy group or a halogen atom.

10. A compound as claimed in claim 1, wherein $R^8$ represents a hydrogen atom.

11. A compound as claimed in claim 1, wherein V represents a $YNR^9R^{10}$ group, a $ZR^{19}$ group or a $NR^{21}POR^{22}R^{23}$ group.

12. A compound as claimed in claim 1, wherein Y represents CO or $SO_2$.

13. A compound as claimed in claim 1, wherein $R^9$ represents a hydrogen atom, a $C_1$-$C_{18}$ alkyl group, a $C_3$-$C_8$ cycloalkyl group, or a group G.

14. A compound as claimed in claim 1, wherein $R^{10}$ represents a $C_1$-$C_{18}$ alkyl group, a $C_3$-$C_8$ cycloalkyl group, an adamantyl group, a naphthyl group or a group G.

15. A compound as claimed in claim 1, wherein G represents either a

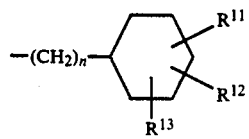

group or a

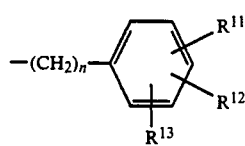

group.

16. A compound as claimed in claim 1, wherein n represents an integer of 1 or 2.

17. A compound as claimed in claim 1, wherein $R^{11}$ represents a hydrogen atom, a halogen atom, a $C_1$-$C_{18}$ alkyl group, a $C_1$-$C_6$ alkoxy group, a benzoxy group or a benzoyl group.

18. A compound as claimed in claim 1, wherein $R^{12}$ represents a hydrogen atom or a $C_1$-$C_6$ alkoxy group.

19. A compound as claimed in claim 1, wherein $R^{13}$ represents a hydrogen atom or a $C_1$-$C_6$ alkoxy group.

20. A compound as claimed in claim 1, wherein Z represents a CO group, $CO_2$ group, $NR^{20}$ CO group or $NR^{20}SO_2$ group.

21. A compound as claimed in claim 1, wherein $R^{19}$ represents a $C_1$-$C_{18}$ alkyl group, a $C_3$-$C_8$ cycloalkyl group, a naphthyl group, or a group G.

22. A compound as claimed in claim 1, wherein $R^{20}$ represents a hydrogen atom or a $C_1$-$C_{18}$ alkyl group.

23. A compound as claimed in claim 1, wherein $R^{21}$ represents a $C_1$-$C_{18}$ alkyl group.

24. A compound as claimed in claim 1, wherein $R^{22}$ represents a group G.

25. A compound as claimed in claim 1, wherein $R^{23}$ represents a group G.

26. Ethyl 4-(1H-benzimidazylmethyl)benzoate,
Ethyl 3-bromo-4-(1H-benzimidazylmethyl)benzoate,
Ethyl 3-fluoro-4-(1H-benzimidazylmethyl)benzoate,
Ethyl 3-methoxy-4-(1H-benzimidazylmethyl)benzoate,
(A) Ethyl 4-(1H-6-methoxybenzimidazylmethyl)benzoate,
(B) Ethyl 4-(1H-5-methoxybenzimidazylmethyl)benzoate,
Ethyl 4-(1H-5-nitrobenzimidazylmethyl)benzoate,
N-Cyclohexyl 4-(1H-benzimidazylmethyl)benzamide,
N-Benzyl 4-(1H-benzimidazylmethyl)benzamide,
N-Phenyl 4-(1H-benzimidazylmethyl)benzamide, N-3-Chlorophenyl 4-(1H-benzimidazylmethyl)benzamide,
N-3-Methoxyphenyl 4-(1H-benzimidazylmethyl)benzamide,
N-3-Benzoxyphenyl 4-(1H-benzimidazylmethyl)benzamide,
N-Tetradecyl 4-(1H-benzimidazylmethyl)benzamide,
N-Cyclohexyl 3-(1H-benzimidazylmethyl)benzamide,
N-Cyclohexyl-N-methyl 3(1H-benzimidazylmethyl)benzamide,
Benzoyl 4-(1H-2-methylbenzimidazylmethyl)benzene,
N-Cyclohexyl-N-methyl 4-(1H-benzimidazylmethyl)benzamide,
N-Methyl-N-phenyl-4-(1H-benzimidazylmethyl)benzamide,
N-Cyclohexyl-N-ethyl 4-(1H-benzimidazylmethyl)benzamide,
N-Cyclohexyl-N-methyl 4-(1H-2-methylbenzimidazylmethyl)benzamide,
N-Cyclohexyl-N-ethyl 4-(1H-2-benzimidazylmethyl)benzamide,
N,N-Dicyclohexyl 4-(1-2-benzimidazylmethyl)benzamide,
N-Cyclohexyl-N-methyl 4-(1H-2-ethylbenzimidazylmethyl)benzamide,
N-Cyclohexyl-N-methyl 4-(1H-2-isopropylbenzimidazylmethyl) benzamide,
N-Cyclohexyl-N-methyl 4-(1H-2-tert-butylbenzimidazylmethyl)benzamide,
N-Cyclohexyl-N-methyl 4-(1H-2-thiomethylbenzimidazylmethyl)benzamide,
N-Cyclohexyl-N-methyl 4-(1H-2methylsulphinylbenzimidazylmethyl)benzamide,
N-Cyclohexyl-N-methyl 4-(1H-2-methylsulphonylbenzimidazylmethyl)benzamide,
N-Cyclohexyl-N-methyl 4-(1H-2-(2-thiomethylethyl)-benzimidazylmethyl)benzamide,
N-Cyclohexyl-N-methyl 4-(1H-2-trifluoromethylbenzimidazylmethyl)benzamide,
N-Cyclohexyl-N-methyl 4-(1H-2-(4-thiazolyl)benzimidazylmethyl)benzamide,
N-Cyclohexyl-N-methyl 4-(1H-2-phenylbenzimidazylmethyl)benzamide,
N-Cyclohexyl-N-methyl 4-(1H-2-(2-chlorophenyl)benzimidazylmethyl)benzamide,
N-Cyclohexyl-N-methyl 4-(1H-5, 6-dimethylbenzimidazylmethyl)benzamide,
N-Cyclohexyl-N-methyl 3-bromo-4-(1H-2-benzimidazylmethyl)benzamide,
N-Cyclohexyl-N-methyl 3-fluoro-4-(1H-2-benzimidazylmethyl) benzamide,
N-Cyclohexyl-N-methyl 3-methoxy-4-(1H-2-benzimidazylmethyl)benzamide,
N-Cyclohexyl 4-(1H-benzimidazylmethyl)benzenesulphonamide,
N-Cyclohexyl 4-(1H-2-methylbenzimidazylmethyl)benzenesulphonamide,
N-Cyclohexyl-N-methyl 4-(1H-benzimidazylmethyl)benzenesulphonamide,
N-Cyclohexyl-N-methyl 4-(1H-2-methylbenzimidazylmethyl)benzenesulphonamide,
N-Cyclohexyl-N-methyl 4-(1H-2-ethylbenzimidazyl methyl)benzenesulphonamide,
A) N-Cyclohexyl-N-methyl 4-(1H-2-methyl-5-chlorobenzimidazylmethyl)benzenesulphonamide,
B) N-Cyclohexyl-N-methyl 4-(1H-2-methyl-6-chlorobenzimidazylmethyl)benzenesulphonamide,
N-Cyclohexyl-N-methyl 4-(1H-2-methyl-5-nitrobenzimidazylmethyl)benzenesulphonamide,
N-Cyclohexyl-N-methyl 4-(1H-2-(2-pyridyl)benzimidazylmethyl)benzenesulphonamide,
N-Cyclohexyl-N-methyl 4-(1H-2, 5, 6-trimethylbenzimidazylmethyl)benzenesulphonamide,
N-Cyclohexyl-N-methyl 4-(1H-naphth[2,3-d]imidazylmethyl)benzenesulphonamide,
N-Cyclohexyl-N-methyl 4-(1H-2-methylnaphth[2,3-d]imidazylmethyl)benzenesulphonamide,
N-Cyclohexyl-N-methyl 4-(1H-2-(2-methyl)benzimidazylmethyl) benzenesulphonamide,
N-Methyl-N-4-(1H-2-methylbenzimidazylmethyl)benzylphenylsulphonamide,
N-Methyl-N-4-(1H-2-methylbenzimidazylmethyl)benzyl 2-naphthylsulphonamide,
N-Methyl-N-4-(1H-2-methylbenzimidazylmethyl)benzyl 4-bromophenylsulphonamide,
N-4-(1H-2-Methylbenzimidazylmethyl)benzylphenylamide,
N-4-(1H-2-Methylbenzimidazylmethyl)benzylcyclohexylamide,
N-Methyl-N-4-(1H-2-methylbenzimidazylmethyl)benzyl diphenylphosphoramide,
N-Cyclohexyl-N-methyl 4-(1-(1H-benzimidazyl)ethyl)-benzamide,
N-Cyclohexyl-N-methyl 4-(1-(1H-benzimidazyl)-propyl)benzamide,
N-Cyclohexyl-N-methyl 4-(1-(1H-benzimidazyl)but-3-enyl)benzamide,
N-Cyclohexyl-N-methyl 4-(1H-benzimidazylthiomethylmethyl)benzamide,
N-Cyclohexyl-N-methyl 4-(1H-benzimidazyldithiomethylmethyl)benzamide,
N-Cyclohexyl-N-methyl 4-(1H-benzimidazylthioethylmethyl)benzamide,
N-Cyclohexyl-N-methyl 4-(1H-benzimidazylthiophenylmethyl)benzamide,
N-Cyclohexyl-N-methyl 4-(1H-benzimidazylmethylsulphonylmethyl) benzamide,
N-Cyclohexyl-N-methyl 4-(1H-2-methylbenzimidazylthiomethylmethyl)benzamide,
N-Cyclohexyl-N-methyl 4-(1H-2-thiomethylbenzimidazylthiomethylmethyl)benzamide,
N-Cyclohexyl-N-methyl 4-(1H-benzimidazylthiomethylmethyl)benzamide,
N-Cyclohexyl-N-methyl 4-(1H-benzimidazylthiomethylmethyl)benzenesulphonamide,
N-3-Chlorophenyl 4-(1H-2-methylbenzimidazylmethyl)benzenesulphonamide,
N-Phenyl 4-(1H-2-methylbenzimidazylmethyl)benzenesulphonamide,
N-4-Bromophenyl 4-(1H-2-methylbenzimidazylmethyl)benzenesulphonamide,
N-3,4-Dimethoxyphenyl 4-(1H-2-methylbenzimidazylmethyl)benzenesulphonamide,
N-3,4,5-Trimethoxyphenyl 4-(1H-2-methylbenzimidazylmethyl)benzenesulphonamide,
N-3-Benzoylphenyl 4-(1H-2-methylbenzimidazylmethyl)benzenesulphonamide,
N-3-Benzoxyphenyl 4-(1H-2-methylbenzimidazylmethyl)benzenesulphonamide,
N-Benzyl 4-(1H-2-methylbenzimidazylmethyl)benzenesulphonamide,
N-2-Chlorobenzyl 4-(1H-2-methylbenzimidazylmethyl)benzenesulphonamide,
N-3-Chlorobenzyl 4-(1H-2-methylbenzimidazylmethyl)benzenesulphonamide, N-4-Chlorobenzyl 4-(1H-2-methylbenzimidazylmethyl)benzenesulphonamide,
N-3,4-Dimethoxybenzyl 4-(1H-2-methylbenzimidazylmethyl)benzenesulphonamide,
N-4-tert-Butylcyclohexyl 4-(1H-2-methylbenzimidazylmethyl)benzenesulphonamide,
N-1,2,3,4-Tetrahydro-1-naphthyl 4-(1H-2-methylbenzimidazylmethyl)benzenesulphonamide,
N,N-Dicyclohexyl 4-(1H-2-methylbenzimidazylmethyl)benzenesulphonamide,
N-Decyl 4-(1H-2-methylbenzimidazylmethyl)benzenesulphonamide,
N-1-Adamantyl 4-(1H-2-methylbenzimidazylmethyl)benzenesulphonamide,
N-Methyl-N-phenyl 4-(1H-2-methylbenzimidazylmethyl)benzenesulphonamide,
N-Benzyl-N-methyl 4-(1H-2-methylbenzimidazylmethyl)benzenesulphonamide,
N-Benzyl-N-phenyl 4-(1H-2-methylbenzimidazylmethyl)benzenesulphonamide,
N-Benzyl-N-2-phenylethyl 4-(1H-2-methylbenzimidazylmethyl)benzenesulphonamide,
N-3-Chlorobenzyl-N-methyl 4-(1H-2-methylbenzimidazylmethyl)benzenesulphonamide,
N-4-Chlorobenzyl-N-methyl 4-(1H-2-methylbenzimidazylmethyl)benzenesulphonamide or
N-1-Adamantyl-N-methyl 4-(1H-2-methylbenzimidazylmethyl)benzenesulphonamide
or a salt of such a compound.

27. A pharmaceutical or veterinary formulation comprising a compound as claimed in claim 1 and a pharmaceutically or veterinarily acceptable carrier.

* * * * *